US012328638B2

(12) United States Patent
Chong et al.

(10) Patent No.: US 12,328,638 B2
(45) Date of Patent: Jun. 10, 2025

(54) INFORMATION PROCESSING METHOD, APPARATUS, AND SYSTEM

(71) Applicant: HUAWEI TECHNOLOGIES CO., LTD., Guangdong (CN)

(72) Inventors: Weiwei Chong, Shenzhen (CN); Xiaobo Wu, Shenzhen (CN); Yang Xin, Shanghai (CN)

(73) Assignee: Huawei Technologies Co., Ltd., Shenzhen (CN)

( * ) Notice: Subject to any disclaimer, the term of this patent is extended or adjusted under 35 U.S.C. 154(b) by 336 days.

(21) Appl. No.: 17/893,884

(22) Filed: Aug. 23, 2022

(65) Prior Publication Data
US 2022/0408215 A1 Dec. 22, 2022

Related U.S. Application Data

(63) Continuation of application No. PCT/CN2021/072877, filed on Jan. 20, 2021.

(30) Foreign Application Priority Data

Feb. 24, 2020 (CN) .......................... 202010113338.3
May 6, 2020 (CN) .......................... 202010374718.2

(51) Int. Cl.
*H04W 4/021* (2018.01)
*H04W 4/02* (2018.01)
(Continued)

(52) U.S. Cl.
CPC ........... *H04W 4/021* (2013.01); *H04W 4/027* (2013.01); *H04W 4/029* (2018.02); *H04W 4/90* (2018.02)

(58) Field of Classification Search
CPC ....... H04W 4/02; H04W 4/021; H04W 4/027; H04W 4/029; H04W 4/90; G16H 50/80
(Continued)

(56) References Cited

U.S. PATENT DOCUMENTS 11,825,332 B2 * 11/2023 Schliwa-Bertling ........................ H04L 41/5009
2016/0127531 A1 5/2016 Halls
(Continued)

FOREIGN PATENT DOCUMENTS

CN 101621736 A 1/2010
CN 103975640 A 8/2014
(Continued)

OTHER PUBLICATIONS

Huawei et al., "Solution to multiple NWDAF instances," SA WG2 Meeting #136AH, S2-2001210, Incheon, Korea, Jan. 13-17, 2020, 7 pages.
(Continued)

*Primary Examiner* — Jean A Gelin
(74) *Attorney, Agent, or Firm* — Fish & Richardson P.C.

(57) ABSTRACT

The present disclosure relates to information processing methods, apparatus, and systems. In one example method, a first network element receives data analytics information from a first data analytics network element, where the data analytics information includes one or more of an identifier of a first terminal, activity degree information of the first terminal, moving trajectory information of the first terminal, and first risk information of the first terminal. The first network element determines an association relationship between the first terminal and an emergency event based on the data analytics information.

20 Claims, 11 Drawing Sheets

(51) Int. Cl.
    *H04W 4/029*     (2018.01)
    *H04W 4/90*      (2018.01)
(58) Field of Classification Search
    USPC ........................................................ 455/456.1
    See application file for complete search history.

(56)            References Cited

U.S. PATENT DOCUMENTS

| | | | |
|---|---|---|---|
| 2018/0150071 | A1 | 5/2018 | Ishihara et al. |
| 2019/0082312 | A1 | 3/2019 | Neybert et al. |
| 2019/0356558 | A1* | 11/2019 | Han .................. H04L 41/14 |
| 2019/0394713 | A1* | 12/2019 | Zheng ............... H04W 56/0015 |
| 2020/0100137 | A1* | 3/2020 | Panchal ............ H04W 28/0289 |
| 2020/0112921 | A1* | 4/2020 | Han .................. H04W 52/0235 |
| 2020/0218715 | A1* | 7/2020 | Chen ................. H04M 15/82 |
| 2020/0252813 | A1* | 8/2020 | Li ..................... H04W 24/08 |
| 2021/0219151 | A1* | 7/2021 | Fiorese .............. H04W 24/02 |
| 2021/0314868 | A1* | 10/2021 | Han .................. H04W 16/18 |
| 2021/0329485 | A1* | 10/2021 | Han .................. H04W 28/0236 |
| 2022/0039046 | A1* | 2/2022 | Ianev ................. H04W 24/08 |
| 2022/0078606 | A1* | 3/2022 | Maeder ............. H04L 61/5007 |
| 2022/0294606 | A1* | 9/2022 | Norrman ........... G06N 20/00 |

FOREIGN PATENT DOCUMENTS

| | | |
|---|---|---|
| CN | 105306224 A | 2/2016 |
| CN | 106576125 A | 4/2017 |
| CN | 108986921 A | 12/2018 |
| CN | 109286644 A | 1/2019 |
| CN | 109816180 A | 5/2019 |
| CN | 110677299 A | 1/2020 |
| EP | 4040727 A1 | 8/2022 |
| JP | 2022549782 A | 11/2022 |
| WO | 2006066629 A1 | 6/2006 |

OTHER PUBLICATIONS

China Mobile et al., "Clarification of emergency usage of data analytics report," 3GPP TSG-WG SA2 Meeting #137E e-meeting, S2-2002139, Elbonia, Feb. 24-27, 2020, 4 pages.

Extended European Search Report in European Appln No. 21760397.6, dated Jun. 15, 2023, 12 pages.

Tencent, "Updating NRF services based on NF profile," SA WG2 Meeting #137E (e-meeting), S2-2002232, Elbonia, Feb. 24-27, 2020, 6 pages.

Office Action in Japanese Appln. No. 2022-550810, mailed on Oct. 16, 2023, 9 pages (with English translation).

3GPP TS 23.288 V16.2.0 (Dec. 2019), "3rd Generation Partnership Project; Technical Specification Group Services and System Aspects; Architecture Enhancements for 5G System (5GS) to Support Network Data Analytics Services (Release 16)," Dec. 2019, 57 pages.

3GPP TS 23.501 V16.3.0 (Dec. 2019), "3rd Generation Partnership Project; Technical Specification Group Services and System Aspects; System Architecture for the 5G System (5GS); Stage 2 (Release 16)," Dec. 2019, total 417 pages.

3GPP TS 23.502 V16.3.0 (Dec. 2019), "3rd Generation Partnership Project; Technical Specification Group Services and System Aspects; Procedures for the 5G System (5GS); Stage 2 (Release 16)," Dec. 2019, 558 pages.

Office Action issued in Chinese Application No. 202010374718.2 on Dec. 21, 2021, 19 pages (with English translation).

Office Action issued in Chinese Application No. 202010374718.2 on Jun. 29, 2022, 17 pages (with English translation).

PCT International Search Report and Written Opinion issued in International Application No. PCT/CN2021/072877 on Apr. 16, 2021, 15 pages (with English translation).

\* cited by examiner

INFORMATION PROCESSING METHOD, APPARATUS, AND SYSTEM

CROSS-REFERENCE TO RELATED APPLICATIONS

This application is a continuation of International Patent Application No. PCT/CN2021/072877, filed on Jan. 20, 2021, which claims priority to Chinese Patent Application No. 202010113338.3, Feb. 24, 2020 and Chinese Patent Application No. 202010374718.2, May 6, 2020. The disclosures of the aforementioned applications are hereby incorporated by reference in their entireties.

TECHNICAL FIELD

Embodiments of this application relate to the field of communication technologies, and in particular, to an information processing method, an apparatus, and a system.

BACKGROUND

For an emergency event that breaks out currently, information collection personnel need to get offline to screen information about an associated user who contacts with the emergency event, to obtain information about a user associated with the emergency event. For example, to screen the user associated with the emergency event, the information collection personnel need to register, door to door, whether a user is associated, in a specific area at a specific time point, with an emergency event that occurs in a specific area. In this manner, the information collection personnel may learn, through offline information collection, whether the user is associated with the emergency event, but cannot determine, in time, a risk degree of the user associated with the emergency event. In addition, the offline screening method consumes time and labor costs.

SUMMARY

This application provides an information processing method, an apparatus, and a system, so that a first network element determines an association relationship between a terminal and an emergency event.

To achieve the foregoing objective, the following technical solutions are used in this application.

According to a first aspect, an embodiment of this application provides an information processing method, including: A first network element receives data analytics information from a first data analytics network element, where the data analytics information includes one or more of the following information: an identifier of a first terminal, activity degree information of the first terminal, moving trajectory information of the first terminal, and first risk information of the first terminal. The first network element determines an association relationship between the first terminal and an emergency event based on the data analytics information.

In the foregoing method, the first data analytics network element provides the data analytics information for the first network element. The data analytics information includes one or more of the identifier of the first terminal, the activity degree information of the first terminal, the moving trajectory information of the first terminal, and the first risk information of the first terminal, so that after receiving the data analytics information, the first network element not only can determine the association relationship between the first terminal and the emergency event based on the data analytics information, but also can determine, in time, a risk degree and the moving trajectory information that are of the first terminal. Subsequently, this helps the first network element perform an associated emergency processing operation based on the association relationship between the first terminal and the emergency event.

In a possible implementation, the moving trajectory information of the first terminal in this embodiment of this application includes one or more of the following information of the first terminal: location information, a time point of entering a location range corresponding to the location information, and stay duration in the location range. This helps the first network element determine the location information of the first terminal, the time point at which the first terminal enters the location range corresponding to the location information, and the stay duration of the first terminal in the location range.

In a possible implementation, the first risk information of the first terminal in this embodiment of this application includes one or more of the following information of the first terminal: first risk classification information, a first risk degree, and a first risk removal time point. This helps the first network element determine a risk classification to which the first terminal belongs, a risk degree of the first terminal, and a risk removal time point of the first terminal.

In a possible implementation, the association relationship between the first terminal and the emergency event in this embodiment of this application includes association indication information and/or second risk information, where the association indication information indicates whether the first terminal is associated with the emergency event, and the second risk information includes at least one of the following information of the first terminal corresponding to the emergency event: second risk classification information, a second risk degree, and a second risk removal time point.

In a possible implementation, the data analytics information is data analytics information corresponding to information about target time and information about a target area. This helps the first network element determine the information about the target time and the information about the target area that correspond to the data analytics information.

In a possible implementation, before the first network element receives the data analytics information from the first data analytics network element, the method provided in this embodiment of this application may further include: The first network element sends, to the first data analytics network element, a first request message that requests the data analytics information. This helps the first data analytics network element provide the data analytics information for the first network element based on triggering of the first request message.

In a possible implementation, the first request message includes the information about the target time and the information about the target area, and the first request message requests the data analytics information corresponding to the information about the target time and the information about the target area. This helps the first data analytics network element narrow down a range of determining the data analytics information.

In a possible implementation, the first request message includes information about a to-be-assessed area, the first request message requests data analytics information corresponding to a terminal in the to-be-assessed area, and the terminal in the to-be-assessed area includes the first terminal, or the first terminal is the terminal in the to-be-assessed area.

In a possible implementation, the first request message includes an identifier of a second terminal, the first request message requests data analytics information corresponding to the second terminal, and the second terminal includes the first terminal, or the second terminal is the first terminal. This helps the first data analytics network element receive a request from the first network element for the data analytics information corresponding to the second terminal.

In a possible implementation, the first request message includes emergency indication information, and the emergency indication information indicates, to the first data analytics network element, that the data analytics information requested by the first request message is associated with the emergency event. The emergency indication information is for helping the first data analytics network element determine to provide the first network element with the data analytics information requested by the first request message, or help the first data analytics network element determine to derive the data analytics information requested by the first request message.

In a possible implementation, the first request message includes emergency event identifier information, and the emergency event identifier information uniquely identifies the emergency event.

In a possible implementation, the first network element is an application function network element or a mobility management network element.

In a possible implementation, when the first network element is the mobility management network element, the method provided in this embodiment of this application further includes: The first network element obtains the emergency indication information. The first network element selects a data analytics network element that supports an emergency event analytics function as the first data analytics network element based on the emergency indication information.

In a possible implementation, the method provided in this embodiment of this application further includes: The first network element performs, based on the association relationship, an emergency processing operation corresponding to the emergency event.

In a possible implementation, that the first network element performs, based on the association relationship, an emergency processing operation corresponding to the emergency event includes: The first network element sends, to a sixth terminal, first notification information that notifies the sixth terminal of the association relationship between the first terminal and the emergency event; and/or the first network element sends second notification information to a second network element, where the second notification information notifies the second network element of the association relationship between the first terminal and the emergency event.

According to a second aspect, an embodiment of this application provides an information processing method, including: A first data analytics network element determines data analytics information, where the data analytics information includes one or more of the following information: an identifier of a first terminal, activity degree information of the first terminal, moving trajectory information of the first terminal, and first risk information of the first terminal. The first data analytics network element sends the data analytics information to a first network element.

In a possible implementation, the moving trajectory information of the first terminal includes one or more of the following information of the first terminal: location information, a time point of entering a location range corresponding to the location information, and stay duration in the location range.

In a possible implementation, the first risk information of the first terminal includes one or more of the following information of the first terminal: first risk classification information, a first risk degree, and a first risk removal time point.

In a possible implementation, the data analytics information is data analytics information corresponding to information about target time and information about a target area.

In a possible implementation, the method provided in this embodiment of this application further includes: The first data analytics network element receives, from the first network element, a first request message that requests the data analytics information.

In a possible implementation, the first request message includes the information about the target time and the information about the target area, and the first request message requests the data analytics information corresponding to the information about the target time and the information about the target area.

In a possible implementation, the first request message includes information about a to-be-assessed area, the first request message requests data analytics information corresponding to a terminal in the to-be-assessed area, and the terminal in the to-be-assessed area includes the first terminal.

In a possible implementation, the first request message includes an identifier of a second terminal, the first request message requests data analytics information corresponding to the second terminal, and the second terminal includes the first terminal.

In a possible implementation, the first request message includes emergency indication information, and the emergency indication information indicates, to the first data analytics network element, that the data analytics information requested by the first request message is associated with an emergency event.

In a possible implementation, the first request message includes emergency event identifier information, and the emergency event identifier information uniquely identifies the emergency event.

In a possible implementation, that the first data analytics network element determines data analytics information includes: The first data analytics network element determines the data analytics information based on the emergency indication information.

In a possible implementation, that the first data analytics network element sends the data analytics information to a first network element includes: The first data analytics network element sends the data analytics information to the first network element based on the emergency indication information.

In a possible implementation, that the first data analytics network element determines data analytics information includes: The first data analytics network element receives reference data analytics information from a second data analytics network element, where the reference data analytics information includes one or more of the following information: an identifier of a third terminal, reference activity degree information of the third terminal, reference moving trajectory information of the third terminal, and reference risk information of the third terminal, and the third terminal includes the first terminal; and/or the first data analytics network element obtains data corresponding to a fourth terminal in the to-be-assessed area, where the data includes one or more of the following information: service behavior information, location information, and moving trajectory information, and the fourth terminal includes the first terminal. The first data analytics network element determines the data analytics information based on the reference data analytics information and/or the data corresponding to the fourth terminal in the to-be-assessed area.

In a possible implementation, that the first data analytics network element determines the data analytics information based on the reference data analytics information and/or the data corresponding to the fourth terminal in the to-be-assessed area includes: The first data analytics network element determines the data analytics information based on the identifier of the third terminal, the reference activity degree information of the third terminal, and the data corresponding to the fourth terminal in the to-be-assessed area.

In a possible implementation, that the first data analytics network element determines the data analytics information based on the reference data analytics information and/or the data corresponding to the fourth terminal in the to-be-assessed area includes: The first data analytics network element determines the data analytics information based on the identifier of the third terminal and the reference moving trajectory information of the third terminal.

In a possible implementation, that the first data analytics network element determines the data analytics information based on the reference data analytics information and/or the data corresponding to the fourth terminal in the to-be-assessed area includes: The first data analytics network element determines the data analytics information based on the moving trajectory information corresponding to the fourth terminal in the to-be-assessed area.

In a possible implementation, the method provided in this embodiment of this application further includes: The first data analytics network element sends, to the second data analytics network element, a second request message that requests reference data analytics information corresponding to the information about the target time and the information about the target area.

In a possible implementation, that the first data analytics network element receives reference data analytics information from a second data analytics network element further includes: The first data analytics network element receives, from the second data analytics network element, the reference data analytics information corresponding to the information about the target time and the information about the target area.

In a possible implementation, the method provided in this embodiment of this application further includes: The first data analytics network element determines the second data analytics network element based on first information, where the first information includes one or more of the following information: the emergency indication information and the emergency event identifier information.

In a possible implementation, the first network element is an application function network element or a mobility management network element.

In a possible implementation, the first data analytics network element is a data analytics network element that supports an emergency event analytics function, and the second data analytics network element is a data analytics network element that supports the emergency event analytics function.

According to a third aspect, an embodiment of this application provides an information processing method, including: A second data analytics network element determines reference data analytics information, where the reference data analytics information includes one or more of the following information: an identifier of a third terminal, reference activity degree information of the third terminal, reference moving trajectory information of the third terminal, and reference risk information of the third terminal. The second data analytics network element sends the reference data analytics information to a first data analytics network element. The reference activity degree information is activity degree information of the terminal in a target area. The reference moving trajectory information refers to moving trajectory information of the terminal in the target area. The reference risk information is risk information of the terminal in the target area.

In a possible implementation, the third terminal is a terminal associated with an emergency event.

In a possible implementation, the reference moving trajectory information includes one or more of the following information: reference location information, a time point of entering a location range corresponding to the reference location information, and stay duration in the reference location range.

In a possible implementation, the reference risk information includes one or more of the following information: reference risk classification information, a reference risk degree, and a reference risk removal time point.

In a possible implementation, the reference data analytics information is reference data analytics information corresponding to information about target time and information about the target area.

In a possible implementation, that a second data analytics network element determines reference data analytics information includes: The second data analytics network element obtains first data, where the first data includes one or more of the following information of a fifth terminal corresponding to the information about the target time and the information about the target area: an identifier, location information, moving trajectory information, and service behavior information that are of the terminal, and the fifth terminal includes the third terminal. The second data analytics network element determines the reference data analytics information based on the first data.

In a possible implementation, the second data analytics network element determines the reference data analytics information based on the location information and the service behavior information that are of the fifth terminal in a first time period and the target area.

In a possible implementation, the method provided in this embodiment of this application further includes: The second data analytics network element receives, from the first data analytics network element, a second request message that requests the reference data analytics information corresponding to the information about the target time and the information about the target area.

In a possible implementation, the second request message includes one or more identifiers of one or more terminals, and the second request message requests reference data analytics information corresponding to the one or more terminals. The one or more terminals include the third terminal.

According to a fourth aspect, an embodiment of this application provides an information processing apparatus. The information processing apparatus can implement the method according to any one of the first aspect or the possible implementations of the first aspect, and therefore can further implement beneficial effects in any one of the first aspect or the possible implementations of the first aspect. The information processing apparatus may be a first network element, or may be an apparatus that supports the first network element in implementing the method according to any one of the first aspect or the possible implementations of the first aspect, for example, a chip used in the first network element. The information processing apparatus may implement the foregoing method by using software or hardware, or by hardware executing corresponding software.

In an example, the information processing apparatus includes: a communication unit, configured to receive data analytics information from a first data analytics network element, where the data analytics information includes one or more of the following information: an identifier of a first terminal, activity degree information of the first terminal, moving trajectory information of the first terminal, and first risk information of the first terminal; and a processing unit, configured to determine an association relationship between the first terminal and an emergency event based on the data analytics information.

In a possible implementation, the moving trajectory information of the first terminal includes one or more of the following information of the first terminal: location information, a time point of entering a location range corresponding to the location information, and stay duration in the location range.

In a possible implementation, the first risk information of the first terminal includes one or more of the following information of the first terminal: first risk classification information, a first risk degree, and a first risk removal time point.

In a possible implementation, the association relationship between the first terminal and the emergency event includes association indication information and/or second risk information, where the association indication information indicates whether the first terminal is associated with the emergency event, and the second risk information includes at least one of the following information of the first terminal corresponding to the emergency event: second risk classification information, a second risk degree, and a second risk removal time point.

In a possible implementation, the data analytics information is data analytics information corresponding to information about target time and information about a target area.

In a possible implementation, the communication unit is further configured to send a first request message to the first data analytics network element, where the first request message requests the data analytics information.

In a possible implementation, the first request message includes the information about the target time and the information about the target area, and the first request message requests the data analytics information corresponding to the information about the target time and the information about the target area.

In a possible implementation, the first request message includes information about a to-be-assessed area, the first request message requests data analytics information corresponding to a terminal in the to-be-assessed area, and the terminal in the to-be-assessed area includes the first terminal.

In a possible implementation, the first request message includes an identifier of a second terminal, the first request message requests data analytics information corresponding to the second terminal, and the second terminal includes the first terminal.

In a possible implementation, the first request message includes emergency indication information, and the emergency indication information indicates, to the first data analytics network element, that the data analytics information requested by the first request message is associated with the emergency event.

In a possible implementation, the first request message includes emergency event identifier information, and the emergency event identifier information uniquely identifies the emergency event.

In a possible implementation, the information processing apparatus is an application function network element or a mobility management network element.

In a possible implementation, when the information processing apparatus is the mobility management network element, the communication unit is configured to obtain the emergency indication information. The processing unit is further configured to select a data analytics network element that supports an emergency event analytics function as the first data analytics network element based on the emergency indication information.

In a possible implementation, when the information processing apparatus is the mobility management network element, the processing unit is further configured to determine the identifier of the second terminal.

In a possible implementation, the processing unit is further configured to perform, based on the association relationship, an emergency processing operation corresponding to the emergency event.

In a possible implementation, that the processing unit is further configured to perform, based on the association relationship, an emergency processing operation corresponding to the emergency event includes: The processing unit is configured to send first notification information to a sixth terminal by using the communication unit, where the first notification information notifies the sixth terminal of the association relationship between the first terminal and the emergency event; and/or the processing unit is configured to send second notification information to a second network element by using the communication unit, where the second notification information notifies the second network element of the association relationship between the first terminal and the emergency event.

For example, when the information processing apparatus is the chip or a chip system in the first network element, the processing unit may be a processor, and the communication unit may be a communication interface. For example, the communication interface may be an input/output interface, a pin, or a circuit. The processing unit executes instructions stored in a storage unit, to enable the first network element to implement the information processing method according to any one of the first aspect or the possible implementations of the first aspect. The storage unit may be a storage unit (for example, a register or a cache) in the chip, or may be a storage unit (for example, a read-only memory or a random access memory) that is in the first network element and that is outside the chip.

According to a fifth aspect, an embodiment of this application provides an information processing apparatus. The information processing apparatus can implement the method according to any one of the second aspect or the possible implementations of the second aspect, and therefore can further implement beneficial effects in any one of the second aspect or the possible implementations of the second aspect. The information processing apparatus may be a first data analytics network element, or may be an apparatus that supports the first data analytics network element in implementing the method according to any one of the second aspect or the possible implementations of the second aspect, for example, a chip used in the first data analytics network element. The information processing apparatus may implement the foregoing method by using software or hardware, or by hardware executing corresponding software.

In an example, the information processing apparatus includes: a processing unit, configured to determine data analytics information, where the data analytics information includes one or more of the following information: an identifier of a first terminal, activity degree information of the first terminal, moving trajectory information of the first terminal, and first risk information of the first terminal; and a communication unit, configured to send the data analytics information to a first network element.

In a possible implementation, the moving trajectory information of the first terminal includes one or more of the following information of the first terminal: location information, a time point of entering a location range corresponding to the location information, and stay duration in the location range.

In a possible implementation, the first risk information of the first terminal includes one or more of the following information of the first terminal: first risk classification information, a first risk degree, and a first risk removal time point.

In a possible implementation, the data analytics information is data analytics information corresponding to information about target time and information about a target area.

In a possible implementation, the communication unit is further configured to receive, from the first network element, a first request message that requests the data analytics information.

In a possible implementation, the first request message includes the information about the target time and the information about the target area, and the first request message requests the data analytics information corresponding to the information about the target time and the information about the target area.

In a possible implementation, the first request message includes information about a to-be-assessed area, the first request message requests data analytics information corresponding to a terminal in the to-be-assessed area, and the terminal in the to-be-assessed area includes the first terminal.

In a possible implementation, the first request message includes an identifier of a second terminal, the first request message requests data analytics information corresponding to the second terminal, and the second terminal includes the first terminal.

In a possible implementation, the first request message includes emergency indication information, and the emergency indication information indicates, to the information processing apparatus, that the data analytics information requested by the first request message is associated with an emergency event.

In a possible implementation, the first request message includes emergency event identifier information, and the emergency event identifier information uniquely identifies the emergency event.

In a possible implementation, the processing unit is configured to determine the data analytics information based on the emergency indication information.

In a possible implementation, the processing unit is configured to send the data analytics information to the first network element by using the communication unit based on the emergency indication information.

In a possible implementation, the communication unit is configured to receive reference data analytics information from a second data analytics network element, where the reference data analytics information includes one or more of the following information: an identifier of a third terminal, reference activity degree information of the third terminal, reference moving trajectory information of the third terminal, and reference risk information of the third terminal, and the third terminal includes the first terminal; and/or the communication unit is configured to obtain data corresponding to a fourth terminal in the to-be-assessed area, where the data includes one or more of the following information: service behavior information, location information, and moving trajectory information, and the fourth terminal includes the first terminal. The processing unit is configured to determine the data analytics information based on the reference data analytics information and/or the data corresponding to the fourth terminal in the to-be-assessed area.

In a possible implementation, that the processing unit is configured to determine the data analytics information based on the reference data analytics information and/or the data corresponding to the fourth terminal in the to-be-assessed area is specifically: The processing unit is configured to determine the data analytics information based on the identifier of the third terminal, the reference activity degree information of the third terminal, and the data corresponding to the fourth terminal in the to-be-assessed area.

In a possible implementation, that the processing unit is configured to determine the data analytics information based on the reference data analytics information and/or the data corresponding to the fourth terminal in the to-be-assessed area is specifically: The processing unit is configured to determine the data analytics information based on the identifier of the third terminal and the reference moving trajectory information of the third terminal.

In a possible implementation, that the processing unit is configured to determine the data analytics information based on the reference data analytics information and/or the data corresponding to the fourth terminal in the to-be-assessed area is specifically: The processing unit is configured to determine the data analytics information based on the moving trajectory information corresponding to the fourth terminal in the to-be-assessed area.

In a possible implementation, the communication unit is configured to send a second request message to the second data analytics network element, where the second request message requests reference data analytics information corresponding to the information about the target time and the information about the target area.

In a possible implementation, that the communication unit is configured to receive reference data analytics information from a second data analytics network element is specifically: The communication unit is configured to receive, from the second data analytics network element, the reference data analytics information corresponding to the information about the target time and the information about the target area.

In a possible implementation, the processing unit is further configured to determine the second data analytics network element based on first information, where first information includes one or more of the following information: the emergency indication information and the emergency event identifier information.

In a possible implementation, the first network element is an application function network element or a mobility management network element.

For example, when the information processing apparatus is the chip or a chip system in the first data analytics network element, the processing unit may be a processor, and the communication unit may be a communication interface. For example, the communication interface may be an input/output interface, a pin, or a circuit. The processing unit executes instructions stored in a storage unit, to enable the first data analytics network element to implement the information processing method according to any one of the second aspect or the possible implementations of the second aspect. The storage unit may be a storage unit (for example, a register or a cache) in the chip, or may be a storage unit (for example, a read-only memory or a random access memory) that is in the first data analytics network element and that is outside the chip.

According to a sixth aspect, an embodiment of this application provides an information processing apparatus. The information processing apparatus can implement the method according to any one of the third aspect or the possible implementations of the third aspect, and therefore can further implement beneficial effects in any one of the third aspect or the possible implementations of the third aspect. The information processing apparatus may be a second data analytics network element, or may be an apparatus that supports the second data analytics network element in implementing the method according to any one of the third aspect or the possible implementations of the third aspect, for example, a chip used in the second data analytics network element. The information processing apparatus may implement the foregoing method by using software or hardware, or by hardware executing corresponding software.

In an example, this embodiment of this application provides the information processing apparatus, including: a processing unit, configured to determine reference data analytics information, where the reference data analytics information includes one or more of the following information: an identifier of a third terminal, reference activity degree information of the third terminal, reference moving trajectory information of the third terminal, and reference risk information of the third terminal; and a communication unit, configured to send the reference data analytics information to a first data analytics network element.

In a possible implementation, the third terminal is a terminal associated with an emergency event.

In a possible implementation, the reference moving trajectory information includes one or more of the following information: reference location information, a time point of entering a location range corresponding to the reference location information, and stay duration in the reference location range.

In a possible implementation, the reference risk information includes one or more of the following information: reference risk classification information, a reference risk degree, and a reference risk removal time point.

In a possible implementation, the reference data analytics information is reference data analytics information corresponding to information about target time and information about a target area.

In a possible implementation, the communication unit is configured to obtain first data, where the first data includes one or more of the following information of a fifth terminal corresponding to the information about the target time and the information about the target area: an identifier, location information, moving trajectory information, and service behavior information that are of the terminal, and the fifth terminal includes the third terminal. The processing unit is configured to determine the reference data analytics information based on the first data.

In a possible implementation, the processing unit is configured to determine the reference data analytics information based on the location information and the service behavior information that are of the fifth terminal in a first time period and the target area.

In a possible implementation, the communication unit is configured to receive, from the first data analytics network element, a second request message that requests the reference data analytics information corresponding to the information about the target time and the information about the target area.

In a possible implementation, the second request message includes an identifier of one or more terminals, and the second request message requests reference data analytics information corresponding to the one or more terminals. The one or more terminals include the third terminal.

In a possible implementation, the information processing apparatus is a data analytics network element that supports an emergency event analytics function.

For example, when the information processing apparatus is the chip or a chip system in the second data analytics network element, the processing unit may be a processor, and the communication unit may be a communication interface. For example, the communication interface may be an input/output interface, a pin, or a circuit. The processing unit executes instructions stored in a storage unit, to enable the second data analytics network element to implement the information processing method according to any one of the third aspect or the possible implementations of the third aspect. The storage unit may be a storage unit (for example, a register or a cache) in the chip, or may be a storage unit (for example, a read-only memory or a random access memory) that is in the second data analytics network element and that is outside the chip.

According to a seventh aspect, an embodiment of this application provides an information processing method, including: A first data analytics network element obtains, from a second data analytics network element, reference data analytics information corresponding to third terminals, where the third terminal includes a terminal that resided in a target area during a target period. The first data analytics network element determines, based on the reference data analytics information of the third terminals, data analytics information corresponding to first terminals, where the data analytics information corresponding to the first terminals includes one or more of the following information: a quantity of the first terminals, aggregated activity degree information of the first terminals, aggregated moving trajectory information of the first terminals, and aggregated risk information of the first terminals, the first terminal includes a terminal that is in the third terminals and that is in a to-be-assessed area, or the first terminal includes a target terminal, and the target terminal belongs to both the third terminals and second terminals. The first data analytics network element sends the data analytics information corresponding to the first terminals to a first network element.

It should be understood that there may be a plurality of first terminals. That the target terminal belongs to both the third terminals and second terminals may mean that the target terminal is an intersection terminal of the third terminals and the second terminals.

In a possible implementation, the method provided in this embodiment of this application further includes: The first data analytics network element receives a first request message from the first network element, where the first request message requests data analytics information corresponding to the first terminals.

In a possible implementation, the first request message includes one or more of area information corresponding to the target area and time information corresponding to the target period.

In a possible implementation, the first request message includes one or more of area information corresponding to the to-be-assessed area and identifiers of the second terminals. If the first request message includes the area information corresponding to the to-be-assessed area, the first request message requests data analytics information corresponding to terminals in the to-be-assessed area. The terminals in the to-be-assessed area include the first terminals, or the first terminals are the terminals in the to-be-assessed area. If the first request message includes the identifiers of the second terminals, the first request message requests data analytics information corresponding to the second terminals. The second terminals include the first terminals, or the second terminals are the first terminals.

In a possible implementation, the first request message includes emergency indication information, and the emergency indication information indicates, to the first data analytics network element, that the data analytics information requested by the first request message is associated with an emergency event or a public safety event.

In a possible implementation, the first request message includes emergency event identifier information, and the emergency event identifier information uniquely identifies the emergency event.

In a possible implementation, the reference data analytics information corresponding to the third terminals includes one or more of the following information: identifiers of the third terminals, a quantity of the third terminals, reference activity degree information of the third terminals, reference moving trajectory information of the third terminals, reference risk information of the third terminals, aggregated reference activity degree information of the third terminals, aggregated reference moving trajectory information of the third terminals, and aggregated reference risk information of the third terminals.

In a possible implementation, the method provided in this embodiment of this application may further include: The first data analytics network element obtains first input data corresponding to the third terminals in the to-be-assessed area, where the first input data includes one or more of the following information: service behavior information, location information, and moving trajectory information.

In a possible implementation, the moving trajectory information corresponding to the third terminals in the to-be-assessed area includes one or more of the following information of the third terminals: location information, a time point of entering a location range corresponding to the location information, and stay duration in the location range.

In a possible implementation, that the first data analytics network element determines, based on the reference data analytics information corresponding to the third terminals, data analytics information corresponding to first terminals includes: The first data analytics network element determines, based on the reference data analytics information corresponding to the third terminal and the first input data, the data analytics information corresponding to the first terminals.

In a possible implementation, the method provided in this embodiment of this application may further include: The first data analytics network element obtains second input data corresponding to the target terminal, where the second input data includes one or more of the following information: service behavior information, location information, and moving trajectory information. The moving trajectory information corresponding to the target terminal includes one or more of the following information of the target terminal: the location information, a time point of entering a location range corresponding to the location information, and stay duration in the location range.

In a possible implementation, that the first data analytics network element determines, based on the reference data analytics information corresponding to the third terminals, data analytics information corresponding to first terminals includes: The first data analytics network element determines, based on reference data analytics information and the second input data that correspond to the target terminal, the data analytics information corresponding to the first terminals.

In a possible implementation, the aggregated activity degree information of the first terminals includes average information of activity degree information of the first terminals and/or variance information of the activity degree information of the first terminals.

For example, the aggregated activity degree information may include average activity degree information of a plurality of first terminals or an activity degree variance analytics result of the plurality of first terminals. When an activity degree of each first terminal is represented as a value, the average activity degree information of the plurality of first terminals may be an average value of activity degree values corresponding to the first terminals, and the activity degree variance analytics result of the plurality of first terminals may be a variance of the activity degree values corresponding to the first terminals. When an activity degree of each first terminal is represented as a level, weighting calculation may be performed, based on a ratio, on levels corresponding to different first terminals, to obtain a weighted value, and cosine classification processing is performed on the weighted value. A level indicated by an obtained cosine classification result is used as an average activity degree analytics result of the plurality of first terminals, and the activity degree variance analytics result of the plurality of first terminals may be a variance corresponding to activity degree levels corresponding to the first terminals.

In a possible implementation, the aggregated moving trajectory information of the first terminal includes a union of locations of moving trajectories of the plurality of first terminals or a union of the moving trajectories.

In a possible implementation, the aggregated risk information of the first terminal includes average information of risk information of the first terminals and/or variance information of the risk information of the first terminals. For example, the risk information of the first terminals includes one or more of the following information of the first terminals: risk classification information, a risk degree, and a risk removal time point. The risk information may also be referred to as a risk analytics result.

For example, the aggregated risk information may include average risk information of the plurality of first terminals or a risk variance analytics result of the plurality of first terminals. An average risk degree analytics result is similar to the average activity degree analytics result. When a risk degree of each first terminal is represented as a value, the average risk degree analytics result of the plurality of first terminals may be an average value of risk degree values corresponding to the first terminals, and a risk degree variance analytics result of the plurality of first terminals may be a variance of the risk degree values corresponding to the first terminals. When a risk degree of each first terminal is represented as a level, weighting calculation may be performed, based on a ratio, on levels corresponding to different first terminals, to obtain a weighted value, and cosine classification processing is performed on the weighted value. A level indicated by an obtained cosine classification result is used as the average risk degree analytics result of the plurality of first terminals, and the risk degree variance analytics result of the plurality of first terminals may be a variance of risk degree levels corresponding to the first terminals.

There are a plurality of first terminals, a plurality of second terminals, and a plurality of third terminals.

According to an eighth aspect, an embodiment of this application provides an information processing method, including: A first network element receives, from a first data analytics network element, data analytics information corresponding to first terminals, where the data analytics information corresponding to the first terminals includes one or more of the following information: a quantity of the first terminals, aggregated activity degree information of the first terminals, aggregated moving trajectory information of the first terminals, and aggregated risk information of the first terminals, the first terminal includes a terminal that is in third terminals and that is in a to-be-assessed area, or the first terminal includes a target terminal, the target terminal belongs to both the third terminals and second terminals, and the third terminal includes a terminal that resided in a target area during a target period. The first network element determines an association relationship between the to-be-assessed area and an emergency event or an association relationship between the second terminals and the emergency event based on the data analytics information corresponding to the first terminals.

The emergency event in this embodiment of this application may be, for example, a public safety event.

In the foregoing method, the first network element determines the association relationship between the to-be-assessed area and the emergency event or the association relationship between the second terminals and the emergency event based on information such as the quantity of the first terminals. In this way, a danger degree of the second terminals or the to-be-assessed area can be reflected based on the association relationship. For example, a stronger association with the emergency event indicates a higher danger level. Then, this helps the first network element execute an associated emergency event (for example, an epidemic) processing policy based on the danger degree of the second terminals or the to-be-assessed area. For example, if the quantity of the first terminals is greater than a first preset value, the first network element determines that the to-be-assessed area is associated with the emergency event, or determines the association relationship between the second terminals and the emergency event. In addition, the danger degree is high, and measures such as epidemic prevention and closure need to be taken.

In a possible implementation, the method provided in this embodiment of this application includes: The first network element determines, based on the data analytics information corresponding to the first terminals, a danger degree of the to-be-assessed area or the second terminals that is caused by the emergency event.

In a possible implementation, the method provided in this embodiment of this application further includes: The first network element sends a first request message to the first data analytics network element, where the first request message requests the data analytics information corresponding to the first terminals.

In a possible implementation, the first request message includes one or more of area information corresponding to the target area and time information corresponding to the target period.

In a possible implementation, the first request message includes one or more of area information corresponding to the to-be-assessed area and identifiers of the second terminals. If the first request message includes the area information corresponding to the to-be-assessed area, the first request message requests data analytics information corresponding to terminals in the to-be-assessed area. The terminals in the to-be-assessed area include the first terminals, or the first terminals are the terminals in the to-be-assessed area. If the first request message includes the identifiers of the second terminals, the first request message requests data analytics information corresponding to the second terminals. The second terminals include the first terminals, or the second terminals are the first terminals.

In a possible implementation, the first request message includes emergency indication information, and the emergency indication information indicates, to the first data analytics network element, that the data analytics information requested by the first request message is associated with the emergency event or a public safety event.

In a possible implementation, the first request message includes emergency event identifier information, and the emergency event identifier information uniquely identifies the emergency event.

In a possible implementation, the first network element is an application function network element or a mobility management network element.

In a possible implementation, when the first network element is the mobility management network element, the method provided in this embodiment of this application further includes: The first network element obtains the emergency indication information. The first network element selects a data analytics network element that supports an emergency event analytics function as the first data analytics network element based on the emergency indication information.

In a possible implementation, the method provided in this embodiment of this application further includes: The first network element performs, based on the association relationship, an emergency processing operation corresponding to the emergency event. Alternatively, in a possible implementation, the method provided in this embodiment of this application further includes: The first network element performs, based on the association relationship, an emergency processing operation corresponding to the public safety event.

In a possible implementation, that the first network element performs, based on the association relationship, an emergency processing operation corresponding to the emergency event includes: The first network element sends first notification information to sixth terminals, where the first notification information notifies the sixth terminals of the association relationship between the to-be-assessed area and the emergency event, or the first notification information notifies the sixth terminals of an association relationship between the to-be-assessed area and the public safety event, and the sixth terminal includes a terminal that is currently in the to-be-assessed area; and/or the first network element sends second notification information to a second network element, where the second notification information notifies the second network element of the association relationship between the to-be-assessed area and the emergency event, or the second notification information notifies the second network element of an association relationship between the to-be-assessed area and the public safety event.

In a possible implementation, that the first network element performs, based on the association relationship, an emergency processing operation corresponding to the emergency event includes: The first network element sends third notification information to a seventh terminal, where the third notification information notifies the seventh terminal of the association relationship between the second terminals and the emergency event, and the seventh terminal belongs to the second terminals; and/or the first network element sends fourth notification information to a second network element, where the fourth notification information notifies the second network element of the association relationship between the second terminals and the emergency event.

According to a ninth aspect, an embodiment of this application provides an information processing apparatus. The information processing apparatus can implement the method according to any one of the seventh aspect or the possible implementations of the seventh aspect, and therefore can further implement beneficial effects in any one of the seventh aspect or the possible implementations of the seventh aspect. The information processing apparatus may be a first data analytics network element, or may be an apparatus that supports the first data analytics network element in implementing the method according to any one of the seventh aspect or the possible implementations of the seventh aspect, for example, a chip used in the first data analytics network element. The information processing apparatus may implement the foregoing method by using software or hardware, or by hardware executing corresponding software.

In an example, this embodiment of this application provides the information processing apparatus, including: a communication unit, configured to obtain, from a second data analytics network element, reference data analytics information corresponding to third terminals, where the third terminal includes a terminal that resided in a target area during a target period; and a processing unit, configured to determine, based on the reference data analytics information of the third terminals, data analytics information corresponding to first terminals, where the data analytics information corresponding to the first terminals includes one or more of the following information: a quantity of the first terminals, aggregated activity degree information of the first terminals, aggregated moving trajectory information of the first terminals, and aggregated risk information of the first terminals, the first terminal includes a terminal that is in the third terminals and that is in a to-be-assessed area, or the first terminal includes a target terminal, and the target terminal belongs to both the third terminals and second terminals. The communication unit is configured to send the data analytics information corresponding to the first terminals to a first network element.

It should be understood that there may be a plurality of first terminals. That the target terminal belongs to both the third terminals and second terminals may mean that the target terminal is an intersection terminal of the third terminals and the second terminals.

In a possible implementation, the communication unit is further configured to receive a first request message from the first network element, where the first request message requests data analytics information corresponding to the first terminals.

In a possible implementation, the first request message includes one or more of area information corresponding to the target area and time information corresponding to the target period.

In a possible implementation, the first request message includes one or more of area information corresponding to the to-be-assessed area and identifiers of the second terminals. If the first request message includes the area information corresponding to the to-be-assessed area, the first request message requests data analytics information corresponding to terminals in the to-be-assessed area. The terminals in the to-be-assessed area include the first terminals, or the first terminals are the terminals in the to-be-assessed area. If the first request message includes the identifiers of the second terminals, the first request message requests data analytics information corresponding to the second terminals. The second terminals include the first terminals, or the second terminals are the first terminals.

In a possible implementation, the first request message includes emergency indication information, and the emergency indication information indicates, to the first data analytics network element, that the data analytics information requested by the first request message is associated with an emergency event or a public safety event.

In a possible implementation, the first request message includes emergency event identifier information, and the emergency event identifier information uniquely identifies the emergency event.

In a possible implementation, the reference data analytics information corresponding to the third terminals includes one or more of the following information: identifiers of the third terminals, a quantity of the third terminals, reference activity degree information of the third terminals, reference moving trajectory information of the third terminals, reference risk information of the third terminals, aggregated reference activity degree information of the third terminals, aggregated reference moving trajectory information of the third terminals, and aggregated reference risk information of the third terminals.

In a possible implementation, the communication unit is further configured to obtain first input data corresponding to the third terminals in the to-be-assessed area, where the first input data includes one or more of the following information: service behavior information, location information, and moving trajectory information.

In a possible implementation, the moving trajectory information corresponding to the third terminals in the to-be-assessed area includes one or more of the following information of the third terminals: location information, a time point of entering a location range corresponding to the location information, and stay duration in the location range.

In a possible implementation, the processing unit is configured to determine, based on the reference data analytics information corresponding to the third terminal and the first input data, the data analytics information corresponding to the first terminals.

In a possible implementation, the communication unit is further configured to obtain second input data corresponding to the target terminal, where the second input data includes one or more of the following information: service behavior information, location information, and moving trajectory information. The moving trajectory information corresponding to the target terminal includes one or more of the following information of the target terminal: the location information, a time point of entering a location range corresponding to the location information, and stay duration in the location range.

In a possible implementation, the processing unit is configured to determine, based on reference data analytics information and the second input data that correspond to the target terminal, the data analytics information corresponding to the first terminals.

In a possible implementation, the aggregated activity degree information of the first terminals includes average information of activity degree information of the first terminals and/or variance information of the activity degree information of the first terminals.

For example, the aggregated activity degree information may include average activity degree information of a plurality of first terminals or an activity degree variance analytics result of the plurality of first terminals. When an activity degree of each first terminal is represented as a value, the average activity degree information of the plurality of first terminals may be an average value of activity degree values corresponding to the first terminals, and the activity degree variance analytics result of the plurality of first terminals may be a variance of the activity degree values corresponding to the first terminals. When an activity degree of each first terminal is represented as a level, weighting calculation may be performed, based on a ratio, on levels corresponding to different first terminals, to obtain a weighted value, and cosine classification processing is performed on the weighted value. A level indicated by an obtained cosine classification result is used as an average activity degree analytics result of the plurality of first terminals, and the activity degree variance analytics result of the plurality of first terminals may be a variance corresponding to activity degree levels corresponding to the first terminals.

In a possible implementation, the aggregated moving trajectory information of the first terminal includes a union of locations of moving trajectories of the plurality of first terminals or a union of the moving trajectories.

In a possible implementation, the aggregated risk information of the first terminal includes average information of risk information of the first terminals and/or variance information of the risk information of the first terminals. For example, the risk information of the first terminals includes one or more of the following information of the first terminals: risk classification information, a risk degree, and a risk removal time point. The risk information may also be referred to as a risk analytics result.

For example, the aggregated risk information may include average risk information of the plurality of first terminals or a risk variance analytics result of the plurality of first terminals. An average risk degree analytics result is similar to the average activity degree analytics result. When a risk degree of each first terminal is represented as a value, the average risk degree analytics result of the plurality of first terminals may be an average value of risk degree values corresponding to the first terminals, and a risk degree variance analytics result of the plurality of first terminals may be a variance of the risk degree values corresponding to the first terminals. When a risk degree of each first terminal is represented as a level, weighting calculation may be performed, based on a ratio, on levels corresponding to different first terminals, to obtain a weighted value, and cosine classification processing is performed on the weighted value. A level indicated by an obtained cosine classification result is used as the average risk degree analytics result of the plurality of first terminals, and the risk degree variance analytics result of the plurality of first terminals may be a variance of risk degree levels corresponding to the first terminals.

For example, when the information processing apparatus is the chip or a chip system in the first data analytics network element, the processing unit may be a processor, and the communication unit may be a communication interface. For example, the communication interface may be an input/output interface, a pin, or a circuit. The processing unit executes instructions stored in a storage unit, to enable the first data analytics network element to implement the information processing method according to any one of the seventh aspect or the possible implementations of the seventh aspect. The storage unit may be a storage unit (for example, a register or a cache) in the chip, or may be a storage unit (for example, a read-only memory or a random access memory) that is in the first data analytics network element and that is outside the chip.

According to a tenth aspect, an embodiment of this application provides an information processing apparatus. The information processing apparatus can implement the method according to any one of the eighth aspect or the possible implementations of the eighth aspect, and therefore can further implement beneficial effects in any one of the eighth aspect or the possible implementations of the eighth aspect. The information processing apparatus may be a first network element, or may be an apparatus that supports the first network element in implementing the method according to any one of the eighth aspect or the possible implementations of the eighth aspect, for example, a chip used in the first network element. The information processing apparatus may implement the foregoing method by using software or hardware, or by hardware executing corresponding software.

The information processing apparatus includes a communication unit, configured to receive, from a first data analytics network element, data analytics information corresponding to first terminals, where the data analytics information corresponding to the first terminals includes one or more of the following information: a quantity of the first terminals, aggregated activity degree information of the first terminals, aggregated moving trajectory information of the first terminals, and aggregated risk information of the first terminals, the first terminal includes a terminal that is in third terminals and that is in a to-be-assessed area, or the first terminal includes a target terminal, the target terminal belongs to both the third terminals and second terminals, and the third terminal includes a terminal that resided in a target area during a target period; and a processing unit, configured to determine an association relationship between the to-be-assessed area and an emergency event or an association relationship between the second terminals and the emergency event based on the data analytics information corresponding to the first terminals.

In the foregoing method, the processing unit determines the association relationship between the to-be-assessed area and the emergency event or the association relationship between the second terminals and the emergency event based on information such as the quantity of the first terminals. In this way, a danger degree of the second terminals or the to-be-assessed area can be reflected based on the association relationship. For example, a stronger association with the emergency event indicates a higher danger level. Then, this helps the processing unit execute an associated epidemic processing policy based on the danger degree of the second terminals or the to-be-assessed area. For example, if the quantity of the first terminals is greater than a first preset value, the first network element determines that the to-be-assessed area is associated with the emergency event. In addition, the danger degree is high, and measures such as epidemic prevention and closure need to be taken.

In a possible implementation, the processing unit is further configured to determine, based on the data analytics information corresponding to the first terminals, a danger degree of the to-be-assessed area or the second terminals that is caused by the emergency event.

In a possible implementation, the communication unit is further configured to send a first request message to the first data analytics network element, where the first request message requests the data analytics information corresponding to the first terminals.

In a possible implementation, the first request message includes one or more of area information corresponding to the target area and time information corresponding to the target period.

In a possible implementation, the first request message includes one or more of area information corresponding to the to-be-assessed area and identifiers of the second terminals. If the first request message includes the area information corresponding to the to-be-assessed area, the first request message requests data analytics information corresponding to terminals in the to-be-assessed area. The terminals in the to-be-assessed area include the first terminals, or the first terminals are the terminals in the to-be-assessed area. If the first request message includes the identifiers of the second terminals, the first request message requests data analytics information corresponding to the second terminals. The second terminals include the first terminals, or the second terminals are the first terminals.

In a possible implementation, the first request message includes emergency indication information, and the emergency indication information indicates, to the first data analytics network element, that the data analytics information requested by the first request message is associated with the emergency event or a public safety event.

In a possible implementation, the first request message includes emergency event identifier information, and the emergency event identifier information uniquely identifies the emergency event.

In a possible implementation, the communication apparatus is an application function network element or a mobility management network element.

In a possible implementation, when the communication apparatus is the mobility management network element, the communication unit is further configured to obtain the emergency indication information. The processing unit is configured to select a data analytics network element that supports an emergency event analytics function as the first data analytics network element based on the emergency indication information.

In a possible implementation, the processing unit is further configured to perform, based on the association relationship, an emergency processing operation corresponding to the emergency event.

In a possible implementation, that the processing unit is further configured to perform, based on the association relationship, an emergency processing operation corresponding to the emergency event includes: The processing unit is further configured to send first notification information to sixth terminals by using the communication unit, where the first notification information notifies the sixth terminals of the association relationship between the to-be-assessed area and the emergency event, or the first notification information notifies the sixth terminals of an association relationship between the to-be-assessed area and the public safety event, and the sixth terminal includes a terminal that is currently in the to-be-assessed area; and/or the first network element sends second notification information to a second network element, where the second notification information notifies the second network element of the association relationship between the to-be-assessed area and the emergency event, or the second notification information notifies the second network element of an association relationship between the to-be-assessed area and the public safety event.

In a possible implementation, that the processing unit is further configured to perform, based on the association relationship, an emergency processing operation corresponding to the emergency event includes: The processing unit is further configured to send third notification information to a seventh terminal by using the communication unit, where the third notification information notifies the seventh terminal of the association relationship between the second terminals and the emergency event, and the seventh terminal belongs to the second terminals; and/or the first network element sends fourth notification information to a second network element, where the fourth notification information notifies the second network element of the association relationship between the second terminals and the emergency event.

For example, when the information processing apparatus is the chip or a chip system in the first network element, the processing unit may be a processor, and the communication unit may be a communication interface. For example, the communication interface may be an input/output interface, a pin, or a circuit. The processing unit executes instructions stored in a storage unit, to enable the first network element to implement the information processing method according to any one of the eighth aspect or the possible implementations of the eighth aspect. The storage unit may be a storage unit (for example, a register or a cache) in the chip, or may be a storage unit (for example, a read-only memory or a random access memory) that is in the first network element and that is outside the chip.

According to an eleventh aspect, an embodiment of this application provides a computer-readable storage medium. The computer-readable storage medium stores a computer program or instructions. When the computer program or the instructions are run on a computer, the computer is enabled to perform the information processing method according to any one of the first aspect or the possible implementations of the first aspect.

According to a twelfth aspect, an embodiment of this application provides a computer-readable storage medium. The computer-readable storage medium stores a computer program or instructions. When the computer program or the instructions are run on a computer, the computer is enabled to perform the information processing method according to any one of the second aspect or the possible implementations of the second aspect.

According to a thirteenth aspect, an embodiment of this application provides a computer-readable storage medium. The computer-readable storage medium stores a computer program or instructions. When the computer program or the instructions are run on a computer, the computer is enabled to perform the information processing method according to any one of the third aspect or the possible implementations of the third aspect.

According to a fourteenth aspect, an embodiment of this application provides a computer-readable storage medium. The computer-readable storage medium stores a computer program or instructions. When the computer program or the instructions are run on a computer, the computer is enabled to perform the information processing method according to any one of the seventh aspect or the possible implementations of the seventh aspect.

According to a fifteenth aspect, an embodiment of this application provides a computer-readable storage medium. The computer-readable storage medium stores a computer program or instructions. When the computer program or the instructions are run on a computer, the computer is enabled to perform the information processing method according to any one of the eighth aspect or the possible implementations of the eighth aspect.

According to a sixteenth aspect, an embodiment of this application provides a computer program product including instructions. When the instructions are run on a computer, the computer is enabled to perform the information processing method in the first aspect or the possible implementations of the first aspect.

According to a seventeenth aspect, this application provides a computer program product including instructions. When the instructions are run on a computer, the computer is enabled to perform the information processing method in the second aspect or the possible implementations of the second aspect.

According to an eighteenth aspect, an embodiment of this application provides a computer program product including instructions. When the instructions are run on a computer, the computer is enabled to perform the information processing method in the third aspect or the possible implementations of the third aspect.

According to a nineteenth aspect, this application provides a computer program product including instructions. When the instructions are run on a computer, the computer is enabled to perform the information processing method in the seventh aspect or the possible implementations of the seventh aspect.

According to a twentieth aspect, an embodiment of this application provides a computer program product including instructions. When the instructions are run on a computer, the computer is enabled to perform the information processing method in the eighth aspect or the possible implementations of the eighth aspect.

According to a twenty-first aspect, an embodiment of this application provides an information processing apparatus, configured to implement the methods in the possible designs of any one of the first aspect to the third aspect, the seventh aspect, or the eighth aspect. The information processing apparatus may be the foregoing first data analytics network element, an apparatus including the foregoing first data analytics network element, or a component (for example, a chip) used in the first data analytics network element. Alternatively, the information processing apparatus may be the foregoing first network element, an apparatus including the foregoing first network element, or a component (for example, a chip) used in the foregoing first network element. The information processing apparatus may be the foregoing second data analytics network element, an apparatus including the foregoing second data analytics network element, or a component (for example, a chip) used in the second data analytics network element. The information processing apparatus includes a corresponding module and unit for implementing the foregoing method. The module and the unit may be implemented by hardware or software, or by hardware executing corresponding software. The hardware or the software includes one or more modules or units corresponding to the foregoing functions.

According to a twenty-second aspect, an embodiment of this application provides an information processing apparatus. The information processing apparatus includes at least one processor and a communication interface. When the information processing apparatus runs, the processor executes computer-executable instructions or a program stored in the information processing apparatus, so that the information processing apparatus performs the method according to any one of the possible designs of the first aspect. For example, the information processing apparatus may be a first network element or a component used in the first network element.

According to a twenty-third aspect, an embodiment of this application provides an information processing apparatus. The information processing apparatus includes at least one processor and a communication interface. When the information processing apparatus runs, the processor executes computer-executable instructions or a program stored in the information processing apparatus, so that the information processing apparatus performs the method according to any one of the possible designs of the second aspect. For example, the information processing apparatus may be a first data analytics network element or a component used in the first data analytics network element.

According to a twenty-fourth aspect, an embodiment of this application provides an information processing apparatus. The information processing apparatus includes at least one processor and a communication interface. When the information processing apparatus runs, the processor executes computer-executable instructions or a program stored in the information processing apparatus, so that the information processing apparatus performs the method according to any one of the possible designs of the third aspect. For example, the information processing apparatus may be a second data analytics network element or a component used in the second data analytics network element.

According to a twenty-fifth aspect, an embodiment of this application provides an information processing apparatus. The information processing apparatus includes at least one processor and a communication interface. When the information processing apparatus runs, the processor executes computer-executable instructions or a program stored in the information processing apparatus, so that the information processing apparatus performs the method according to any one of the possible designs of the seventh aspect. For example, the information processing apparatus may be a first data analytics network element or a component used in the first data analytics network element.

According to a twenty-sixth aspect, an embodiment of this application provides an information processing apparatus. The information processing apparatus includes at least one processor and a communication interface. When the information processing apparatus runs, the processor executes computer-executable instructions or a program stored in the information processing apparatus, so that the information processing apparatus performs the method according to any one of the possible designs of the eighth aspect. For example, the information processing apparatus may be a first network element or a component used in the first network element.

It should be understood that the information processing apparatus in the twenty-second aspect to the twenty-sixth aspect may further include a bus and a memory. The memory is configured to store code and data. Optionally, the at least one processor, the communication interface, and the memory are coupled to each other.

According to a twenty-seventh aspect, an embodiment of this application provides an information processing apparatus, including at least one processor. When the information processing apparatus runs, the at least one processor executes computer-executable instructions or a program stored in a memory, so that the information processing apparatus performs the method according to any one of the first aspect or the possible designs of the first aspect. For example, the information processing apparatus may be a first network element or a chip used in the first network element.

According to a twenty-eighth aspect, an embodiment of this application provides an information processing apparatus, including at least one processor. When the information processing apparatus runs, the at least one processor executes computer-executable instructions or a program stored in a memory, so that the information processing apparatus performs the method according to any one of the second aspect or the possible designs of the second aspect. For example, the information processing apparatus may be a first data analytics network element or a chip used in the first data analytics network element.

According to a twenty-ninth aspect, an embodiment of this application provides an information processing apparatus, including at least one processor. When the information processing apparatus runs, the at least one processor executes computer-executable instructions or a program stored in a memory, so that the information processing apparatus performs the method according to any one of the third aspect or the possible designs of the third aspect. For example, the information processing apparatus may be a second data analytics network element or a chip used in the second data analytics network element.

According to a thirtieth aspect, an embodiment of this application provides an information processing apparatus, including at least one processor. When the information processing apparatus runs, the at least one processor executes computer-executable instructions or a program stored in a memory, so that the information processing apparatus performs the method according to any one of the seventh aspect or the possible designs of the seventh aspect. For example, the information processing apparatus may be a first data analytics network element or a chip used in the first data analytics network element.

According to a thirty-first aspect, an embodiment of this application provides an information processing apparatus, including at least one processor. When the information processing apparatus runs, the at least one processor executes computer-executable instructions or a program stored in a memory, so that the information processing apparatus performs the method according to any one of the eighth aspect or the possible designs of the eighth aspect. For example, the information processing apparatus may be a first network element or a chip used in the first network element.

According to a thirty-second aspect, an embodiment of this application provides an information processing apparatus. The information processing apparatus includes a processor and a storage medium. The storage medium stores instructions. When the instructions are run by the processor, the information processing method in the first aspect or the possible implementations of the first aspect is implemented.

According to a thirty-third aspect, an embodiment of this application provides an information processing apparatus. The information processing apparatus includes a processor and a storage medium. The storage medium stores instructions. When the instructions are run by the processor, the information processing method in the second aspect or the possible implementations of the second aspect is implemented.

According to a thirty-fourth aspect, an embodiment of this application provides an information processing apparatus. The information processing apparatus includes a processor and a storage medium. The storage medium stores instructions. When the instructions are run by the processor, the information processing method in the third aspect or the possible implementations of the third aspect is implemented.

According to a thirty-fifth aspect, an embodiment of this application provides an information processing apparatus. The information processing apparatus includes a processor and a storage medium. The storage medium stores instructions. When the instructions are run by the processor, the information processing method in the seventh aspect or the possible implementations of the seventh aspect is implemented.

According to a thirty-sixth aspect, an embodiment of this application provides an information processing apparatus. The information processing apparatus includes a processor and a storage medium. The storage medium stores instructions. When the instructions are run by the processor, the information processing method in the eighth aspect or the possible implementations of the eighth aspect is implemented.

According to a thirty-seventh aspect, an embodiment of this application provides an information processing apparatus. The information processing apparatus includes one or more modules, configured to implement the method according to any one of the first aspect, the second aspect, the third aspect, the seventh aspect, or the eighth aspect. The one or more modules may correspond to steps in the method according to any one of the first aspect, the second aspect, the third aspect, the seventh aspect, or the eighth aspect.

According to a thirty-eighth aspect, an embodiment of this application provides a chip. The chip includes a processor and a communication interface. The communication interface is coupled to the processor. The processor is configured to run a computer program or instructions, to implement the information processing method in the first aspect or the possible implementations of the first aspect. The communication interface is configured to communicate with a module other than the chip.

According to a thirty-ninth aspect, an embodiment of this application provides a chip. The chip includes a processor and a communication interface. The communication interface is coupled to the processor. The processor is configured to run a computer program or instructions, to implement the information processing method in the second aspect or the possible implementations of the second aspect. The communication interface is configured to communicate with a module other than the chip.

According to a fortieth aspect, an embodiment of this application provides a chip. The chip includes a processor and a communication interface. The communication interface is coupled to the processor. The processor is configured to run a computer program or instructions, to implement the information processing method in the third aspect or the possible implementations of the third aspect. The communication interface is configured to communicate with a module other than the chip.

According to a forty-first aspect, an embodiment of this application provides a chip. The chip includes a processor and a communication interface. The communication interface is coupled to the processor. The processor is configured to run a computer program or instructions, to implement the information processing method in the seventh aspect or the possible implementations of the seventh aspect. The communication interface is configured to communicate with a module other than the chip.

According to a forty-second aspect, an embodiment of this application provides a chip. The chip includes a processor and a communication interface. The communication interface is coupled to the processor. The processor is configured to run a computer program or instructions, to implement the information processing method in the eighth aspect or the possible implementations of the eighth aspect. The communication interface is configured to communicate with a module other than the chip.

Specifically, the chip provided in embodiments of this application further includes a memory, configured to store the computer program or the instructions.

According to a forty-third aspect, an embodiment of this application provides a communication system. The communication system includes the information processing apparatus according to any one of the fourth aspect or the possible implementations of the fourth aspect and the information processing apparatus according to any one of the fifth aspect or the possible implementations of the fifth aspect.

In a possible implementation, the communication system may further include the information processing apparatus according to any one of the sixth aspect or the possible implementations of the sixth aspect.

According to a forty-fourth aspect, an embodiment of this application provides a communication system. The communication system includes the information processing apparatus according to any one of the ninth aspect or the possible implementations of the ninth aspect and the information processing apparatus according to any one of the tenth aspect or the possible implementations of the tenth aspect.

Any apparatus, computer storage medium, computer program product, chip, or communication system provided above is configured to perform the corresponding method provided above. Therefore, for beneficial effects that can be achieved by the apparatus, computer storage medium, computer program product, chip, or communication system provided above, refer to the beneficial effects of the corresponding solution in the corresponding method provided above. Details are not described herein again.

DESCRIPTION OF EMBODIMENTS

Figure 1:
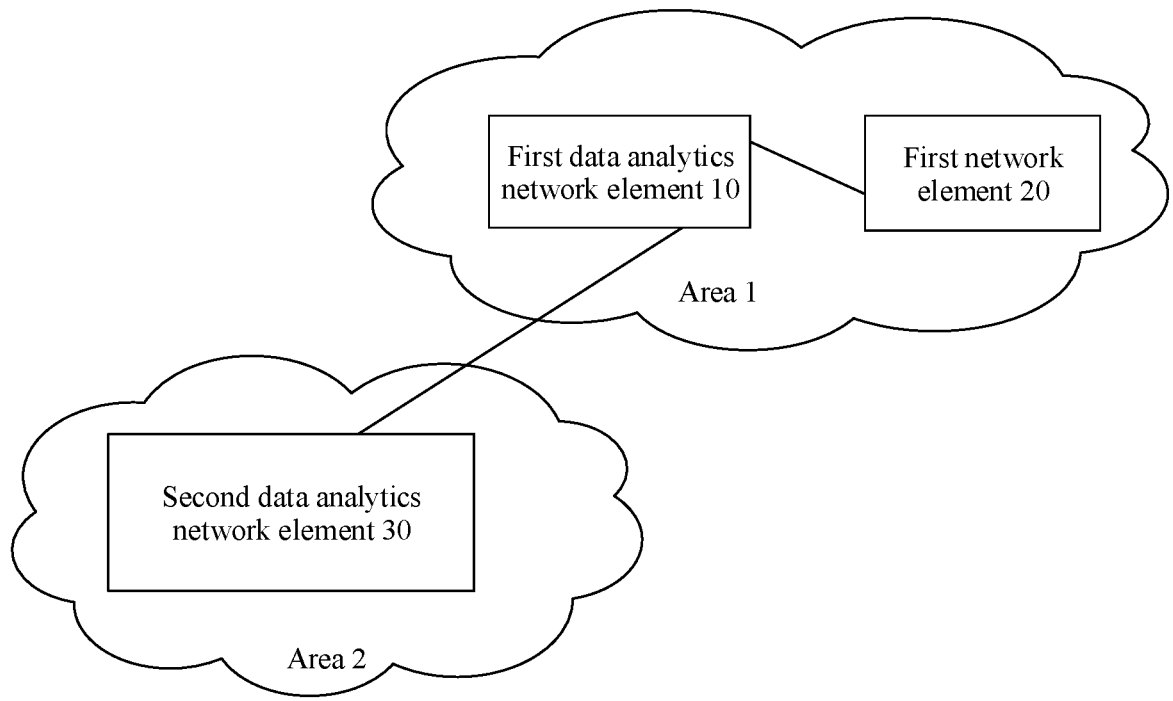
FIG. 1 is a schematic diagram of an architecture of a communication system according to an embodiment of this application.

To clearly describe the technical solutions in embodiments of this application, terms such as "first" and "second" are used in embodiments of this application to distinguish between same items or similar items that have basically same functions and effects. For example, a first terminal and a second terminal are merely intended to distinguish between different terminals, and are not intended to limit a sequence thereof. A person skilled in the art may understand that the terms such as "first" and "second" do not limit a quantity or an execution sequence, and the terms such as "first" and "second" do not indicate a definite difference.

It should be noted that, in this application, the word such as "exemplary" or "for example" is for representing giving an example, an illustration, or a description. Any embodiment or design scheme described as an "exemplary" or "for example" in this application should not be explained as being more preferred or having more advantages than another embodiment or design scheme. Exactly, use of the word such as "exemplary" or "for example" is intended to present a related concept in a specific manner.

A network architecture and a service scenario that are described in embodiments of this application are intended to describe the technical solutions in embodiments of this application more clearly, and do not constitute a limitation on the technical solutions provided in embodiments of this application. A person of ordinary skill in the art may know that with evolution of the network architecture and emergence of a new service scenario, the technical solutions provided in embodiments of this application are also applicable to similar technical problems.

In this application, "at least one" refers to one or more, and "a plurality of" refers to two or more. "And/or" describes an association relationship between associated objects, and represents that three relationships may exist. For example, A and/or B may represent the following cases: Only A exists, both A and B exist, and only B exists, where A and B may be singular or plural. The character "/" generally indicates an "or" relationship between the associated objects. "At least one of the following items" or a similar expression thereof indicates any combination of the items, and includes a singular item or any combination of plural items. For example, at least one of a, b, or c may indicate: a, b, c, a and b, a and c, b and c, or a, b, and c, where a, b, and c may be singular or plural.

Steps in an information processing method provided in embodiments of this application are merely examples. Not all steps are mandatory, or not all content in each piece of information or each message is mandatory. The steps or the content may be added or reduced as required in a use process.

A same step or a step or a message having a same function in embodiments of this application may be mutually referenced in different embodiments.

A system architecture and the service scenario that are described in embodiments of this application are intended to describe the technical solutions in embodiments of this application more clearly, and do not constitute a limitation on the technical solutions provided in embodiments of this application. A person of ordinary skill in the art may know that with the evolution of the network architecture and the emergence of the new service scenario, the technical solutions provided in embodiments of this application are also applicable to the similar technical problems. In embodiments of this application, an example in which the provided method is applied to an NR system or a 5G network is used for description.

FIG. 1 shows a communication system according to an embodiment of this application. The system includes a first data analytics network element 10 and a first network element 20 that communicates with the first data analytics network element 10.

The first data analytics network element 10 may indirectly communicate with the first network element 20. For example, the first data analytics network element 10 communicates with the first network element 20 through an intermediate network element. For example, an intermediate network element in a 5G system may be a network exposure function ( ) network element.

For example, the first network element 20 in this embodiment of this application may be an application function network element or a network function (NF) network element. For example, the NF network element may be a mobility management network element or a session management network element.

In a possible implementation, as shown in FIG. 1, the communication system may further include a second data analytics network element 30. The first data analytics network element 10 and the second data analytics network element 30 serve different areas. For example, as shown in FIG. 1, the second data analytics network element 30 serves an area 2, and the first data analytics network element 10 and the first network element 20 serve an area 1.

A plurality of data analytics network elements (for example, the first data analytics network element 10 and the second data analytics network element 30) may be deployed in the communication system shown in FIG. 1, and different data analytics network elements in the plurality of data analytics network elements serve different areas. In addition, the different data analytics network elements may also have respective analytics types for which the different data analytics network elements are responsible. For example, some data analytics network elements specifically provide analytics of load of a network function, moving trajectory information of a terminal, and service experience. Some data analytics network elements have a function of supporting analytics of an emergency event or a public safety event. In addition, some data analytics network elements are responsible for associated network data analytics work in the area 1. Some other data analytics network elements are responsible for data analytics work in the area 2.

In an implementation, a data analytics network element in this embodiment of this application may be separately deployed or independently deployed as a network element. Certainly, the data analytics network element may alternatively be integrated into a network function (NF) network element. That is, the data analytics network element may be included in the NF network element as a module. In other words, the NF network element has a function of the data analytics network element. Certainly, the data analytics network element may alternatively be deployed in a same device with another NF network element. This is not limited in this embodiment of this application. For example, the data analytics network element may be co-located with a session management network element or a mobility management network element.

In a possible implementation, the plurality of data analytics network elements may be further deployed hierarchically. For example, one central data analytics network element is deployed in a public land mobile network (PLMN) of an entire country, and edge data analytics network elements are deployed in different provinces and cities. For example, the first data analytics network element 10 may be a central data analytics network element. The second data analytics network element 30 may be an edge data analytics network element. Alternatively, the first data analytics network element 10 and the second data analytics network element 30 are edge data analytics network elements in different provinces and cities.

If the foregoing communication system is used in an evolved packet core (EPC), a network element or an entity corresponding to the mobility management network element or the session management network element may be a mobility management entity (MME). In other words, in a 4G core network, the MME has both a session management function and a mobility management function. A data analytics network element may also be referred to as a network data analytics network element in the 4G core network.

If the foregoing communication system is used in a 5G network, a network element or an entity corresponding to the mobility management network element may be an access and mobility management function (AMF) network element, and a network element or an entity corresponding to the session management network element may be a session management function (SMF) network element. A network element or an entity corresponding to the application function network element may be an application function (AF) network element. In the 5G network, the data analytics network element in this embodiment of this application may be a network data analytics function (NWDAF) network element in a 5GC, may be a management data analytics service (MDAS) of network management, or may even be a data analytics network element or a data analytics entity on a radio access network (RAN) side.

Figure 2:
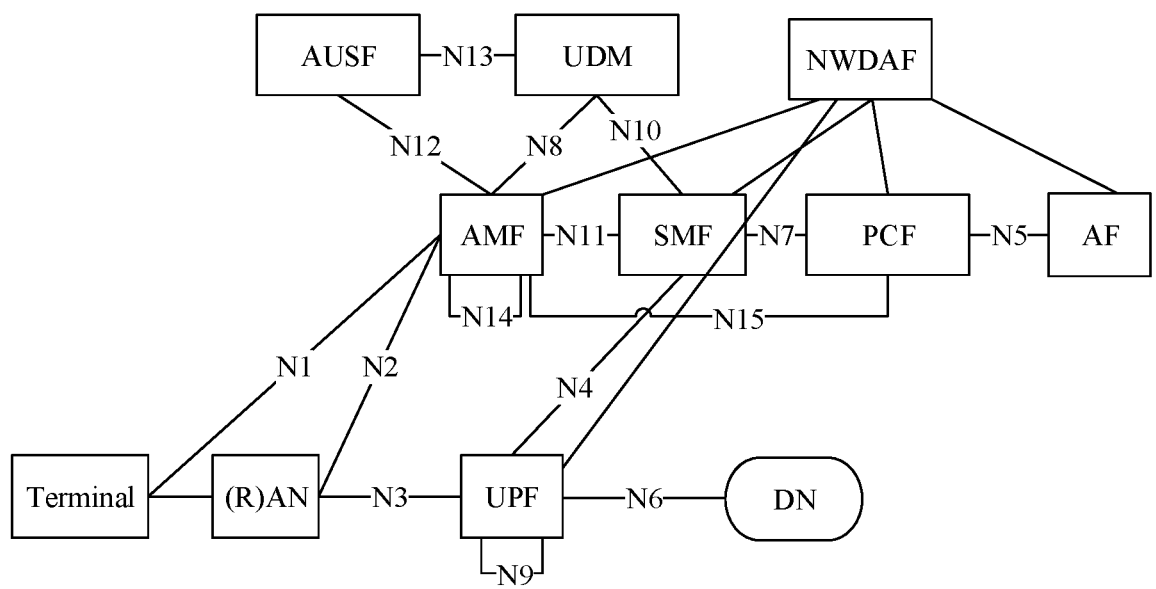
FIG. 2 is a diagram of a 5G network architecture according to an embodiment of this application.

As shown in FIG. 2, in addition to including the foregoing core network elements, the 5G network may further include a (radio) access network ((R) AN), a user plane function (UPF) network element, a policy control function (PCF) network element, an authentication server function (AUSF) network element, a network slice selection function (NSSF) network element, a network exposure function (NEF) network element, a user data repository (UDR), a unified data management (UDM) network element, and data network (DN) A network repository function (NRF) network element is mainly configured to discover a network element.

A terminal communicates with the AMF network element through an N1 interface (N1 for short). The AMF network element communicates with the SMF network element through an N11 interface (N11 for short). The SMF network element communicates with one or more UPF network elements through an N4 interface (N4 for short). Any two of the one or more UPF network elements communicate with each other through an N9 interface (N9 for short). The UPF network element communicates, through an N6 interface (N6 for short), with the data network (DN) managed and controlled by the AF network element. The terminal accesses a 5G core network (5GC) through the (R)AN. The (R)AN communicates with the AMF network element through an N2 interface (N2 for short). The SMF network element communicates with the PCF network element through an N7 interface (N7 for short). The PCF network element communicates with the AF network element through an N5 interface. The (R)AN communicates with the UPF network element through an N3 interface (N3 for short). Any two AMF network elements communicate with each other through an N14 interface (N14 for short). The SMF network element communicates with the UDM through an N10 interface (N10 for short). The AMF network element communicates with the AUSF through an N12 interface (N12 for short). The AUSF network element communicates with the UDM network element through an N13 interface (N13 for short). The AMF network element communicates with the UDM network element through an N8 interface (N8 for short).

It should be understood that, in the network architecture shown in FIG. 2, control plane network elements in the 5G core network (5GC) may alternatively interact with each other through a service based interface. For example, in FIG. 3, an AMF network element, an SMF network element, a UDM network element, or a PCF network element uses a service based interface for interaction. For example, an external service based interface provided by the AMF network element may be Namf. An external service based interface provided by the SMF network element may be Nsmf. An external service based interface provided by the UDM network element may be Nudm. An external service based interface provided by the PCF network element may be Npcf. It should be understood that for related descriptions of names of various service based interfaces, refer to a diagram of a 5G system architecture in a conventional technology. Details are not described herein.

Figure 3:
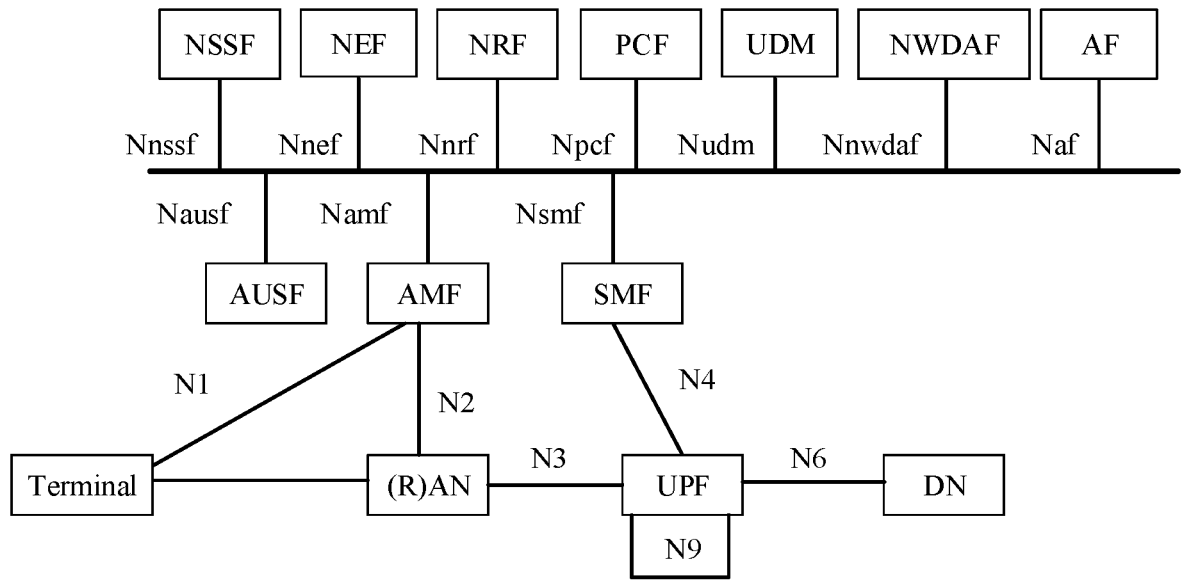
FIG. 3 is a diagram of another 5G network architecture according to an embodiment of this application.

It should be noted that FIG. 2 or FIG. 3 merely shows, for example, one UPF network element and one SMF network element. Certainly, the figure may include a plurality of UPF network elements and a plurality of SMF network elements, for example, include an SMF network element 1 and an SMF network element 2. This is not specifically limited in embodiments of this application.

In a possible implementation, in addition to the functional units shown in FIG. 2 or FIG. 3, the system may further include another functional network element, for example, an operation and management (O&M) network element. This is not limited in this embodiment of this application. In addition, names of the devices in FIG. 2 or FIG. 3 are not limited. The devices may alternatively have other names in addition to the names shown in FIG. 2 or FIG. 3. For example, the names are replaced with names of network elements having same or similar functions. This is not limited.

It should be noted that the (R)AN, the AMF network element, the SMF network element, the UDM network element, the UPF network element, the PCF network element, the authentication server function (AUSF) network element, and the like in FIG. 2 or FIG. 3 are merely names, and the names do not constitute a limitation on the devices. In the 5G network and another future network, network elements or entities corresponding to the (R)AN, the AMF network element, the SMF network element, the UDM network element, the UPF network element, and the PCF network element may alternatively have other names. This is not specifically limited in embodiments of this application. For example, the UDM network element may alternatively be replaced with a home subscriber server (HSS), a user subscription database (USD), a database entity, or the like. This is uniformly described herein. Details are not described subsequently again.

The following separately describes functions of each part or network element in the network architectures in the 5G network by using examples.

The terminal includes but is not limited to user equipment (UE), a subscriber unit, a subscriber station, a mobile station, a remote station, a remote terminal device, a mobile terminal device, a user terminal device, a wireless communication device, a user agent, a user apparatus, a cellular phone, a cordless phone, a session initiation protocol (SIP) phone, a wireless local loop (WLL) station, a personal digital assistant (PDA), a handheld device with a wireless communication function, a computing device, a processing device connected to a wireless modem, a vehicle-mounted device, a wearable device, a terminal device in an internet of things, a household appliance, a virtual reality device, a terminal device in the future 5G network, a terminal device in a future evolved public land mobile network (PLMN), or the like.

The AMF network element is configured to provide functions such as mobility management, lawful interception, or access authorization and authentication for the terminal. For example, the AMF network element may further provide location information of the terminal and an identifier of the terminal for a data analytics network element.

AF network elements may be classified into an operator AF network element and a third-party AF network element. A difference lies in whether an AF network element is deployed by an operator. The third-party AF network element includes various application-associated servers that are not deployed by the operator, for example, an AF network element associated with a railway system (for example, an associated AF network element configured to purchase a ticket), an AF network element associated with a medical system (for example, Haodaifu Online), and an AF associated with an OTT service (for example, Alipay), and an AF associated with a government community (such as a community service app).

The NEF network element is configured to expose data and a service of a communication operator network to an external AF network element, or expose data or a service provided by the AF network element to the operator.

The NRF network element is configured to store capability, a service, and status information of a network element, and may be further used by a network element to search for and discover another network element.

The NWDAF network element has data collection, training, analytics, and reasoning functions, and may be configured to: collect terminal-associated data from a network function, a third-party service server, a terminal, or a network management system, perform analytics and training based on the associated data, and provide a data analytics result for the network function, the third-party service server, the terminal, or the network management system. The data analytics result may assist a network in selecting a quality of service parameter of a service, assist the network in performing traffic routing, assist the network in selecting a background traffic transmission policy, or the like. Embodiments of this application mainly involve the data collection function of the NWDAF. Because the NWDAF may execute associated training and analytics functions based on the collected data, a prerequisite is that the associated data can be collected and obtained. In embodiments of this application, NWDAFs may be classified into a third NWDAF and an NWDAF that supports an emergency event. The NWDAF that supports the emergency event may mean that the NWDAF supports an emergency event (for example, an emergency epidemic or a public safety event) analytics function, for example, is configured to obtain a mapping relationship between the terminal and the emergency event. The third NWDAF does not have the emergency event (for example, the emergency epidemic or the public safety event) analytics function, but can collect and obtain the associated data, for example, analyze a moving trajectory of the terminal.

Another NF (a data provider) usually refers to a node or a physical device in the network, provides corresponding function support for network access, session management, authentication, policy control, and the like, of the terminal, and also generates corresponding network data. For example, the AMF network element, the SMF network element, and the UDM network element are all examples of the NF network element.

Figure 4:
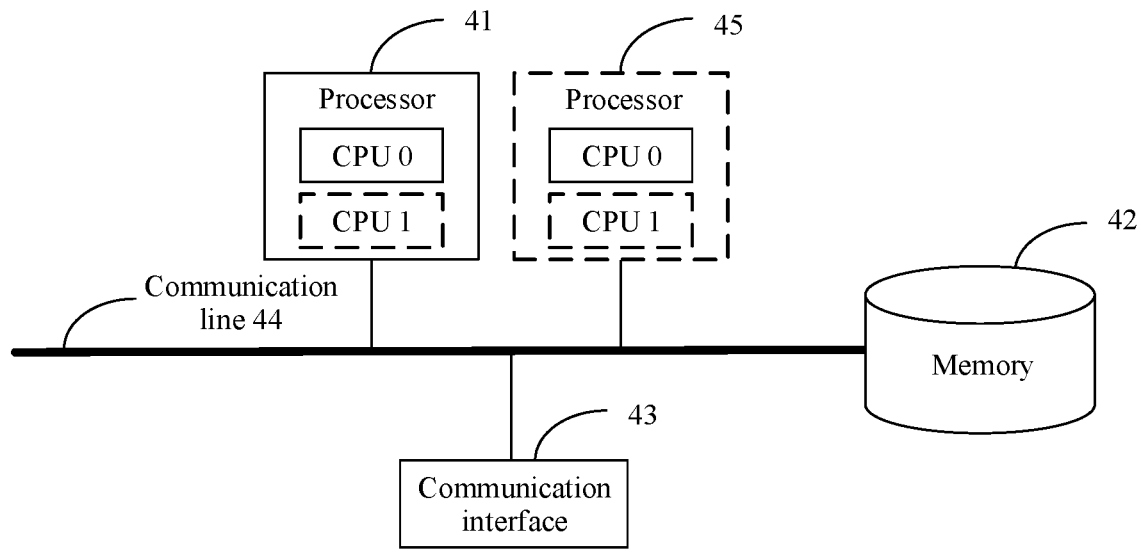
FIG. 4 is a schematic diagram of a structure of a communication device according to an embodiment of this application.

FIG. 4 is a schematic diagram of a structure of a communication device according to an embodiment of this application. For structures of all of the first data analytics network element 10, the second data analytics network element 30, and the first network element 20 in embodiments of this application, refer to the schematic diagram of the structure of the communication device shown in FIG. 4. The communication device includes at least one processor 41, a communication line 44, and at least one communication interface (a communication interface 43 is used as an example for description in FIG. 4).

The processor 41 may be a general-purpose central processing unit (CPU), a microprocessor, an application-specific integrated circuit (ASIC), or one or more integrated circuits configured to control program execution of the solutions in this application.

The communication line 44 may include a path for transferring information between the foregoing components.

The communication interface 43 is configured to exchange information with another apparatus. For example, the communication interface 43 is any apparatus such as a transceiver, and is configured to communicate with another device or a communication network such as the Ethernet, a radio access network (RAN), or a wireless local area network (WLAN).

Optionally, the communication device may further include a memory 42. The memory 42 may be a read-only memory (ROM) or another type of static storage device that can store static information and instructions, or a random access memory (RAM) or another type of dynamic storage device that can store information and instructions, or may be an electrically erasable programmable read-only memory (EEPROM), a compact disc read-only memory (CD-ROM) or another compact disc storage, an optical disc storage (including a compressed optical disc, a laser disc, an optical disc, a digital versatile disc, a Blu-ray disc, or the like), a magnetic disk storage medium or another magnetic storage device, or any other medium that can be for carrying or storing expected program code in a form of instructions or a data structure and that can be accessed by a computer. However, the memory 42 is not limited thereto. The memory may exist independently, and is connected to the processor through the communication line 44. Alternatively, the memory may be integrated with the processor.

The memory 42 is configured to store computer-executable instructions for executing the solutions in this application, and the execution is controlled by the processor 41. The processor 41 is configured to execute the computer-executable instructions stored in the memory 42, to implement the information processing method provided in the following embodiments of this application.

Optionally, the computer-executable instructions in this embodiment of this application may also be referred to as application program code. This is not specifically limited in this embodiment of this application.

During specific implementation, in an embodiment, the processor 41 may include one or more CPUs such as a CPU 0 and a CPU 1 in FIG. 4.

During specific implementation, in an embodiment, the communication device may include a plurality of processors such as the processor 41 and a processor 45 in FIG. 4. Each of the processors may be a single-core (single-CPU) processor, or may be a multi-core (multi-CPU) processor. The processor herein may be one or more devices, circuits, and/or processing cores configured to process data (for example, computer program instructions).

In embodiments of this application, a specific structure of an execution body of the information processing method is not particularly limited in embodiments of this application, provided that communication may be performed according to the information processing method in embodiments of this application by running a program that records code of the information processing method in embodiments of this application. For example, the execution body of the information processing method provided in embodiments of this application may be the first data analytics network element 10, or a part, for example, a chip, used in the first data analytics network element 10. This is not limited in this application. Alternatively, the execution body of the information processing method provided in embodiments of this application may be the first network element 20, or a part, for example, a chip, used in the first network element 20. This is not limited in this application. In the following embodiments, descriptions are provided by using examples in which execution bodies of the information processing method are the first data analytics network element 10 and the first network element 20.

Figure 5:
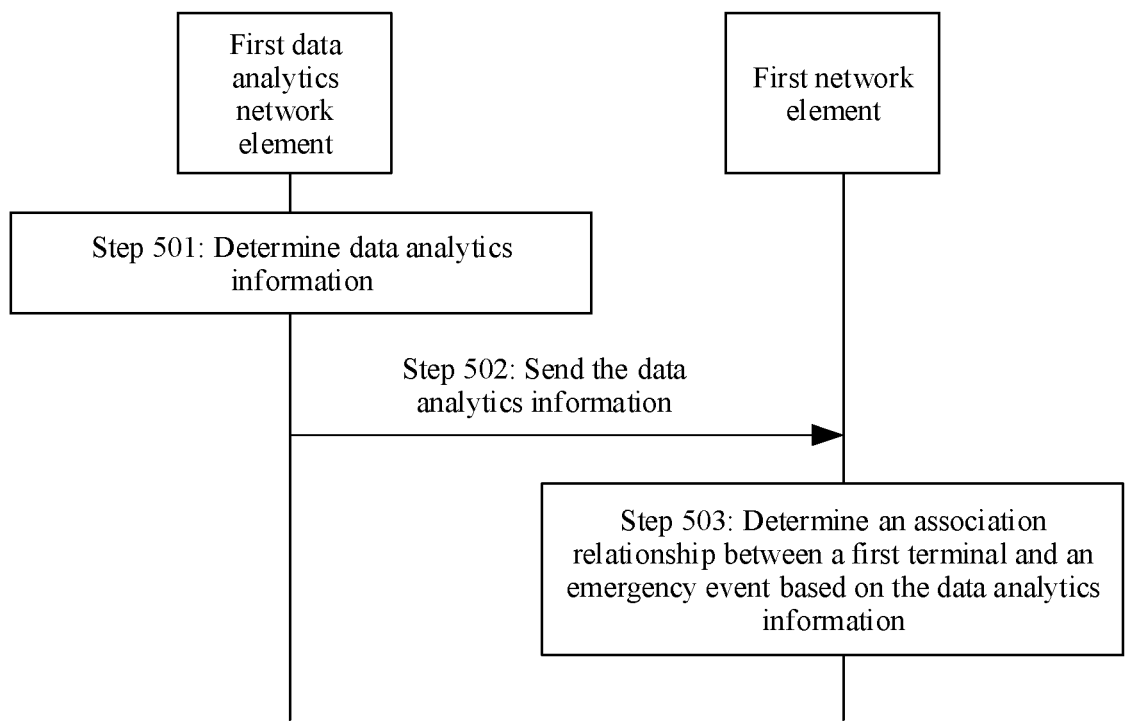
FIG. 5 is a schematic flowchart of an information processing method according to an embodiment of this application.

FIG. 5 shows an interaction embodiment of an information processing method according to an embodiment of this application. The method includes the following steps.

Step 501: A first data analytics network element 10 determines data analytics information, where the data analytics information includes one or more of the following information: an identifier of a first terminal, activity degree information of the first terminal, moving trajectory information of the first terminal, and first risk information of the first terminal.

For example, the identifier of the first terminal in this embodiment of this application may be the identifier of the first terminal, or may be information about a user of the first terminal. For example, the information about the user of the first terminal may be identity information of a user who registers a SIM card or an eSIM card in the first terminal, may be information about an identification card or a passport of the user in social life, or may be information about an application identity used when the user uses an application. This is not limited in this embodiment of this application. An identifier of a terminal in this embodiment of this application may be one or more of the following: an internet protocol (IP) address, a subscription permanent identifier (SUPI), a permanent equipment identifier (PEI), a generic public subscription identifier (GPSI), an international mobile subscriber identifier (IMSI), an international mobile equipment identity (IMEI), an IP 5-tuple (5-tuple), and a mobile subscriber integrated services digital network number (MSISDN). For an identifier of a terminal in the following embodiments, refer to the descriptions herein. Details are not described subsequently again.

The first terminal in this embodiment of this application may represent one or more terminals.

In an implementation, the first terminal is a terminal that is associated with an emergency event and that is determined by the first data analytics network element 10.

In another implementation, the first terminal is a terminal associated with information about a target area and information about target time, for example, a terminal that resided during a target period in a network corresponding to the target area.

The first data analytics network element 10 in this embodiment of this application may actively determine the data analytics information. Certainly, the first data analytics network element 10 may determine the data analytics information when the emergency event occurs. Alternatively, the first data analytics network element 10 may determine the data analytics information due to triggering of another network element (for example, a first network element 20). This is not limited in this embodiment of this application. For a manner in which the first data analytics network element 10 determines the data analytics information due to triggering of the another network element (for example, the first network element 20), refer to descriptions of step 601 and step 602 in the following embodiment. Details are not described herein again.

That the first data analytics network element 10 in this embodiment of this application determines that the emergency event occurs may be implemented in the following manner: The first data analytics network element 10 determines, based on emergency indication information, that the emergency event occurs. The emergency indication information may be provided by the first network element 20 for the first data analytics network element 10. Certainly, the emergency indication information may alternatively be provided by a network element other than the first network element 20 for the first data analytics network element 10. This is not limited in this embodiment of this application. The emergency indication information indicates that the emergency event occurs.

In a possible example, the activity degree information of the first terminal in this embodiment of this application is information for representing a mobility degree or a communication degree of the first terminal in a network. For example, the activity degree information of the first terminal may be a specific value. When a terminal with a high value corresponding to activity degree information is compared with a terminal with a low value corresponding to activity degree information, a higher value represents a higher mobility degree or communication degree of the terminal in the network. Alternatively, the activity degree information of the first terminal may be represented by a level, for example, "high", "moderate", or "low". Alternatively, the activity degree information of the first terminal may be one or more of the following information: a quantity of times or frequency of re-registering with the network by the first terminal, a quantity of times or frequency of changing location information (a TA/a cell) of the first terminal, a quantity of times or frequency of entering a location range by the first terminal, and a quantity of services initiated by the first terminal after the first terminal enters the location range or a quantity of times of initiating a service by the first terminal after the first terminal enters the location range, for example, Dianping (3 times), a metro app (3 times), and DiDi Dache (twice).

In another possible example, the activity degree information of the first terminal may alternatively be for indirectly reflecting a degree of association between the first terminal and the emergency event. For example, association between a terminal with a high activity degree and the emergency event is greater than association between a terminal with a low activity degree and the emergency event. Correspondingly, a risk degree of the terminal with the high activity degree may be higher than a risk degree of the terminal with the low activity degree. For activity degree information of a terminal below, refer to the descriptions herein. Details are not described subsequently again.

In this embodiment of this application, the activity degree information of the terminal may be calculated with reference to the following manners. For example, one or more of the following information is used as input data to calculate the activity degree information of the terminal: a quantity of times or frequency of re-registering with the network by the terminal, a quantity of times or frequency of changing a location of the terminal, a quantity of times or frequency of entering a location range by the terminal, and a quantity of services initiated by the first terminal after the first terminal enters the location range or a quantity of times of initiating a service by the first terminal after the first terminal enters the location range. For another example, different weight parameters may alternatively be set for different areas. For example, a weight parameter corresponding to a high-risk area is greater than a weight parameter corresponding to a low-risk area. In this way, activity degree information of a user of a terminal that entered and exited the high-risk area is greater than activity degree information of a user of a terminal that did not enter and exit the high-risk area. For another example, different weight parameters may alternatively be set for different services. For example, a weight parameter corresponding to a service 1 is greater than a weight parameter corresponding to a service 2. In this way, activity degree information corresponding to a terminal that used the service 1 is greater than activity degree information corresponding to a terminal that did not use the service 1. Alternatively, activity degree information corresponding to a terminal that used the service 1 is greater than activity degree information corresponding to a terminal that used the service 2.

The moving trajectory information of the first terminal is for determining a location moving trajectory of the first terminal, and may further be for determining time corresponding to the location moving trajectory of the first terminal.

For example, the moving trajectory information of the first terminal includes one or more of the following information of the first terminal: the location information, a time point of entering a location range corresponding to the location information, and stay duration in the location range.

For example, the location information of the first terminal may be for determining a location of the first terminal in the network. For example, the location information of the first terminal includes one or more of the following: a cell identity, a cell identity list, a tracking area (TA) identity, a tracking area identity list, measurement report (MR) location information, and location service (LCS) location information. The LCS location information may be location information provided by a positioning service deployed by an operator. It may be understood that the cell identity list includes one or more cell identities. The tracking area identity list includes one or more tracking area identities. The MR location information is location information that is of the first terminal and that is carried in a measurement report reported by the first terminal.

The stay duration of the first terminal in the location range in this embodiment of this application may be understood as a difference between a time point at which the first terminal enters the location range and a time point at which the first terminal exits the location range.

In a possible implementation, the first risk information of the first terminal includes one or more of the following information of the first terminal: first risk classification information, a first risk degree, and a first risk removal time point.

It may be understood that the first risk classification information of the first terminal may be first risk classification information of the user of the first terminal. The first risk degree of the first terminal may be a first risk degree of the user of the first terminal. The first risk removal time point of the first terminal may be a first risk removal time point of the user of the first terminal.

Risk classification information in this embodiment of this application is for determining a risk classification to which a user belongs, namely, a risk classification of a user of the terminal. For example, the user of the terminal may be classified as a user who is risky or not risky. Alternatively, in this embodiment of this application, the risk classification information may be determined as different risk classifications based on association between users of terminals and the emergency event. For example, the risk classifications include a classification A, a classification B, and a classification C, and association between classifications of different levels and the emergency event is different. For example, the classification A, the classification B, and the classification C indicate that the association between the users and the emergency event decreases gradually. For example, if the risk classification information indicates that the risk classification to which the user belongs is the classification A, it indicates that the user is closely associated with the emergency event. If the risk classification information indicates that the risk classification to which the user belongs is the classification B, it indicates that the user is moderately associated with the emergency event.

A risk degree in this embodiment of this application represents a risk degree of the user that is of the first terminal and that is associated with the emergency event. For example, risk degrees may be defined to include different risk levels. For example, the risk degree may be a high risk, a low risk, a moderate risk, or no risk. The risk degree in this embodiment of this application may be represented by a corresponding identifier. For example, 0 indicates no risk, 1 indicates the low risk, 2 indicates the moderate risk, and 3 indicates the high risk. The risk degree in this embodiment of this application may alternatively be a value, and is represented by using the value. For example, if a risk degree of a user a is 100, and a risk degree of a user b is 120, the risk degree of the user a is higher than the risk degree of the user b. Certainly, in this embodiment of this application, the risk degree may alternatively be compared with a preset risk degree. For example, if a risk degree of a user a is greater than the preset risk degree, the user a may be defined as a high-risk user. For example, if a risk degree of a user b is lower than the preset risk degree, the user b may be defined as a low-risk user.

For subsequent descriptions of risk classification information and a risk degree, refer to the descriptions herein. Details are not described subsequently again.

Step 502: The first data analytics network element 10 sends the data analytics information to the first network element 20. Correspondingly, the first network element 20 receives the data analytics information from the first data analytics network element 10.

In an example, after obtaining the data analytics information, the first data analytics network element 10 in this embodiment of this application may actively send the data analytics information to the first network element 20. In another example, the first data analytics network element 10 in this embodiment of this application may send the data analytics information to the first network element 20 when determining that the emergency event occurs. In still another example, the first data analytics network element 10 may send the data analytics information to the first network element 20 based on a request of the first network element 20. This is not limited in this embodiment of this application.

In this embodiment of this application, when the first network element 20 is a third-party application function (AF) network element, the first data analytics network element 10 may send the data analytics information to the first network element 20 by using an NEF network element. For example, the first data analytics network element 10 sends the data analytics information to the NEF network element, and then the NEF network element sends the data analytics information to the first network element 20. Alternatively, when the first network element 20 is an operator network function network element, the first data analytics network element 10 in this embodiment of this application sends the data analytics information to the first network element 20 by using an interface between the first data analytics network element 10 and the first network element 20. For example, when the first network element 20 is an internal network element (for example, an AMF network element) in a core network, the first data analytics network element 10 may send the data analytics information to the first network element 20 without using an NEF network element.

When the first network element 30 is the third-party AF, before the NEF network element sends the data analytics information to the first network element 20, the NEF network element needs to verify identity information or authorization information of the first network element 20. When the NEF network element determines that the first network element 20 is allowed to obtain the data analytics information associated with the emergency event, the NEF network element sends the data analytics information to the first network element 20. In a manner, the NEF specifically determines, by using emergency indication information provided by the first network element 20 (in a first request message) for the NEF network element, that the first network element 20 is allowed to obtain the data analytics information associated with the emergency event.

Step 503: The first network element 20 determines an association relationship between the first terminal and the emergency event based on the data analytics information.

In one aspect, the association relationship between the first terminal and the emergency event in this embodiment of this application may be understood as an association relationship between the user of the first terminal and the emergency event. In another aspect, the association relationship between the first terminal and the emergency event in this embodiment of this application may be understood as the association relationship between the first terminal and the emergency event.

In an example, step 503 in this embodiment of this application may be implemented in the following manner: The first network element 20 may determine the association relationship between the first terminal and the emergency event based on the data analytics information. For example, when the first terminal included in the data analytics information is a terminal that is associated with the emergency event and that has been determined by the first data analytics network element 10, the first network element 20 determines that the first terminal is associated with the emergency event, and may further determine second risk information of the first terminal based on the activity degree information, first moving trajectory information, and the first risk information that are of the first terminal.

In another example, step 503 in this embodiment of this application may be implemented in the following manner: The first network element 20 determines the association relationship between the first terminal and the emergency event based on the data analytics information and other data (from the first network element 20 or another network element) owned by the first network element 20. For example, if the first terminal in the data analytics information is the terminal corresponding to the information about the target time and the information about the target area, the first network element 20 may determine, based on service data that corresponds to the first terminal and that is obtained by the first network element 20, whether the first terminal is associated with the emergency event. Further, the first network element 20 may further determine second risk information of the first terminal based on the moving trajectory information that is of the first terminal and that is included in the data analytics information in combination with the service data that corresponds to the first terminal and that is stored in the first network element 20.

In the foregoing method, the first data analytics network element 10 provides the data analytics information for the first network element 20. The data analytics information includes one or more of the identifier of the first terminal, the activity degree information of the first terminal, the moving trajectory information of the first terminal, and the first risk information of the first terminal, so that after receiving the data analytics information, the first network element 20 not only can determine the association relationship between the first terminal and the emergency event based on the data analytics information, but also can determine, in time, a risk degree and the moving trajectory information that are of the first terminal. Subsequently, this helps the first network element 20 perform an associated emergency processing operation based on the association relationship between the first terminal and the emergency event.

In a possible implementation, the association relationship in this embodiment of this application includes association indication information and/or the second risk information, where the association indication information indicates whether the first terminal is associated with the emergency event, and the second risk information includes at least one of the following information of the first terminal corresponding to the emergency event: second risk classification information, a second risk degree, and a second risk removal time point.

For example, the association indication information indicates that the user of the first terminal is associated with the emergency event or that the user of the first terminal is not associated with the emergency event. It may also be understood that, if the user of the first terminal is not associated with the emergency event, the second risk information is for determining that the user of the first terminal is not risky. If the association indication information indicates that the user of the first terminal is associated with the emergency event, the first network element 20 may determine, based on the data analytics information, one or more of the second risk classification information, the second risk degree, and the second risk removal time point that are of the first terminal.

It may be understood that, the association relationship between the first terminal and the emergency event in this embodiment of this application may alternatively be determined by the first data analytics network element 10 and then provided for the first network element 20 by using the data analytics information. This is not limited in this embodiment of this application.

The second risk information in this embodiment of this application may be determined based on the first risk information, or the second risk information is determined based on other information (for example, the activity degree information and the moving trajectory information) in the data analytics information. In addition, the second risk information may be the same as or different from the first risk information.

In a possible implementation, the data analytics information in this embodiment of this application is data analytics information corresponding to the information about the target time and the information about the target area. The data analytics information corresponding to the information about the target time and the information about the target area may be understood as data analytics information corresponding to the terminal that resided in the target area during the target period in the network.

In one aspect, the first data analytics network element 10 may further send the information about the target time and/or the information about the target area that correspond/corresponds to the data analytics information to the first network element 20. This helps the first network element 20 determine that the data analytics information is the data analytics information corresponding to the information about the target time and the information about the target area. In another aspect, when the first data analytics network element 10 is triggered, based on the request of the first network element 20, to feed back the data analytics information, the information about the target time and the information about the target area are provided by the first network element 20 for the first data analytics network element 10. In this way, the first data analytics network element 10 can provide, based on the information about the target time and the information about the target area, the data analytics information corresponding to the information about the target time and the information about the target area for the first network element 20.

The information about the target area in this embodiment of this application is for determining the target area. The information about the target area may be geographical area information or network area information corresponding to the target area. This is not limited in this embodiment of this application.

The network area information corresponding to the target area in this embodiment of this application is for determining a network area corresponding to the target area. For example, the network area information may be one or more of the following information: at least one cell identity (Cell ID), at least one tracking area (TA) identity, at least one routing area (RA) identity, at least one piece of MR location information, and at least one piece of LCS location information. The geographical area information identifies a physical area corresponding to the target area. For example, the geographical area information may be one or more of the following information: at least one piece of global positioning system (GPS) location information, at least one piece of national administrative area location information, and at least one piece of longitude and latitude location information.

In a possible implementation, time information includes one or more of the following information: a time point, a time window, a time interval, and a time period.

For network area information, time information, and geographical area information in the following embodiments, refer to the descriptions herein. Details are not described subsequently again.

Figure 6:
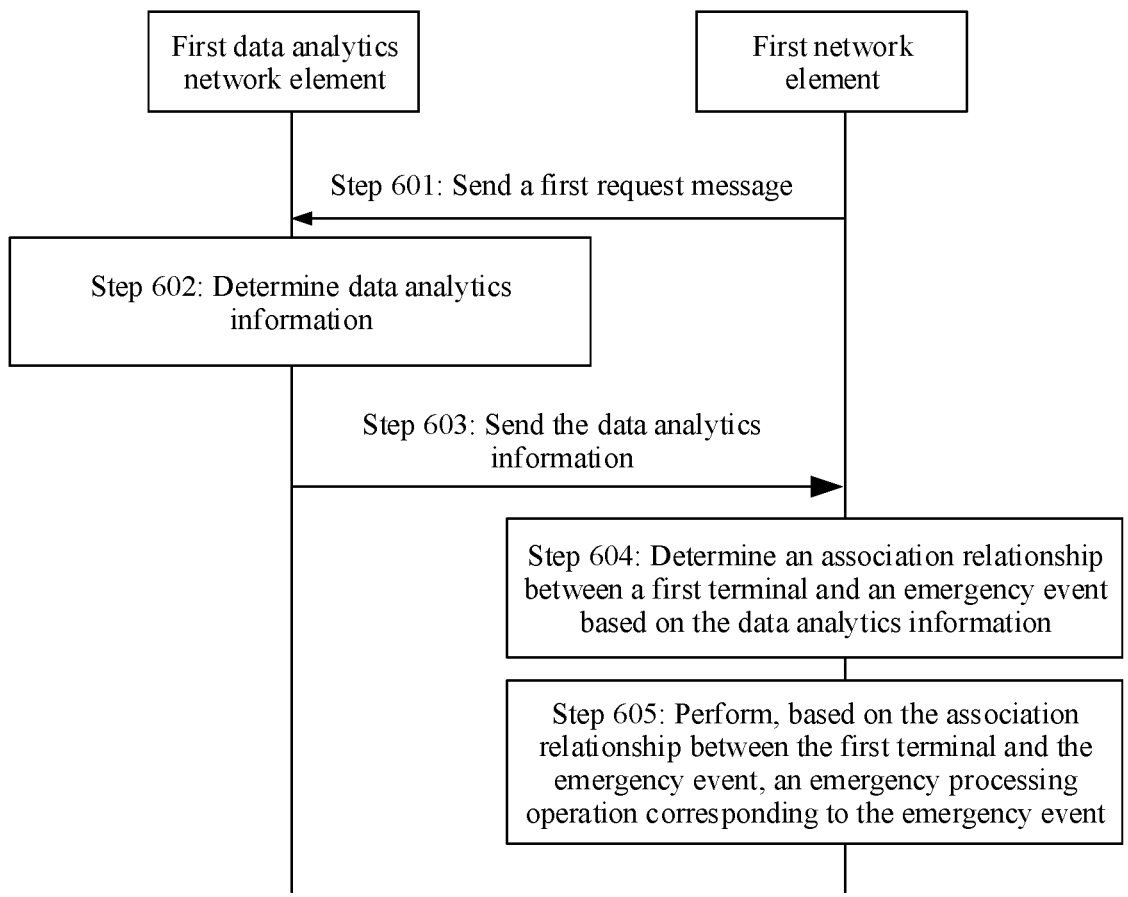
FIG. 6 is a schematic flowchart of an information processing method according to an embodiment of this application.

FIG. 6 shows another embodiment of this application. The method includes step 601 to step 604. Step 602 is the same as step 501, step 603 is the same as step 502, and step 604 is the same as step 503. A difference between the embodiment shown in FIG. 6 and the embodiment shown in FIG. 5 lies in that step 601 may be further included before step 602.

Step 601: A first network element 20 sends a first request message to a first data analytics network element 10. Correspondingly, the first data analytics network element 10 receives the first request message from the first network element 20.

The first request message requests data analytics information. For example, the first request message includes indication information x, and the indication information x requests the data analytics information.

In an example, the first request message includes information about target time and/or information about a target area, and the first request message requests data analytics information corresponding to the information about the target time and/or the information about the target area. For example, the first request message requests data analytics information corresponding to a terminal that resided in a network in the target area at a time point indicated by the information about the target time or in a time period indicated by the information about the target time.

The information that is about the target area and that is carried in the first request message may be geographical area information corresponding to the target area or network area information corresponding to the target area. This is not limited in this embodiment of this application. If the information that is about the target area and that is carried in the first request message may be the geographical area information corresponding to the target area, an NEF network element may convert the geographical area information corresponding to the target area into the network area information corresponding to the target area, and then the NEF network element forwards the first request message to the first data analytics network element 10. Certainly, if the first data analytics network element 10 has a function of identifying the geographical area information corresponding to the target area, or the first data analytics network element 10 has a function of converting the geographical area information corresponding to the target area into the network area information corresponding to the target area, the area information conversion step performed by the NEF network element may be omitted.

It should be noted that, if the first network element 20 is an AMF network element, the first request message may not pass through the NEF network element. That is, a process in which the NEF network element forwards the first request message may be omitted. In this case, the information that is about the target area and that is carried in the first request message is a network area corresponding to the target area, and information about a to-be-assessed area is a network area corresponding to the to-be-assessed area.

In this embodiment of this application, the information about the target time and the information about the target area are provided for the first data analytics network element 10, so that the first data analytics network element 10 determines to collect the data analytics information corresponding to the information about the target time and the information about the target area. In this way, a range of determining the data analytics information by the first data analytics network element 10 can be narrowed.

In another example, the first request message includes information about a to-be-assessed area. In this case, the first request message requests data analytics information corresponding to a terminal in the to-be-assessed area. The terminal in the to-be-assessed area in this embodiment of this application includes a first terminal. For example, if terminals in the to-be-assessed area are a terminal a and a terminal b, the first terminal may be the terminal a or the terminal b, or first terminals may be the terminal a and the terminal b. Alternatively, the first terminal is the terminal in the to-be-assessed area. For example, if terminals in the to-be-assessed area are a terminal a and a terminal b, first terminals are the terminal a and the terminal b.

For example, the information about the to-be-assessed area may be geographical area information corresponding to the to-be-assessed area or network area information corresponding to the information about the to-be-assessed area. The terminal in the to-be-assessed area may be understood as a terminal residing in the to-be-assessed area.

It should be noted that, if the first request message includes information about target time, information about a target area, and the information about the to-be-assessed area, the first data analytics network element 10 may determine that the first network element 20 requests data analytics information that is of a target terminal a and that is associated with the target area within the information about the target time. The target terminal a is an intersection of terminals in the to-be-assessed area and terminals that resided in the target area within the information about the target time.

For example, the terminals in the to-be-assessed area are a terminal 1, a terminal 2, a terminal 3, a terminal 4, and a terminal 5, and terminals that resided in the target area within the information about the target time is the terminal 3, the terminal 4, the terminal 5, a terminal 6, a terminal 7, a terminal 8, a terminal 9, and a terminal 10. In this case, target terminals a are the terminal 3, the terminal 4, and the terminal 5.

Alternatively, in still another example, the first request message includes an identifier of a second terminal, and the first request message requests data analytics information corresponding to the second terminal. The second terminal includes a first terminal, or the second terminal is the same as the first terminal.

It may be understood that the second terminal may represent one or more terminals a, and the one or more terminals a include the first terminal. In other words, the first terminal belongs to the one or more terminals a. Alternatively, the first terminal is the one or more terminals a.

In an example, if the first request message includes information about target time, information about a target area, and the identifier of the second terminal, the first data analytics network element 10 may determine that the first network element 20 requests data analytics information corresponding to the second terminal within the information about the target time and the target area.

In a possible implementation, before step 601 is performed, the method provided in this embodiment of this application may further include: The first network element 20 determines the second terminal.

For example, the first network element 20 is a mobility management network element or a third NWDAF. If the mobility management network element or the third NWDAF determines that a terminal that initially registers appears in an area (for example, a TA or a cell), the mobility management network element or the third NWDAF may determine, as the second terminal, the terminal that initially registers. For example, the first network element 20 is an AF network element. If the AF network element determines that one or more non-resident users newly enter a community, the AF may determine, as the second terminal, a terminal corresponding to the user. Alternatively, if the AF network element receives a query request message that is sent by a user and that is for querying an association relationship between the user or another person and an emergency event, the AF network element determines the queried object user as the second terminal.

In this embodiment of this application, the third NWDAF is responsible for monitoring a resident terminal in the to-be-assessed area. Once a non-resident terminal is discovered in a time interval of the emergency event, the first request message may be triggered. In other words, the first network element 20 may alternatively be the third NWDAF.

The first request message in this embodiment of this application may be first sent by the first network element 20 to an intermediate network element, for example, the NEF network element, and then forwarded by the intermediate network element to the first data analytics network element 10. This is not limited in this embodiment of this application.

The first request message in this embodiment of this application may be provided by the first network element 20 for the first data analytics network element 10. Certainly, the first request message may alternatively be provided by a network element other than the first network element 20. When the first request message is provided by the network element other than the first network element 20, the first request message may further carry indication information y that indicates the first data analytics network element 10 to provide the obtained data analytics information for the first network element 20. Details are not described again in this embodiment of this application.

Step 602: The first data analytics network element 10 determines the data analytics information in response to the first request message.

In one aspect, the first data analytics network element 10 in this embodiment of this application has already had an analyzed data analytics information set (for example, including data analytics information corresponding to a plurality of areas and a plurality of time periods). After the first data analytics network element 10 receives the first request message, if the first request message further carries the information about the target area and the information about the target time, the first data analytics network element 10 determines the data analytics information corresponding to the information about the target time and the information about the target area in the data analytics information set based on the information about the target time and the information about the target area.

In another aspect, after receiving the first request message, the first data analytics network element 10 in this embodiment of this application collects associated data and information based on the first request message, and determines, based on the collected associated data and information, the data analytics information corresponding to the information about the target time and the information about the target area. For example, the first data analytics network element 10 obtains reference data analytics information from a second data analytics network element 30 to determine the data analytics information. For a specific process, refer to the descriptions in the following embodiments. Details are not described herein again.

Step 603 and step 604 are the same as step 502 and step 503. Details are not described herein again.

In a possible implementation, the first request message in this embodiment of this application includes emergency indication information, and the emergency indication information indicates, to the first data analytics network element 10, that the data analytics information requested by the first request message is associated with the emergency event. Correspondingly, that the first data analytics network element 10 in this embodiment of this application determines the data analytics information includes: The first data analytics network element 10 determines the data analytics information based on the emergency indication information. Specifically, if the first data analytics network element 10 determines, based on the emergency indication information, that the first network element 20 is triggered, because of the emergency event, to request the data analytics information, the first data analytics network element 10 determines the data analytics information. In other words, the first data analytics network element 10 determines the data analytics information only when determining that the emergency indication information is received. If the first data analytics network element 10 does not receive the emergency indication information, the first data analytics network element 10 may not determine the data analytics information.

In a possible implementation, step 602 and step 603 in this embodiment of this application may be implemented in the following manner: The first data analytics network element 10 sends the data analytics information to the first network element 20 based on the emergency indication information. It may be understood that, even if the first data analytics network element 10 determines the data analytics information, the first data analytics network element 10 may not send the data analytics information to the first network element 20 if the first data analytics network element 10 does not receive the emergency indication information from the first network element 20. The first data analytics network element 10 sends the data analytics information to the first network element 20 only when receiving the emergency indication information. Alternatively, the first data analytics network element 10 determines the data analytics information, and sends the data analytics information to the first data analytics network element 10 by using the NEF network element. The NEF network element determines, depending on whether the first network element 20 is authorized to obtain the data analytics information, whether to send the data analytics information to the first network element 20. For example, the NEF network element may determine, based on the emergency indication information, that the first network element 20 is authorized to obtain the data analytics information.

In a possible implementation, the first request message in this embodiment of this application may further include emergency event identifier information, and the emergency event identifier information uniquely identifies the emergency event. This helps the first data analytics network element 10 determine a specific emergency event. In addition, the emergency event identifier information may be further for subsequent data statistics, or be for associating the data analytics information with the emergency event.

In a possible implementation, the first network element 20 in this embodiment of this application is the application function network element or the mobility management network element. The first data analytics network element 10 and the second data analytics network element 30 are data analytics network elements that support an emergency event analytics function.

In a possible implementation, when the first network element 20 is the mobility management network element, before step 601, the method provided in this embodiment of this application may further include: The first network element 20 selects a data analytics network element that supports the emergency event analytics function as the first data analytics network element 10.

Specifically, that the first network element 20 selects a data analytics network element that supports the emergency event analytics function as the first data analytics network element 10 may be implemented in the following manner: The first network element 20 obtains the emergency indication information. The first network element 20 selects the data analytics network element that supports the emergency event analytics function as the first data analytics network element 10 based on the emergency indication information.

Specifically, the first data analytics network element 10 may be a data analytics network element that specially supports the emergency event indicated by the emergency event identifier information. Alternatively, the first data analytics network element 10 may be a data analytics network element that supports a plurality of types of emergency events. The plurality of types of emergency events include the emergency event indicated by the emergency event identifier information. Certainly, the first data analytics network element 10 and the following second data analytics network element 30 may alternatively be third data analytics network elements that do not have the emergency event analytics function, but may provide information for the first network element 20 by using a data analytics capability of the third data analytics network elements.

Emergency events in this embodiment of this application include but are not limited to an emergency epidemic event and a public safety event.

In a possible embodiment, as shown in FIG. 6, after step 604, the method provided in this embodiment of this application may further include the following step.

Step 605: The first network element 20 performs, based on the association relationship between the first terminal and the emergency event, an emergency processing operation corresponding to the emergency event.

In a possible implementation, the emergency processing operation includes: The first network element 20 sends first notification information to a sixth terminal, where the first notification information notifies the sixth terminal of the association relationship between the first terminal and the emergency event; and/or the first network element 20 sends second notification information to a second network element, where the second notification information notifies the second network element of the association relationship between the first terminal and the emergency event. The sixth terminal may include the first terminal, or the sixth terminal is the first terminal. For example, the second network element may be an emergency center platform deployed by an operator, and the platform is responsible for releasing an emergency event-associated fore-warning message and the like to a terminal in a network. The first network element 20 (for example, the AMF network element) notifies the second network element (for example, the emergency center platform) of the association relationship, so that the second network element sends the fore-warning information to a user terminal in the network.

It may be understood that the first network element 20 performs other epidemic prevention and control measures based on the association relationship, such as personnel prevention and control, an isolation measure, site disinfection, and personnel fore-warning.

Figure 7:
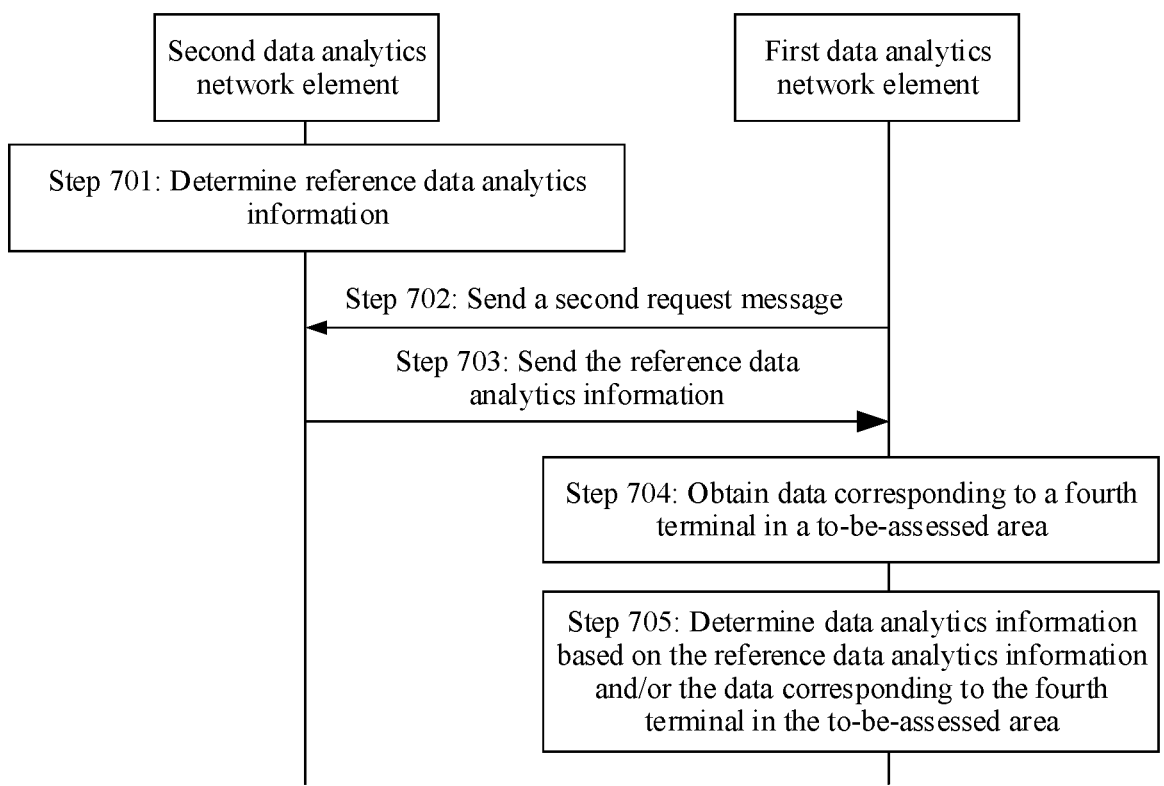
FIG. 7 is a schematic flowchart of determining reference data analytics information according to an embodiment of this application.

FIG. 7 shows a specific implementation of determining data analytics information by a first data analytics network element 10 according to an embodiment of this application. The method includes step 701, step 702, step 703, step 704, and step 705.

Step 701: A second data analytics network element 30 determines reference data analytics information.

The reference data analytics information includes one or more of the following information: an identifier of a third terminal, reference activity degree information of the third terminal, reference moving trajectory information of the third terminal, and reference risk information of the third terminal. The third terminal includes a first terminal.

For example, the third terminal is a terminal associated with an emergency event. In other words, if the reference data analytics information includes the identifier of the third terminal, it may indicate that the third terminal is associated with the emergency event.

It may be understood that the third terminal represents one or more terminals c, and the one or more terminals c include the first terminal. Alternatively, the third terminal and the first terminal are a same terminal.

The second data analytics network element 30 in this embodiment of this application may determine that the emergency event occurs in a target area served by the second data analytics network element 30. In this case, the second data analytics network element 30 determines the reference data analytics information. Alternatively, the second data analytics network element 30 may determine the reference data analytics information based on a request of a network element (for example, receive a second request message from the first data analytics network element 10).

The third terminal in this embodiment of this application may be all or a part of terminals corresponding to information about target time in the target area. The second data analytics network element 30 may actively push all or the part of the terminals corresponding to the information about the target time in the target area to the first data analytics network element 10. Alternatively, the second data analytics network element 30 may feed back all or the part of the terminals corresponding to the information about the target time in the target area to the first data analytics network element 10 at a request of the first data analytics network element 10.

In a possible implementation, the second data analytics network element 30 reports reference data analytics information of all of the terminals corresponding to the information about the target time in the target area to the first data analytics network element 10. For example, terminals in the target area include a terminal 1 to a terminal 9, and only the terminal 4 to the terminal 7 in the terminal 1 to the terminal 9 are located in the target area during a target period. In this case, the second data analytics network element 30 may report reference data analytics information of the terminal 4 to the terminal 7 to the first data analytics network element 10.

In a possible implementation, the second data analytics network element 30 reports reference data analytics information of the part of the terminals corresponding to the information about the target time in the target area to the first data analytics network element 10. For example, the second data analytics network element 30 obtains, through analytics, a terminal of one or more risky users corresponding to the information about the target time in the target area. Then, the second data analytics network element 30 actively provides the first data analytics network element 10 with reference data analytics information of the terminal of the one or more risky users corresponding to the information about the target time in the target area. The risky user may be a user associated with the emergency event. For example, if the emergency event is an epidemic event, the risky user may be a user who had direct contact with an epidemic occurrence place or an epidemic occurrence person. A meaning of a risk may be that the user is risky, or may indicate that another person is risky due to the user.

Step 702: The first data analytics network element 10 sends the second request message to the second data analytics network element 30. Correspondingly, the second data analytics network element 30 receives the second request message from the first data analytics network element 10. The second request message requests reference data analytics information corresponding to the information about the target time and information about the target area.

For example, the second request message carries indication information z, where the indication information z indicates to request the reference data analytics information corresponding to the information about the target time and the information about the target area.

In a possible implementation, the second request message includes an identifier of one or more terminals, and the second request message requests reference data analytics information corresponding to the one or more terminals. Specifically, the second request message requests reference data analytics information corresponding to the one or more terminals within the information about the target time and the information about the target area. The one or more terminals include the third terminal.

The identifier that is of the one or more terminals and that is carried in the second request message in this embodiment of this application may be one or more of the following: when a first request message includes information about a to-be-assessed area, 1. an identifier of all or a part of terminals in the to-be-assessed area; 2. an identifier of a terminal that exited the to-be-assessed area during the target period and that is in the to-be-assessed area; 3. an identifier of a terminal that is in all or the part of the terminals in the to-be-assessed area and whose user is determined as a user associated with the emergency event; and 4. identifiers of all terminals that resided in the target area during the target period and that are in the to-be-assessed area; and when a first request message includes an identifier of a second terminal, identifiers of all or a part of second terminals.

The one or more terminals carried in the second request message in this embodiment of this application include the third terminal, or the one or more terminals are the same as the third terminal.

When the second data analytics network element 30 receives the second request message including the identifier of the one or more terminals, a terminal represented by the third terminal includes a terminal in the one or more terminals.

It should be noted that step 702 and step 701 in this embodiment of this application are not performed in sequence. For example, if step 702 is performed before step 701, after receiving the second request message, the second data analytics network element 30 performs step 701 in response to the second request message. Alternatively, if step 702 is performed after step 701, the second data analytics network element 30 has determined the reference data analytics information. Then, in response to the second request message, the second data analytics network element 30 determines to perform step 703.

Step 703: The second data analytics network element 30 sends the reference data analytics information to the first data analytics network element 10. Correspondingly, the first data analytics network element 10 receives the reference data analytics information from the second data analytics network element 30.

It should be understood that the second data analytics network element 30 may provide only the identifier of the third terminal for the first data analytics network element 10. In addition, to more effectively determine the data analytics information by the first data analytics network element 10, the second data analytics network element 30 may further provide information such as the reference moving trajectory information or the reference risk information for the first data analytics network element 10.

In one aspect, the second data analytics network element 30 in this embodiment of this application may actively send the reference data analytics information to the first data analytics network element 10. For example, if the second data analytics network element 30 determines that the emergency event occurs in an area served by the second data analytics network element 30, the second data analytics network element 30 may send the reference data analytics information to the first data analytics network element 10. It should be noted that, when the second data analytics network element 30 may actively send the reference data analytics information to the first data analytics network element 10, step 702 may be omitted.

In another aspect, the second data analytics network element 30 determines, based on a request of a network element a, to send the reference data analytics information to the first data analytics network element 10. For example, the network element a may be the first data analytics network element 10.

For example, the reference moving trajectory information includes one or more of the following information: reference location information, a time point of entering a location range corresponding to the reference location information, and stay duration in the reference location range. The reference location information is a reference location of the third terminal. The reference location of the third terminal is a location that is experienced by the third terminal in the target area and that is obtained by the second data analytics network element 30 through analytics. For example, the reference location of the third terminal may be determined by the second data analytics network element 30 based on one or more locations experienced by the third terminal in the target area.

For example, the reference risk information includes one or more of the following information: reference risk classification information, a reference risk degree, and a reference risk removal time point.

For a meaning of the reference risk information in this embodiment of this application, refer to the meaning of the first risk information. For the reference risk classification information, refer to the meaning of the first risk classification information. For the reference risk degree, refer to the meaning of the first risk degree. For the reference risk removal time point, refer to the meaning of the first risk removal time point. In this embodiment of this application, the word "reference" means that the information is provided by the second data analytics network element 30 for the first data analytics network element 10.

Step 704: The first data analytics network element 10 obtains data corresponding to a fourth terminal in the to-be-assessed area, where the data includes one or more of the following information: service behavior information, location information, and moving trajectory information, and the fourth terminal includes the first terminal, or the fourth terminal is the same as the first terminal.

For example, the service behavior information may be information such as travel information of the fourth terminal, frequency of entering and exiting an area, or whether, obtained from a medical system, a user of the fourth terminal had a fever or purchased medicine.

It may be understood that the fourth terminal in this embodiment of this application may be all or the part of the terminals in the to-be-assessed area. Alternatively, the fourth terminal may be a part or all of second terminals provided by the first network element 20 by using the first request message. Alternatively, the fourth terminal may be all or a part of terminals determined by the first network element 20 in terminals in the to-be-assessed area based on the information about the target time and the information about the target area. Alternatively, the fourth terminal may be the third terminal.

For example, step 704 in this embodiment of this application may be implemented in the following manner: The first data analytics network element 10 collects, from a (R)AN network element, an NF network element (for example, an AMF network element), an AF network element, an OAM, or the like corresponding to the to-be-assessed area, data corresponding to the fourth terminal in the to-be-assessed area. For example, the data corresponding to the fourth terminal in the to-be-assessed area may be shown in Table 1.

TABLE 1

|  | Type of collected data | Data source | Description and example |
| --- | --- | --- | --- |
| Identifier | Identifier of a terminal (UE ID) | AMF network element, SMF network element, AF network element, and the like | Identify the terminal, for example, an IMSI, an SUPI, an IMEI, a GPSI, IP address information, and a 5-tuple |
|  | Location information of the terminal (UE location) | AMF network element, OAM, location service (LCS) client | Location information of the terminal in a network, for example, a cell ID, a TA ID, MR location information, and LCS location information |
|  | Moving trajectory of the terminal (UE moving trajectory) | AMF network element | Moving trajectory information of the terminal in the network, for example, a list of IDs of cells in which the terminal continuously resides. |
|  | Mobility analytics information of the terminal (UE mobility analytics) | Third NWDAF | Mobility analytics information that is of the terminal in the network and that is obtained by the third NWDAF through analytics, for example, information about a location that the terminal enters, a time point at which the terminal enters the location, and frequency of re-registration of the terminal |
| Time information | Time information | AMF network element, OAM, and LCS client | Data collection time information that may be information about a sampling time point or a sampling time period, for example, 08:00:00 or 08:00-09:00 |
| Service behavior information | Contact information of another user a associated with an emergency event | AF network element | For example, whether contact with the user a occurs, a time point of contacting with the user a, and contact duration |
|  | Service information of the UE | AF network element | Terminal-associated service information, for assisting in determining whether a user of the terminal is a risky user, for example, a medical treatment record of the terminal, a medicine purchase record of the terminal, and whether the terminal went to a designated hospital by using DiDi Dache |

Step 705: The first data analytics network element 10 determines the data analytics information based on the reference data analytics information and/or the data corresponding to the fourth terminal in the to-be-assessed area.

In a possible implementation, the reference data analytics information in this embodiment of this application is the reference data analytics information corresponding to the information about the target time and the information about the target area. This helps the first data analytics network element 10 determine time or an area corresponding to the reference data analytics information.

In a possible implementation, that the first data analytics network element 10 determines the data analytics information based on the reference data analytics information and/or the data corresponding to the fourth terminal in the to-be-assessed area in this embodiment of this application includes: The first data analytics network element 10 determines the data analytics information based on the identifier of the third terminal, the reference activity degree information of the third terminal, and the data corresponding to the fourth terminal in the to-be-assessed area.

For example, the third terminal represents a terminal n11, a terminal n12, and a terminal n13, and the fourth terminal represents the terminal n11, the terminal n13, and a terminal n21. The first data analytics network element 10 obtains terminals (for example, the terminal n11 and the terminal n13) common to the terminals represented by the third terminal and the terminals represented by the fourth terminal, and determines comprehensive activity degree information of the terminal n11 and comprehensive activity degree information of the terminal n13 for reference activity degree information corresponding to the terminal n11, reference activity degree information corresponding to the terminal n13, moving trajectory information of the terminal n11 in the to-be-assessed area, and moving trajectory information of the terminal n13 in the to-be-assessed area. The first data analytics network element 10 determines the terminal n11 and the terminal n13 as first terminals, and determines the comprehensive activity degree information as activity degree information of the first terminals.

In another possible implementation, that the first data analytics network element 10 determines the data analytics information based on the reference data analytics information and/or the data corresponding to the fourth terminal in the to-be-assessed area includes: The first data analytics network element 10 determines the data analytics information based on the identifier of the third terminal and the reference moving trajectory information of the third terminal. For example, the third terminal is the first terminal. If the first data analytics network element 10 determines, based on reference moving trajectory information of the first terminal, that a moving trajectory of the first terminal includes a location range that has been defined as a risk area, the first data analytics network element 10 may determine that first risk classification information of the first terminal is that the first terminal is risky, and the first data analytics network element 10 includes the first risk classification information in first risk information.

In still another possible implementation, that the first data analytics network element 10 determines the data analytics information based on the reference data analytics information and/or the data corresponding to the fourth terminal in the to-be-assessed area includes: The first data analytics network element 10 determines the data analytics information based on the moving trajectory information corresponding to the fourth terminal in the to-be-assessed area. For example, if the first data analytics network element 10 determines, based on the moving trajectory information corresponding to the fourth terminal in the to-be-assessed area, that moving trajectory information corresponding to the first terminal included in the fourth terminal in the to-be-assessed area shows that the first terminal went to a range that has been defined as a risk area, the first data analytics network element 10 determines that first risk information of the first terminal indicates that there is a risk. For example, if the first data analytics network element 10 determines, based on the moving trajectory information corresponding to the fourth terminal in the to-be-assessed area, that moving trajectory information corresponding to the first terminal included in the fourth terminal in the to-be-assessed area shows that the first terminal did not go to a range that has been defined as a risk area, the first data analytics network element 10 determines that first risk classification information of the first terminal is that the first terminal is risky, and the first data analytics network element 10 includes the first risk classification information in first risk information.

In still another possible implementation, that the first data analytics network element 10 determines the data analytics information based on the reference data analytics information and/or the data corresponding to the fourth terminal in the to-be-assessed area includes: The first data analytics network element 10 determines the data analytics information based on the moving trajectory information and the service behavior information that correspond to the fourth terminal in the to-be-assessed area. For example, the emergency event is the epidemic event. If the first data analytics network element 10 determines, based on the moving trajectory information corresponding to the fourth terminal in the to-be-assessed area, that moving trajectory information corresponding to the first terminal included in the fourth terminal in the to-be-assessed area shows that the first terminal went to a range that has been defined as a risk area, and service behavior information of the first terminal in the to-be-assessed area shows that the first terminal went to a fever clinic in a hospital or a pharmacy, the first data analytics network element 10 determines that a first risk degree of the first terminal is a high risk, and the first data analytics network element 10 includes the first risk degree in first risk information. For example, if the first data analytics network element 10 determines, based on the moving trajectory information corresponding to the fourth terminal in the to-be-assessed area, that moving trajectory information corresponding to the first terminal included in the fourth terminal in the to-be-assessed area shows that the first terminal went to a range that has been defined as a risk area, but service behavior information of the first terminal in the to-be-assessed area shows that the first terminal did not go to a fever clinic in a hospital or a pharmacy, the first data analytics network element 10 determines that a first risk degree of the first terminal is a moderate risk, and the first data analytics network element 10 includes the first risk degree in first risk information. For another example, if the first data analytics network element 10 determines, based on the moving trajectory information corresponding to the fourth terminal in the to-be-assessed area, that moving trajectory information corresponding to the first terminal included in the fourth terminal in the to-be-assessed area shows that the first terminal did not go to a range that has been defined as a risk area, but service behavior information of the first terminal in the to-be-assessed area shows that the first terminal did not go to a fever clinic in a hospital or a pharmacy, the first data analytics network element 10 determines that a first risk degree of the first terminal is a moderate risk, and the first data analytics network element 10 includes the first risk degree in first risk information.

In still another possible implementation, that the first data analytics network element 10 determines the data analytics information based on the reference data analytics information and/or the data corresponding to the fourth terminal in the to-be-assessed area includes: The first data analytics network element 10 determines the data analytics information based on the reference risk information of the third terminal and the data corresponding to the fourth terminal in the to-be-assessed area. For example, an intersection of third terminals and fourth terminals is the first terminal. If the first data analytics network element 10 determines, based on reference risk information of the first terminal, that the first terminal is not risky, but the first data analytics network element 10 determines that moving trajectory information corresponding to the first terminal in the to-be-assessed area shows that the first terminal went, within the information about the target time, to a range that has been defined as a risk area, the first data analytics network element 10 may determine that first risk classification information of the first terminal is that the first terminal is risky, and the first data analytics network element 10 includes the first risk classification information in first risk information. In addition, the first data analytics network element 10 may further determine risk degree information of the first terminal based on the reference risk information of the third terminal and the data corresponding to the fourth terminal in the to-be-assessed area, and include the risk degree information of the first terminal in risk information of the first terminal.

In a possible implementation, that the first data analytics network element 10 determines the data analytics information based on the reference data analytics information and/or the data corresponding to the fourth terminal in the to-be-assessed area includes: The first data analytics network element 10 determines the data analytics information of the third terminal based on the identifier of the third terminal and the moving trajectory information corresponding to the fourth terminal in the to-be-assessed area. For example, the reference data analytics information includes the identifier of the third terminal, and the third terminal is a risky user that is associated with the emergency event and that is obtained by the second data analytics network element 30 through analytics. If the first data analytics network element 10 uses an intersection of third terminals and fourth terminals as the first terminal, the first data analytics network element 10 may determine that a user of the first terminal is a risky user. Then the first data analytics network element 10 may determine, in moving trajectory information corresponding to the first terminal in the to-be-assessed area, the moving trajectory information corresponding to the first terminal in the to-be-assessed area, to obtain the moving trajectory information of the first terminal.

In the following manner 1 or manner 2, how the second data analytics network element 30 determines the reference data analytics information is mainly described.

Manner 1: The second data analytics network element 30 in this embodiment of this application may determine the reference data analytics information in the following manner: The second data analytics network element 30 has a terminal list n (including the third terminal) (including identifiers of m terminals, where m is an integer greater than or equal to 1) corresponding to the target area and the information about the target time and reference data analytics information corresponding to each terminal in the terminal list n. The terminal list n corresponding to the target area and the information about the target time may be understood as m terminals that access, in a time period indicated by the information about the target time, a network that serves the target area, or m terminals that in the target area in the time period indicated by the information about the target time. In this way, after the second data analytics network element 30 receives the second request message, the second data analytics network element 30 may obtain the identifier of the third terminal by obtaining an intersection of the identifier of the one or more terminals that is included in the second request message and the terminal list n. In addition, if the second data analytics network element 30 further has the reference data analytics information corresponding to the terminal in the terminal list n, the second data analytics network element 30 may determine, based on identifier of the third terminal, the reference data analytics information of the third terminal in the reference data analytics information corresponding to the terminal in the terminal list n. Therefore, the second data analytics network element 30 may determine the reference data analytics information.

Manner 2: The second data analytics network element 30 in this embodiment of this application may determine the reference data analytics information in the following manner: The second data analytics network element 30 obtains first data, where the first data includes one or more of the following information of a fifth terminal corresponding to the information about the target time and the information about the target area: an identifier, location information, moving trajectory information, and service behavior information that are of the terminal, and the fifth terminal includes the third terminal. The second data analytics network element 30 determines reference data analytics information based on the first data.

For example, the fifth terminal may be all or a part of the one or more terminals in the second request message. Alternatively, the fifth terminal may be all or a part of terminals in the target area, or the fifth terminal may be all or a part of terminals corresponding to the information about the target time in the target area. Alternatively, the fifth terminal may be an intersection of terminals in the to-be-assessed area and terminal in the target areas. This is not limited in this embodiment of this application. A terminal corresponding to the information about the target time may mean that the terminal accesses a network of an area within the information about the target time.

It may be understood that, for content of the first data, refer to the descriptions in Table 1. A difference lies in that a network element providing the first data is a network element that serves the target area. For example, the location information that is of the terminal and that is included in the first data may be provided by an AMF network element that serves the target area.

In a possible implementation, that the second data analytics network element 30 determines reference data analytics information based on the first data includes: The second data analytics network element 30 determines the reference data analytics information based on the location information and the service behavior information of the fifth terminal within the information about the target time and the target area.

For example, if the second data analytics network element 30 determines that the location information of the fifth terminal within the information about the target time and the target area is in a range defined as a risk area, and the service behavior information of the fifth terminal shows that the fifth terminal performed behavior (for example, purchased a medicine for treating a fever or treated in a fever clinic)

associated with the emergency event, the second data analytics network element 30 determines that a reference risk degree of the fifth terminal in the reference data analytics information is a high risk.

In a possible implementation, that the second data analytics network element 30 determines reference data analytics information based on the first data includes: The second data analytics network element 30 determines the reference data analytics information based on the location information of the fifth terminal within the information about the target time and the target area. For example, if the second data analytics network element 30 determines, based on the location information of the fifth terminal in the information about the target time and the target area, that the fifth terminal accesses a network in a risk area, the second data analytics network element 30 determines that reference risk classification information of the fifth terminal in the reference data analytics information is that the fifth terminal is risky. In a possible implementation, before the first data analytics network element 10 sends the second request message to the second data analytics network element 30, the method provided in this embodiment of this application further includes: The first data analytics network element 10 determines information about the second data analytics network element 30 that serves the target area.

For example, the fifth terminal accesses an area 1, an area 2, an area 3, and an area 4 in the target area. A risk degree corresponding to the area 1 and the area 4 are a level A, a risk degree corresponding to the area 2 is a level B, and a risk degree corresponding to the area 3 is a level C. There is an internal algorithm in the second data analytics network element 30. In the algorithm, risk degree weights of level-A, level-B, and level-C areas are respectively set to a weight a, a weight b, and a weight c. Therefore, the second data analytics network element 30 determines that reference risk information of the fifth terminal in the reference data analytics information is: an activity index of the fifth terminal in the area 1 multiplied by the weight a+an activity index of the fifth terminal in the area 4 multiplied by the weight a+an activity index of the fifth terminal in the area 2 multiplied by the weight b+an activity index of the fifth terminal in the area 3 multiplied by the weight c. An activity index of a user in an area refers to a function value calculated based on information such as a quantity of times of activities or activity duration of the user in the area, and is used to represent an activity degree of the user in the area.

For example, the first data analytics network element 10 may determine, in the following manner, the information about the second data analytics network element 30 that serves the target area: The first data analytics network element 10 determines the second data analytics network element based on first information, where the first information includes one or more of the following information: emergency indication information and emergency event identifier information.

In a possible implementation, the first data analytics network element 10 may determine, in the following manner, the information about the second data analytics network element 30 that serves the target area: The first data analytics network element 10 has first configuration information, where the first configuration message includes information about each area (including the target area) and information about a data analytics network element that serves the area. In this way, the first data analytics network element 10 may determine, based on the information about the target area, to query the first configuration information to determine the information about the second data analytics network element 30 that serves the target area.

In another possible implementation, the first data analytics network element 10 may determine, in the following manner, the information about the second data analytics network element 30 that serves the target area: The first data analytics network element 10 obtains, from an NRF network element, the information about the second data analytics network element 30 that serves the target area. For specific implementation of this process, refer to a process in which an NWDAF 1 obtains, from an NRF network element, information about an NWDAF 2 that serves the target area in the following embodiment. Details are not described herein again.

The target area in this embodiment of this application may be an area in which the terminal resided, but the terminal currently does not reside in the area. The to-be-assessed area may be an area in which the terminal currently resides.

Figure 8A:
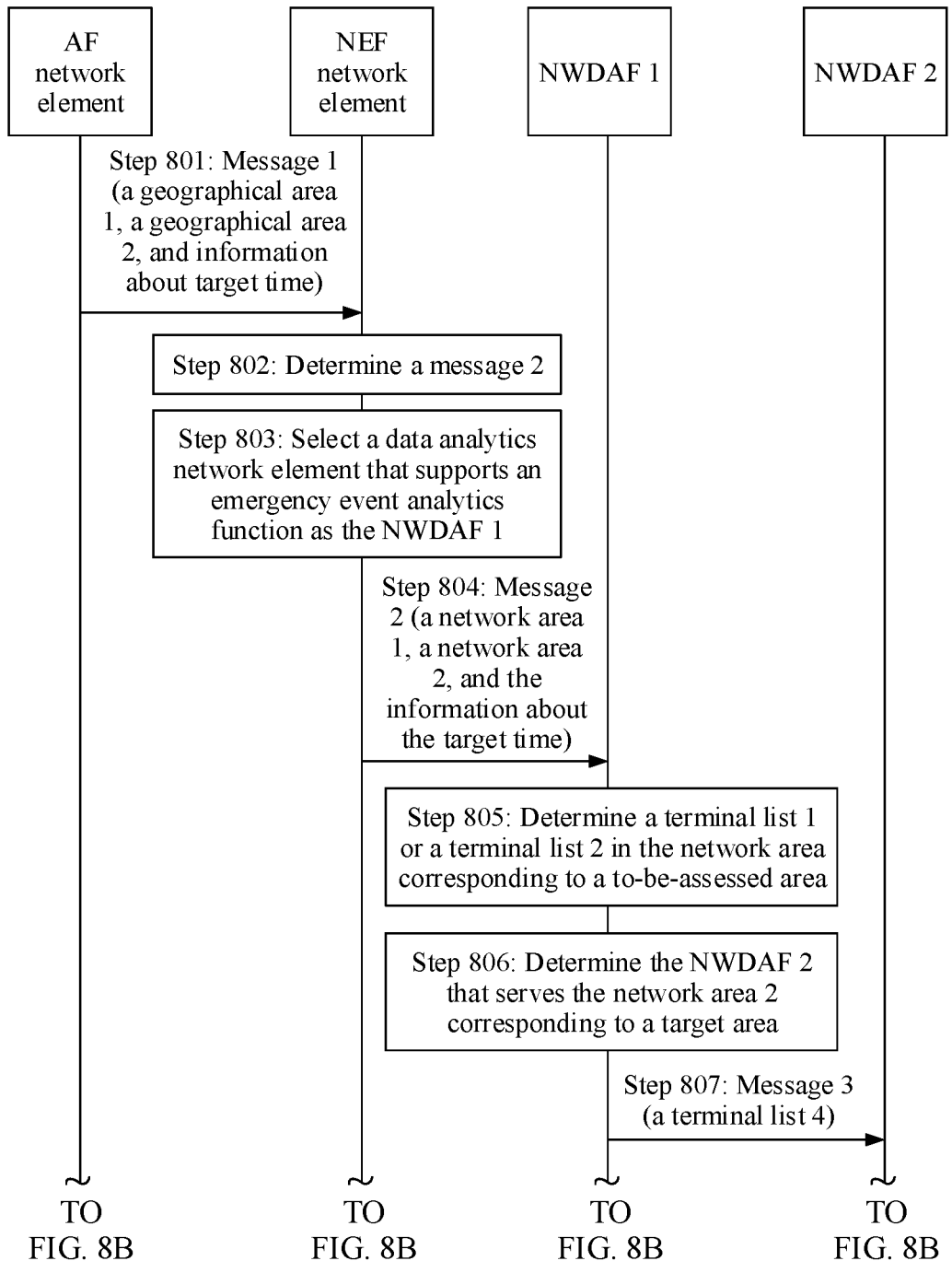
FIG. 8A to FIG. 10 each show a specific embodiment of an information processing method according to an embodiment of this application.
Figure 8B:
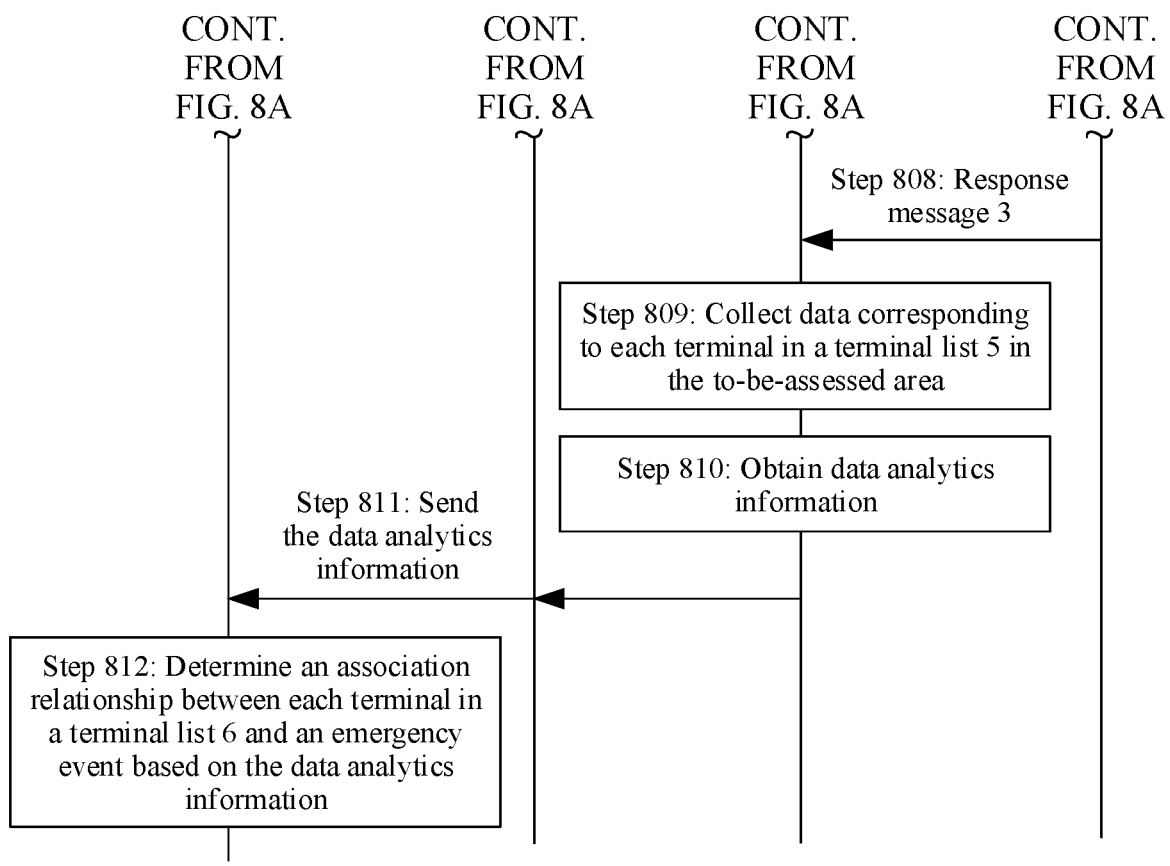

In FIG. 8A and FIG. 8B, a specific embodiment of an information processing method according to an embodiment of this application is described by using an example in which a first data analytics network element 10 is an NWDAF 1, a second data analytics network element 30 is an NWDAF 2, and a first network element 20 is an AF network element. The method includes the following steps.

Step 801: The AF network element sends a message 1 to an NEF network element. Correspondingly, the NEF network element receives the message 1 from the AF network element. The message 1 requests the NWDAF 1 to provide data analytics information of a terminal.

For example, the message 1 may carry indication information 1, and the indication information 1 requests the NWDAF 2 to provide the data analytics information of the terminal.

For example, the message 1 includes one or more of a geographical area (geo area) 1 corresponding to a to-be-assessed area, a geographical area 2 corresponding to a target area, and information about target time.

For example, if the message 1 includes the geographical area 1 corresponding to the to-be-assessed area, the geographical area 2 corresponding to the target area, and the information about the target time, the message 1 indicates, to the NWDAF 1, that the AF network element requests a list of terminals that were located in the target area within the information about the target time and that are in the to-be-assessed area. For example, the to-be-assessed area is a city A, the target area is a city B, and the information about the target time is Jan. 1, 2019 to Jan. 21, 2019. In this case, the AF network element may query the NWDAF 1 for data analytics information of a terminal c by using the message 1. The terminal c herein includes a set of terminals in the city A and terminals that access the city B from Jan. 1, 2019 to Jan. 21, 2019.

Alternatively, the AF network element queries, from the NWDAF 1 by using the message 1, data analytics information of a terminal that is located in the city A currently or historically and that left the city A from Jan. 1, 2019 to Jan. 21, 2019.

For example, the message 1 includes the geographical area 2 corresponding to the target area and the information about the target time. In this case, the message 1 indicates, to the NWDAF 1, that the AF network element requests data analytics information of a terminal located in the target area within the information about the target time. For example, the target area is a city B, and the information about the target time is Jan. 1, 2019 to Jan. 21, 2019, the AF network element requests, from the NWDAF 1, data analytics information of a terminal located in the city B from Jan. 1, 2019 to Jan. 21, 2019, or the AF network element requests, from the NWDAF 1, data analytics information of a terminal that leaves a city A from Jan. 1, 2019 to Jan. 21, 2019.

For example, if the message 1 includes the geographical area 2 corresponding to the target area and the geographical area 1 corresponding to the to-be-assessed area, the message 1 indicates, to the NWDAF 1, that the AF network element requests data analytics information of a terminal that was located in the target area and that is in terminals in the to-be-assessed area.

For example, the message 1 includes the geographical area 2 corresponding to the target area and the information about the target time. In this case, the message 1 indicates, to the NWDAF 1, that the AF network element requests data analytics information of a terminal that went, within the information about the target time, to the geographical area 2 corresponding to the target area.

In a possible implementation, the message 1 may further carry emergency indication information that indicates, to the NWDAF 1, that the requested data analytics information is associated with an emergency event. In other words, the emergency indication information indicates, to the NWDAF 1, that the data analytics information associated with the emergency event is requested, or indicates that the data analytics information is requested from the NWDAF 1 due to the emergency event.

In a possible implementation, the message 1 may further include emergency event identifier (emergency event ID) information, and the emergency event identifier information may indicate one or more emergency events. The emergency event identifier information is used to help the NWDAF 1 determine that the data analytics information requested by the AF network element is associated with a specific emergency event indicated by the emergency event identifier information.

In a possible implementation, in addition to requesting the NWDAF 1 to provide a risky terminal list (which may be a terminal of a risky user) for the AF network element, the message 1 in this embodiment of this application further requests the NWDAF 1 to provide the AF network element with associated analytics information corresponding to each terminal in the risky terminal list, for example, first risk information and first moving trajectory information.

For example, the message 1 may be a data analytics exposure subscribe service operation (Nnef_analyticsexposure_subscribe).

In a specific implementation, the AF sends an analytics information subscription request message (Nnef_analyticsexposure_subscribe) to the NEF, and the requested data analytics information is specifically identified by using an analytics ID. For example, the risky terminal list corresponds to an analytics ID 1. Other analytics information corresponds to another analytics ID. For example, the first risk information corresponds to an analytics ID 2, and the first moving trajectory information corresponds to an analytics ID 3. information about the target area, information about the to-be-assessed area, and the information about the target time may be included in Nnef_analyticsexposure_subscribe as filter information. The emergency indication information and the emergency event identifier emergency event ID information are also included in Nnef_analyticsexposure_subscribe, and may be used as a part of the filter information or not used as the filter information.

Step 802: The NEF network element determines a message 2 based on the message 1, where the message 2 carries one or more of a network area 1, a network area 2, and the information about the target time.

For example, the NEF network element converts a geographical area included in the message 1 into a network area. For example, the NEF network element converts the geographical area 1 corresponding to the to-be-assessed area into a network area 1 that corresponds to the to-be-assessed area and that may be identified by the NWDAF 1, and converts the geographical area 2 corresponding to the target area into a network area 2 that corresponds to the target area and that may be identified by the NWDAF 1. An objective of performing the foregoing conversion is that area information provided by the AF network element is generally geographical location information, but a network function (for example, the NWDAF 1) usually cannot directly identify the area information. It may be understood that, if the AF network element provides the network area 2 corresponding to the target area and the network area 1 corresponding to the to-be-assessed area, an action of performing area conversion by the NEF network element may be omitted.

In a possible implementation, if the message 1 further carries an emergency event ID identifier, the NEF network element converts the emergency event ID into information that may be identified by the NWDAF 1. For example, an emergency event ID "Corona Virus Disease 2019" is converted into a corresponding numeric identifier 010110. In addition, the NEF network element may further convert the information that is about the target time and that is carried in the message 1 into a time period that may be identified by the NWDAF 1.

Step 803: When the NEF network element determines that the data analytics information that is of a risky user and that is requested by the AF network element is associated with the emergency event, the NEF network element selects a data analytics network element that supports an emergency event analytics function as the NWDAF 1.

In an example, if the NEF network element receives the emergency indication information or the emergency event identifier information from the AF network element, the NEF network element determines that the data analytics information requested by the AF network element is associated with the emergency event.

For example, the emergency indication information or the emergency event identifier information may be carried in the data analytics expose subscribe service operation. Certainly, the emergency indication information or the emergency event identifier information may alternatively be sent by the AF network element to the NEF network element by using another message. This is not limited in this embodiment of this application.

In an implementation, the NEF network element may select the data analytics network element that supports the emergency event analytics function as the NWDAF 1 in the following manner: The NEF network element may send a query message 1 to an NRF network element based on the emergency indication information. Then, the NEF network element provides, based on the query message 1, the NRF network element with information about an emergency NWDAF that supports the emergency event analytics function and that serves the to-be-assessed area. The query message 1 is used to query the emergency NWDAF that is configured to serve the to-be-assessed area and that supports the emergency event analytics function. Then, the NEF network element determines the NWDAF 1 based on the information about the emergency NWDAF that supports the emergency event analytics function. For example, the NEF network element uses, as the NWDAF 1, the emergency NWDAF indicated by the information about the emergency NWDAF that supports the emergency event analytics function.

For example, the query message 1 may carry the network area 1 and one or more of the following information: an emergency indication and the emergency event ID, used by the NRF network element to find the emergency NWDAF corresponding to the information.

For example, the information about the emergency NWDAF may be one or more of an address, an identifier, or a fully qualified domain name (FQDN) of the emergency NWDAF.

In another implementation, the NEF network element may select the data analytics network element that supports the emergency event analytics function as the NWDAF 1 in the following manner: Information (an address, an identifier, an FQDN, or the like) about an emergency NWDAF associated with the emergency event may be configured on the NEF network element. In this way, the NEF network element may determine the NWDAF 1 based on the configuration information of the NEF network element.

Step 804: The NEF network element sends the message 2 to the NWDAF 1. Correspondingly, the NWDAF 1 receives the message 2 from the NEF network element. The message 2 requests the NWDAF 1 to provide the data analytics information of the terminal.

It may be understood that for content included in the message 2, refer to the content in the message 1, and a meaning of each piece of content is the same as that described above. A difference between the content in the message 2 and the content in the message 1 lies in that, if the NEF network element performs an internal-external area conversion operation, the message 2 includes the network area 1 corresponding to the to-be-assessed area and the network area 2 corresponding to the target area.

For example, the message 2 may be an analytics information subscription request (Nnwdaf_analyticssubscription) between the NEF network element and the NWDAF 1.

Step 805: The NWDAF 1 determines, based on the message 2, a terminal list 1 or a terminal list 2 in the network area corresponding to the to-be-assessed area.

In an example, step 805 in this embodiment of this application may be implemented in the following manner: The NWDAF 1 determines the terminal list 1 based on all or a part of terminals residing in the network area 1. For example, the terminal list 1 includes identifiers of all or the part of the terminals residing in the network area 1. For example, the NWDAF 1 may query, from an AMF network element or a UDM network element, the identifiers of all or the part of the terminals residing in the network area.

In another example, step 805 in this embodiment of this application may be implemented in the following manner: The NWDAF 1 obtains the terminal list 2 from the terminal list 1 based on one or more of the network area 1, the network area 2, and the information about the target time. The terminal list 2 is a subset of the terminal list 1. For example, an identifier of a terminal included in the terminal list 2 are a part of identifiers of terminals included in the terminal list 1.

It may be understood that the NWDAF 1 may determine, based on the terminal list 1 and information (travel information of a user of a terminal in the terminal list 1) obtained from a third-party AF network element, an identifier of a terminal that went to the network area 2 within the information about the target time, to obtain the terminal list 2. Alternatively, the NWDAF 1 may determine that the terminal list 2 does not include an identifier of a terminal that is in the terminal list 1 and that always resides in the network area 1 in a time period.

It may be understood that not all users of terminals that are in the to-be-assessed area and that are requested by the AF network element are risky users. Therefore, the NWDAF 1 may narrow, by determining the terminal list 2, a range of users whose risks are to be assessed. However, a range of risky users in the to-be-assessed area may be narrowed in another manner. This is not limited in this embodiment of this application.

Step 806: The NWDAF 1 determines the NWDAF 2 that serves the network area 2 corresponding to the target area.

In a possible implementation, step 806 in this embodiment of this application may be implemented in the following manner: The NWDAF 1 sends a query message 2 to the NRF network element, to obtain the NWDAF 2 that serves the network area 2. The query message 2 includes the network area 2, the emergency indication, or the emergency event ID.

It may be understood that, in the network element registration procedure requested by the NWDAF 2 from the NRF, the NWDAF 2 may provide indication information for the NRF network element to indicate that the NWDAF 2 is an NWDAF that supports the emergency event. In addition, the NWDAF 2 may further provide the NRF network element with the emergency event ID supported by the NWDAF 2.

Step 807: The NWDAF 1 sends a message 3 to the NWDAF 2. Correspondingly, the NWDAF 2 receives the message 3 from the NWDAF 1. The message 3 requests the NWDAF 2 to feed back reference data analytics information.

The message 3 carries a terminal list 4. For example, the terminal list 4 may be the terminal list 2 or the terminal list 1. It may be understood that, if the NWDAF 2 performs a process of determining the terminal list 2 based on the terminal list 1, the terminal list 4 carried in the message 3 is the terminal list 2. If the NWDAF 2 does not perform a process of determining the terminal list 2 based on the terminal list 1, the terminal list 4 carried in the message 3 is the terminal list 1.

It may be understood that the message 3 specifically requests the NWDAF 2 to feed back reference data analytics information corresponding to the terminal list 4.

Step 808: The NWDAF 2 sends a response message 3 to the NWDAF 1. Correspondingly, the NWDAF 1 receives the response message 3 from the NWDAF 2. The response message 3 includes reference data analytics information corresponding to a risky terminal list.

For example, the reference data analytics information corresponding to the risky terminal list includes the following information corresponding to a terminal included in the risky terminal list: an identifier, reference activity degree information, reference moving trajectory information, and reference risk information.

It may be understood that the risky terminal list is the terminal list 4, or the risky terminal list is a terminal of a risky user in the terminal list 4.

In a possible implementation, the NWDAF 2 may determine, based on the terminal list 4, whether a user of a terminal described in the terminal list 4 is a risky user. In this way, the NWDAF 2 may provide the NWDAF 1 with reference data analytics information (for example, the reference data analytics information corresponding to the risky terminal list) corresponding to a terminal of a risky user in the terminal list 4. In addition, the NWDAF 2 may further provide the NWDAF 1 with an identifier of a terminal that is not a risky user in the terminal list 4.

In a possible implementation, the NWDAF 2 may provide the NWDAF 1 with reference data analytics information of all terminals described in the terminal list 4, so that the NWDAF 1 autonomously determines, based on the reference data analytics information of all the terminals described in the terminal list 4, whether a user of a terminal described in the terminal list 4 is a risky user, and data analytics information corresponding to the terminal list 4.

In a possible embodiment, before step 808, the method provided in this embodiment of this application may further include: The NWDAF 2 determines the reference data analytics information corresponding to the risky terminal list.

In an implementation, the NWDAF 2 may determine, in the following manner, the reference data analytics information corresponding to the risky terminal list: The NWDAF 2 has reference data analytics information corresponding to a terminal list 3. The NWDAF 2 determines, based on the reference data analytics information corresponding to the terminal list 3 and the terminal list 4, the reference data analytics information corresponding to the risky terminal list.

For example, the terminal list 3 includes an identifier of a terminal 1, an identifier of a terminal 2, and an identifier of a terminal 3. If the NWDAF 2 has reference data analytics information corresponding to each of the terminal 1 to the terminal 3, and the terminal list 4 provided by the NWDAF 1 includes the identifier of the terminal 2 and the identifier of the terminal 3, the NWDAF 1 may determine reference data analytics information corresponding to the terminal 2 and reference data analytics information corresponding to the terminal 3. It may be understood that, if the terminal list 4 further includes an identifier of a terminal 4, and the terminal 4 does not exist in the terminal list 3, it may be considered that the terminal 4 is not a terminal used by a risky user.

It may be understood that the reference data analytics information that corresponds to the terminal list 3 and that the NWDAF 2 may have been determined through analytics of a serving area of the NWDAF 2 in advance before the NWDAF 2 receives the message 3 (for details of a method, refer to the following descriptions). After receiving the message 3, the NWDAF 2 obtains, by comparing the terminal list 4 with the terminal list 3, reference data analytics information corresponding to the risky terminal list.

In another implementation, the NWDAF 2 may determine, in the following manner, the reference data analytics information corresponding to the risky terminal list: After the NWDAF 2 obtains the message 3, the NWDAF 2 obtains first data of each terminal included in the terminal list 4 in the network area 2. The NWDAF 2 determines, based on the first data of the terminal included in the terminal list 4 in the network area 2, the reference data analytics information corresponding to the risky terminal list. For example, for content of the first data, refer to the foregoing description in Table 1. Details are not described herein again.

In a possible implementation, that the NWDAF 2 determines, based on the first data of each terminal included in the terminal list 4, the reference data analytics information corresponding to the risky terminal list includes: The NWDAF 2 determines, based on the first data of the terminal, the network area 2, and the information about the target time, the reference data analytics information corresponding to the risky terminal list.

For example, the NWDAF 1 determines whether any terminal x included in the terminal list 4 resided in an operator network in the network area 2 within the information about the target time. If the any terminal x resided in the operator network in the network area 2 within the information about the target time, the NWDAF 2 determines that reference risk information of the any terminal x is that the any terminal x has a risk associated with the emergency event.

In another possible manner, the NWDAF 2 determines duration in which any terminal resides in the network area 2, a specific location at which the any terminal stays in the network area 2, or whether the any terminal contacted with the target terminal. The target terminal may be considered as a terminal of an emergency event determined user (a user determined to be associated with the emergency event, for example, an epidemic determined person). To determine whether a terminal is a risky user associated with the emergency event, the NWDAF 2 may further obtain, from the AF network element, at least one type of data of the terminal shown in Table 2.

TABLE 2

| Collected data | Source | Content or description |
| --- | --- | --- |
| Information about contact with an emergency event determined user | AF network element | The information about contact with the emergency event determined user includes whether contact with the emergency event determined user occurs, a contact time point, contact duration, and the like |
| Service information of a terminal | AF network element | Used to assist an NWDAF 2 in determining whether a user of the terminal is a user associated with an emergency event, for example, a medical treatment record, a medicine purchase record, and a network taxi hailing record that of the terminal, and whether the terminal went to a designated hospital |

Specifically, Table 3 or Table 4 shows content of the reference data analytics information provided by the NWDAF 2 for the NWDAF 1.

TABLE 3

| Output data type | Description and example |
|---|---|
| Network area | Indicates an observation area range corresponding to reference data analytics information. For example, a city A corresponds to a TA list or a cell ID list |
| Time period | Indicates observation period information corresponding to the reference data analytics information, for example, 2020.01.01-2020.01.30 |
| Identifier of a user associated with an emergency event | |
| >UE ID | Identifier of a terminal, for example, an IMSI, an SUPI, an IMEI, a GPSI, and a UE IP 5-tuple. |

Specifically, Table 4 shows that in addition to providing the risky terminal list (for example, UE IDs in Table 3 and Table 4) and a time period and an area that correspond to the reference data analytics information for the NWDAF 1, the NWDAF 2 may further provide reference risk degree analytics information and the reference moving trajectory information that correspond to the risky terminal list.

TABLE 4

| Output data type | Description and example |
|---|---|
| Network area | Indicates an observation area range corresponding to reference data analytics information. For example, a city corresponds to a TA list or a cell ID list |
| Time period | Indicates observation period information corresponding to the reference data analytics information, for example, 2020.01.01-2020.01.30 |
| Terminal List | |
| >Identifier of a terminal | Identify the terminal |
| >Reference risk degree analytics information | |
| >>Information about a stay history in a high-risk area | List of high-risk areas that the terminal enters, a time point of entering each high-risk area, stay duration, and the like, for example, a high-risk area, an entry time point 2020.01.05 12:30, and stay duration 48 minutes; and an XX fever clinic, an entry time point 2020.01.10 09:30, and stay duration 3 hours |
| >>Information about a contact history with an emergency event determined user | List of contacted emergency event determined users, duration for which an emergency event occurs on the contacted emergency event determined user, and duration of contact with the emergency event determined user, for example, contact with Zhang San, a disease occurs for three days, contact duration one hour |
| >>Reference risk degree Reference moving trajectory information | May be represented in a numerical form, for example, 80%, or a level form, for example, high, moderate, or low. |
| >>Location information of the terminal | Network location that the terminal enters, for example, a cell, a TA, and an LCS location |
| >>information about an entry time point | Time point at which the terminal enters the location, for example, a time point of entering a cell 1 |
| >>Stay duration | Duration for which the terminal stays in the location, for example, duration of staying in the cell 1 |
| >Time point of roaming out of a network area | Time point at which the terminal roams out of an observation area, for example, a time point at which UE roams out of a network of a city |

Step 809: The NWDAF 1 collects data corresponding to each terminal in a terminal list 5 in the to-be-assessed area, where the data corresponding to the terminal in the terminal list 5 in the to-be-assessed area is used to determine moving trajectory information, service behavior information, or the like of the terminal in the terminal list 5 in the to-be-assessed area.

For example, the NWDAF 1 collects data, shown in Table 1, corresponding to the terminal in the terminal list 5 in the to-be-assessed area. A difference lies in that the NWDAF 1 collects, from a corresponding network element such as an NF, an AF, or an OAM that serves the network area 1, the data corresponding to the terminal in the terminal list 5 in the to-be-assessed area.

It may be understood that terminals in the terminal list 5 include all terminals in the network area 1. Alternatively, terminals in the terminal list 5 include a part of terminals in the network area 1. For example, the terminals in the terminal list 5 are an intersection of terminals in the network area 1 and terminals in the network area 2.

Step 810: The NWDAF 1 obtains the data analytics information based on the reference data analytics information fed back by the NWDAF 2 and/or the data corresponding to the terminal in the terminal list 5 in the to-be-assessed area.

The data analytics information includes one or more of the following information: a terminal list 6, and first risk information, first moving trajectory information, and first risk degree information that are of each terminal in the terminal list 6.

In an example, the NWDAF 1 obtains the data analytics information with reference to the risky terminal list fed back by the NWDAF 2 and the data, obtained in step 809, corresponding to the terminal in the terminal list 5 in the to-be-assessed area. For example, the risky terminal list fed back by the NWDAF 2 includes a terminal 1 to a terminal 3, and the NWDAF 1 further determines first risk information of the terminal 1 and first risk information of the terminal 2 based on data corresponding to each of the terminal 1 to the terminal 3 in the to-be-assessed area, the terminal list 6 includes the terminal 1 and the terminal 2.

For example, for a terminal y, the NWDAF 1 finally generates first risk degree information of the terminal y based on a reference risk degree of the terminal y fed back by the NWDAF 2 and data of the terminal y in the to-be-assessed area. For example, if the NWDAF 2 feeds back that a risk degree of the terminal y is "low", but the NWDAF 1 determines that the terminal y went to a fever clinic in a hospital or a pharmacy in the to-be-assessed area, the NWDAF 1 determines that the first risk degree information of the terminal y is a high risk.

For another example, the NWDAF 1 determines, based on a feedback of the NWDAF 2, that reference risk information of a terminal z shows that a terminal c is a terminal of a risky user, and the NWDAF 1 associates an identifier of a terminal z with moving trajectory information of the terminal z in the to-be-assessed area, to determine first moving trajectory information of the terminal z.

Step 811: The NWDAF 1 sends the data analytics information to the AF network element.

Optionally, a second response message may further include other analytics information that specifically matches content requested by a second request message.

In a possible implementation, the NWDAF 1 may determine, based on the emergency indication information, to allow sending of a response message 2 to the NEF network element.

It may be understood that the NWDAF 1 may send only the terminal list 6 and indication information indicating whether each terminal in the terminal list 6 is a risky terminal to the AF network element. In a possible implementation, the NWDAF 1 may further send the terminal list 6 and the first moving trajectory information, the first risk information, and the first risk degree information that are of the terminal in the terminal list 6 to the AF network element.

For example, the NWDAF 1 may first send the data analytics information to the NEF network element, and the NEF network element forwards the data analytics information to the AF network element.

Optionally, the NEF network element may further convert the data analytics information provided by the NWDAF 1 into data analytics information that may be identified by the AF network element. For example, the data analytics information provided by the NWDAF 1 is the terminal list 6, and the NEF network element converts the terminal list 6 into an identifier list of users of all terminals in the terminal list 6.

Step 812: The AF network element determines an association relationship between each terminal in the terminal list 6 and the emergency event based on the data analytics information.

Optionally, after receiving the data analytics information, the AF network element may further perform a corresponding emergency processing operation based on the data analytics information. For example, the AF network element notifies, based on each terminal in the terminal list 6, a worker to perform personnel prevention and control and an isolation measure on a user of the terminal in the terminal list 6. For example, the AF network element performs key site disinfection, personnel fore-warning, and the like based on the terminal in the terminal list 6 and moving trajectory information.

The terminal list 6 in the embodiment shown in FIG. 8A and FIG. 8B may correspond to the first terminal in the foregoing embodiment. The terminal list 5 corresponds to the fourth terminal in the foregoing embodiment. The terminal list 4 may correspond to the third terminal. The message 1 corresponds to the first request message. The message 3 corresponds to the second request message. The data analytics information corresponds to the data analytics information in the foregoing embodiment.

Figure 9:
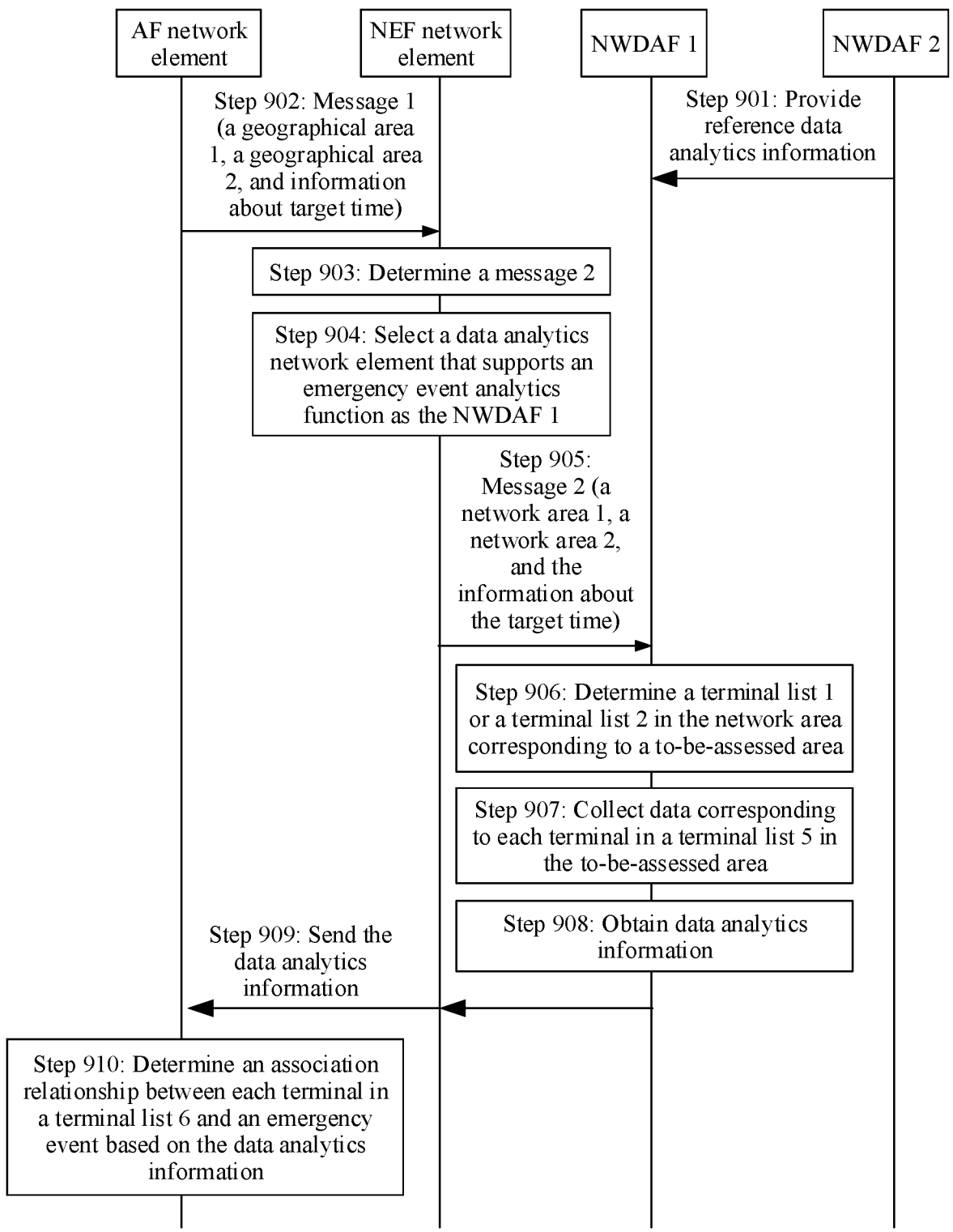

FIG. 9 shows a specific embodiment of another information processing method according to an embodiment of this application. The method includes the following steps.

Step 901: An NWDAF 2 provides reference data analytics information for an NWDAF 1.

Specifically, for content of the reference data analytics information, refer to the descriptions of the embodiment shown in FIG. 8A and FIG. 8B. For example, the NWDAF 2 first determines a terminal list 7 in a network area 2 and reference moving trajectory information, reference activity degree information, and reference risk information that correspond to each terminal in the terminal list 7 to obtain the reference data analytics information, and sends the reference data analytics information to the NWDAF 1.

In a possible implementation, before step 901, the method provided in this embodiment of this application may further include: Step 900: The NWDAF 2 receives a request message from the NWDAF 1, where the request message requests the reference data analytics information. It may be understood that step 900 is an optional step.

In an example, the reference data analytics information provided by the NWDAF 2 for the NWDAF 1 includes a terminal list 8, and reference moving trajectory information and reference risk information that correspond to each terminal in the terminal list 8. A terminal included in the terminal list 8 is a part of terminals in the terminal list 7. For example, the terminal included in the terminal list 8 does not include a terminal that did not leave a network area 2 in a time period. For example, the terminal included in the terminal list 8 is a terminal that is in the network area 2 and that went to a network area 1 in a specified time period. That is, the reference data analytics information provided by the NWDAF 2 for the NWDAF 1 includes a terminal that went to the network area 1 served by the NWDAF 1.

For example, the NWDAF 2 may determine, as a destination (for example, the network area 1), an operator network service register home location of a terminal based on subscription information of the terminal. Alternatively, the NWDAF 2 obtains a travel destination of a user of a terminal from a third-party AF such as a railway, civil aviation, or an automobile, and determines, based on the travel destination of the user, the network area 1 in which the terminal is located.

In a possible implementation, before step 901 in this embodiment of this application, the method may further include: The NWDAF 2 determines the NWDAF 1 that supports an emergency event analytics function. For a specific implementation process in which the NWDAF 2 determines the NWDAF 1 that supports the emergency event analytics function, refer to the descriptions of determining, by the NWDAF 1, the NWDAF 2 that supports the emergency event analytics function in the foregoing embodiment. Details are not described herein again.

Step 902 to step 906 are the same as step 801 to step 805. Details are not described herein again.

Step 907 to step 910 are the same as step 809 to step 812.

It should be noted that the reference data analytics information in step 908 in this embodiment is obtained by the NWDAF 1 by using step 901.

Specifically, in an implementation, the NWDAF 1 obtains an intersection of terminals included in the terminal list 8 and terminals included in the terminal list 5 to obtain a terminal included in the terminal list 6.

The terminal list 8 or the terminal list 7 in the embodiment shown in FIG. 9 corresponds to the third terminal in the foregoing embodiment.

It should be noted that the to-be-assessed area in the embodiment shown in FIG. 9 may also be replaced with a terminal list 9. The terminal list 9 includes p terminals, and p is an integer greater than 1. The terminal list 9 may correspond to the second terminal in the foregoing embodiment.

Figure 10:
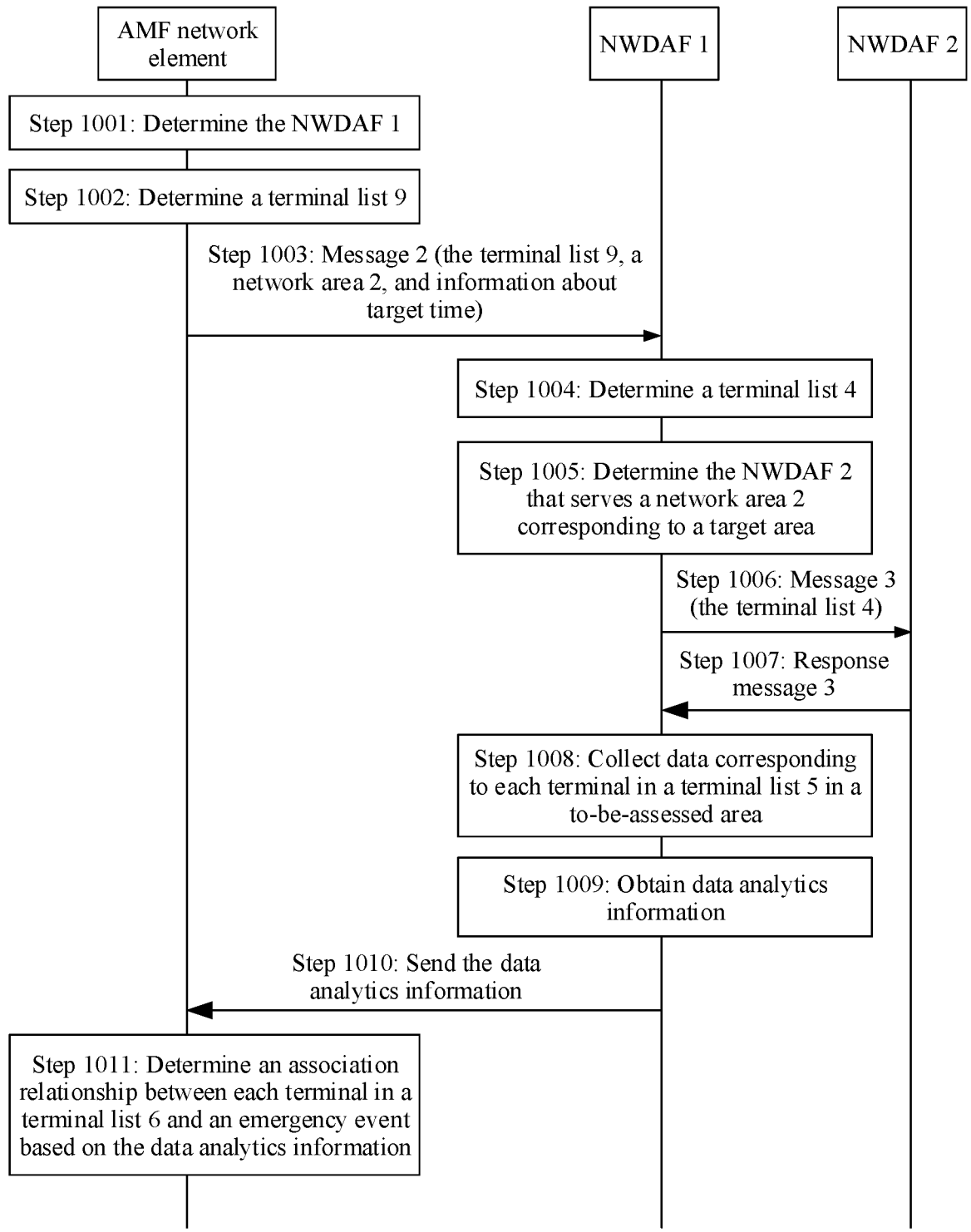

FIG. 10 shows a specific embodiment of another information processing method according to an embodiment of this application. A difference between this embodiment and the embodiment shown in FIG. 8A and FIG. 8B lies in that: In FIG. 10, a first network element 20 is an AMF network element, and a message 1 carries a terminal list 9 instead of information about a to-be-assessed area.

Step 1001: The AMF network element determines an NWDAF 1.

For example, the AMF network element may determine the NWDAF 1 in the following manner: The AMF network element queries, from an NRF network element, information about the NWDAF 1 based on emergency indication information and a network area 1. Alternatively, information about data analytics network elements that provide an emergency event analytics function in different network areas (for example, a network area 1 and a network area 2) is configured in the AMF network element. In this way, the AMF network element may determine the NWDAF 1 in the network area 1 based on a configuration of the AMF network element.

Step 1002: The AMF network element determines the terminal list 9 (corresponding to the foregoing second terminal).

For example, if the AMF network element determines that a terminal that initially registers appears in an area (for example, a TA or a cell), the AMF network element may determine, as a terminal in the terminal list 9, the terminal that initially registers.

Step 1003: The AMF network element sends a message 2 to the NWDAF 1. The message 2 carries the terminal list 9, the network area 2 corresponding to a target area, and information about target time. The message 2 herein corresponds to the first request message in the foregoing embodiment.

Step 1004: The NWDAF 1 determines a terminal list 4. The terminal list 4 includes all or a part of terminals in the terminal list 9.

Step 1005 to step 1011 are the same as step 806 to step 812.

It may be understood that a difference between the embodiment shown in FIG. 10 and the embodiment shown in FIG. 8A and FIG. 8B lies in that: In the embodiment shown in FIG. 8A and FIG. 8B, the AF network element queries, from the NWDAF 1, the data analytics information of the terminal in the to-be-assessed area, and subsequently, the AF network element determines the association relationship between the terminal in the to-be-assessed area and the emergency event. An objective of the embodiment shown in FIG. 10 is as follows: The AMF network element requests the NWDAF 1 to provide data analytics information of a specific terminal (for example, each terminal included in the terminal list 9), so that the AMF network element determines an association relationship between the specific terminal and an emergency event. In addition, the AMF network element does not need to request the data analytics information from the NWDAF 1 by using the NEF network element, and a message that is sent by the AMF network element to the NWDAF network element and that is for requesting the data analytics information carries a network area corresponding to the to-be-assessed area and the network area corresponding to the target area rather than a geographical area.

It should be noted that, in this embodiment of this application, if the data analytics information includes a plurality of types of information, the NWDAF 1 may feed back the plurality of types of information to an AF network element or the AMF network element for one or more times. For example, the NWDAF 1 may first provide the AF network element or the AMF network element with the terminal list 9 and an association relationship between each terminal in the terminal list 9 and the emergency event. Then when the AF network element or the AMF network element requests first risk information, first risk degree information, and first moving trajectory information of the terminal in the terminal list 9, the first risk information, the NWDAF 1 sends the first risk degree information, and the first moving trajectory information that are of the terminal in the terminal list 9 to the AF network element or the AMF network element.

Figure 11:
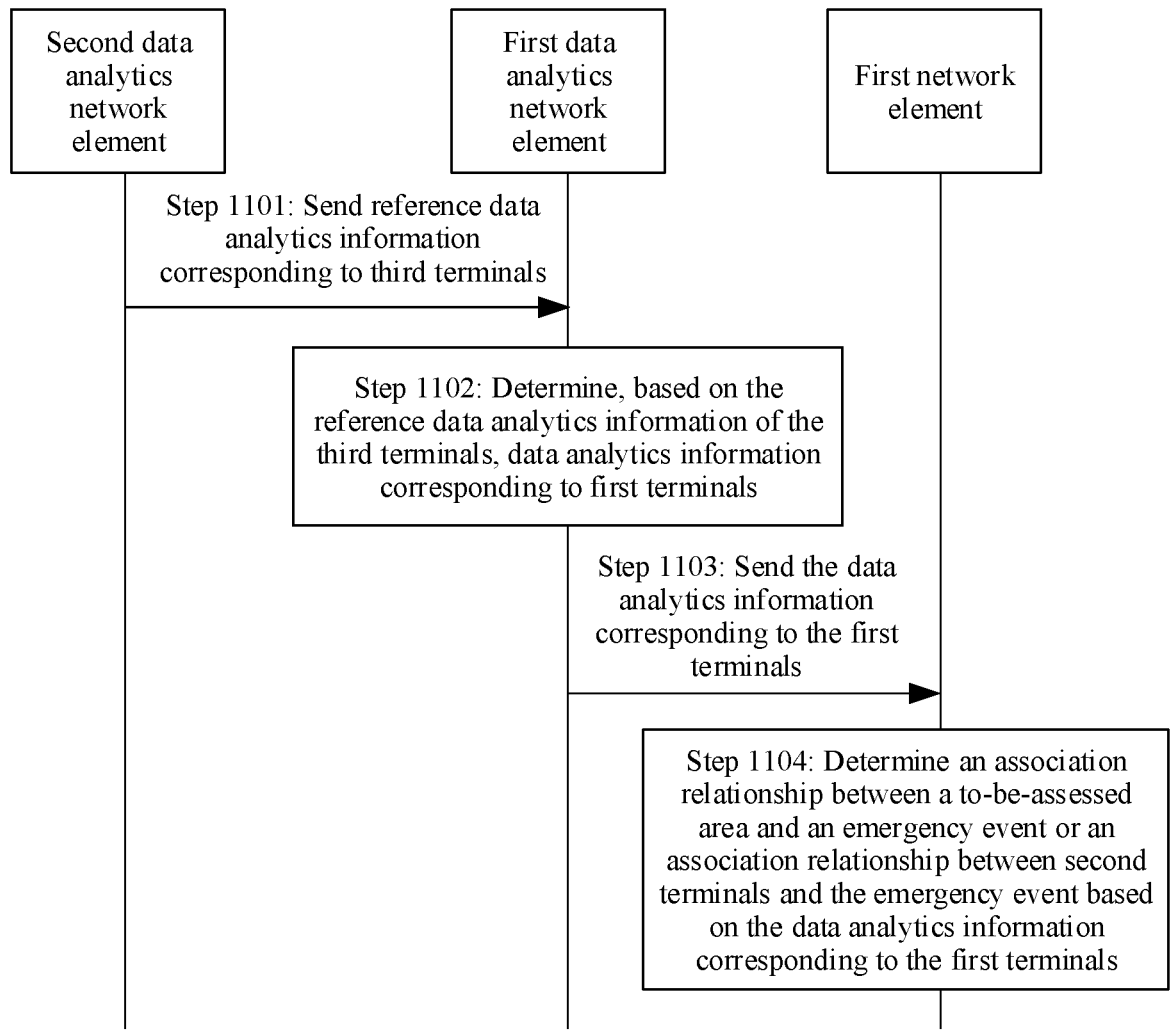
FIG. 11 is a schematic flowchart of another information processing method according to an embodiment of this application.

FIG. 11 shows an embodiment of an information processing method according to an embodiment of this application. The method includes the following steps.

Step 1101: A second data analytics network element 30 sends reference data analytics information corresponding to third terminals to a first data analytics network element 10. Correspondingly, the first data analytics network element 10 obtains, from the second data analytics network element 30, the reference data analytics information corresponding to the third terminals. The third terminals include a terminal that resided in a target area during a target period.

The reference data analytics information corresponding to the third terminals may be actively sent by the second data analytics network element 30 to the first data analytics network element 10. Alternatively, the first data analytics network element sends a request message to the second data analytics network element 30, to request the reference data analytics information corresponding to the third terminals, and then the second data analytics network element 30 performs step 1101. This is not limited in this embodiment of this application.

The third terminals may be all or a part of terminals that resided in the target area during the target period. This is not limited in this embodiment of this application.

A terminal resided in the target area may be understood as that the terminal accessed a network that serves the target area.

For example, the third terminal is a terminal associated with an emergency event. For descriptions of the third terminal, refer to the descriptions in step 701. Details are not described herein again.

In a possible implementation, the reference data analytics information corresponding to the third terminals includes one or more of the following information: identifiers of the third terminals, a quantity of the third terminals, reference activity degree information of the third terminals, reference moving trajectory information of the third terminals, reference risk information of the third terminals, aggregated reference activity degree information of the third terminals, aggregated reference moving trajectory information of the third terminals, and aggregated reference risk information of the third terminals.

For descriptions of the reference activity degree information of the third terminals, the reference moving trajectory information of the third terminals, the reference risk information of the third terminals, refer to the foregoing related descriptions. Details are not described herein again.

The aggregated reference activity degree information of the third terminals may include: average reference activity degree information of a plurality of third terminals or a reference activity degree variance analytics result of the plurality of third terminals. When a reference activity degree of each third terminal is represented as a value, the average reference activity degree information of the plurality of third terminals may be an average value of reference activity degree values corresponding to the third terminals, and the reference activity degree variance analytics result of the plurality of third terminals may be a variance of reference activity degree values corresponding to the third terminals. When a reference activity degree of each third terminal is represented as a level, weighting calculation may be performed, based on a ratio, on levels corresponding to different third terminals, to obtain a weighted value, and cosine classification processing is performed on the weighted value. A level indicated by an obtained cosine classification result is used as an average reference activity degree analytics result of the plurality of third terminals, and the reference activity degree variance analytics result of the plurality of third terminals may be a variance corresponding to reference activity degree levels corresponding to the third terminals.

The aggregated reference moving trajectory information of the third terminals may include a union of locations in reference moving trajectories of the plurality of third terminals or a union of reference moving trajectories.

The aggregated reference risk information of the third terminals includes average information of the reference risk information of the third terminals and/or variance information of the reference risk information of the third terminals. For example, the reference risk information of the third terminals includes one or more of the following information of the third terminals: reference risk classification information, a reference risk degree, and a reference risk removal time point. The reference risk information may also be referred to as a reference risk analytics result.

For descriptions of the identifier of the third terminal, refer to the descriptions of the identifier of the first terminal. Details are not described herein again.

For specific descriptions of step 1101, refer to the descriptions in step 701. Details are not described herein again.

For example, the second data analytics network element 30 and the first data analytics network element 10 serve different areas. For example, the second data analytics network element 30 serves a target area, and the first data analytics network element 10 serves a to-be-assessed area.

It should be understood that, before step 1101, the method provided in this embodiment of this application may further include: The second data analytics network element 30 determines the reference data analytics information corresponding to the third terminals. For a specific process in which the second data analytics network element 30 determines the reference data analytics information corresponding to the third terminals, refer to the specific process in which the second data analytics network element 30 determines the reference data analytics information in the foregoing embodiment. Details are not described herein again.

For example, the first data analytics network element 10 may be the first data analytics network element 10 in FIG. 1. The second data analytics network element 30 may be the second data analytics network element 30 in FIG. 1. The first data analytics network element 10 and the second data analytics network element 30 are data analytics network elements that support an emergency event analytics function.

Step 1102: The first data analytics network element 10 determines, based on the reference data analytics information of the third terminals, data analytics information corresponding to first terminals, where the data analytics information corresponding to the first terminals includes one or more of the following information: a quantity of the first terminals, aggregated activity degree information of the first terminals, aggregated moving trajectory information of the first terminals, and aggregated risk information of the first terminals. The first terminal includes a terminal that is in the third terminals and that is in the to-be-assessed area. Alternatively, the first terminal includes a target terminal, and the target terminal belongs to both the third terminals and second terminals. Alternatively, the first terminal is a second terminal, or the first terminal is a part of second terminals.

In an implementation, that the first terminal includes a terminal that is in the third terminals and that is in the to-be-assessed area may be understood as that the first terminal is all or a part of terminals in the to-be-assessed area in the third terminals. For example, if terminals that access a network that serves the to-be-assessed area are a terminal a and a terminal b, the first terminal may include one or more of the terminal a and the terminal b.

For example, the third terminals are a terminal 1a, a terminal 1b, and a terminal 1c, and the second terminal are a terminal 1d, a terminal 1b, and a terminal 1c. In this case, the target terminal may be one or more of the terminal 1b and the terminal 1c.

In an implementation, the first terminal is a terminal that is associated with the emergency event and that is determined by the first data analytics network element 10.

Step 1103: The first data analytics network element 10 sends the data analytics information corresponding to the first terminals to a first network element 20. Correspondingly, the first network element 20 receives the data analytics information corresponding to the first terminals from the first data analytics network element 10.

For the association relationship between the first terminals and the emergency event in this embodiment of this application, refer to the descriptions in step 503. Details are not described herein again.

In this embodiment of this application, the first data analytics network element 10 may actively send the data analytics information corresponding to the first terminals to the first network element 20. For example, when the emergency event occurs, the first data analytics network element 10 may actively send the data analytics information corresponding to the first terminals to the first network element 20. Alternatively, the first data analytics network element 10 sends, based on triggering of the first network element 20, the data analytics information corresponding to the first terminals to the first network element 20. For specific implementation of step 1103, refer to the descriptions in step 502. Details are not described herein again.

In a possible implementation, the first network element 20 is an application function network element or a mobility management network element.

Step 1104: The first network element 20 determines an association relationship between the to-be-assessed area and the emergency event or an association relationship between the second terminals and the emergency event based on the data analytics information corresponding to the first terminals.

In the foregoing method, the first network element 20 determines the association relationship between the to-be-assessed area and the emergency event or the association relationship between the second terminals and the emergency event based on information such as the quantity of the first terminals, the aggregated activity degree, an aggregated moving trajectory, and an aggregated risk. In this way, a danger degree of the second terminals or the to-be-assessed area can be reflected based on the association relationship. It may be understood that the second terminals may be a terminal group.

It should be understood that, if the first terminal includes the terminal that is in the third terminals and that is in the to-be-assessed area, the first network element 20 determines the association relationship between the to-be-assessed area and the emergency event based on the data analytics information corresponding to the first terminals. If the first terminal is the second terminal, or the first terminal is the part of the second terminal, the first network element 20 determines the association relationship between the second terminals and the emergency event based on the data analytics information corresponding to the first terminals.

If the first terminal includes the target terminal, the first network element 20 determines the association relationship between the to-be-assessed area and the emergency event based on the data analytics information corresponding to the first terminals, and determines the association relationship between the second terminals and the emergency event based on the data analytics information corresponding to the first terminals.

In this embodiment of this application, the association relationship between the second terminals and the emergency event may include: The second terminals are associated with the emergency event, or the second terminals are not associated with the emergency event. When the second terminals are associated with the emergency event, the association relationship between the second terminals and the emergency event may further reflect an association level of the second terminals and the emergency event. For example, the association level is: high association, moderate association, or low association.

For example, in this embodiment of this application, the association relationship between or the association level of the second terminals and the emergency event may be reflected based on the quantity of the first terminals included in the second terminals. For example, the second terminals are the terminal group. If the quantity of the first terminals in the terminal group is greater than a preset quantity of terminals, a higher reflected association level of the terminal group and the emergency event indicates a higher danger degree of the terminal group. In other words, if an association level that is of a terminal group a and the emergency event and that is reflected by an association relationship between the terminal group a and the emergency event is lower than an association level that is of a terminal group b and the emergency event and that is reflected by an association relationship between the terminal group b and the emergency event, a risk degree of the terminal group b is higher than a risk degree of the terminal a.

In this embodiment of this application, the association relationship between the to-be-assessed area and the emergency event may include: The to-be-assessed area is associated with the emergency event, or the to-be-assessed area is not associated with the emergency event. When the to-be-assessed area is associated with the emergency event, the association relationship between the to-be-assessed area and the emergency event may further reflect an association level of the to-be-assessed area and the emergency event.

For example, in this embodiment of this application, the association relationship between or the association level of the to-be-assessed area and the emergency event may be reflected based on the quantity of the first terminals in the to-be-assessed area. For example, if the quantity of the first terminals in the to-be-assessed area is greater than the preset quantity of terminals, a higher reflected association level of the to-be-assessed area and the emergency event indicates a higher risk degree of the to-be-assessed area. In other words, if an association level that is of a to-be-assessed area a and the emergency event and that is reflected by an association relationship between the to-be-assessed area a and the emergency event is lower than an association level that is of a to-be-assessed area b and the emergency event and that is reflected by the association relationship between the to-be-assessed area b and the emergency event, a risk degree of the to-be-assessed area b is higher than a risk degree of the to-be-assessed area a.

It should be understood that after obtaining the association relationship between the second terminals or the to-be-assessed area and the emergency event, the first network element 20 may determine a danger degree of the second terminals or the to-be-assessed area. Then, this helps the first network element 20 execute an associated epidemic processing policy based on the danger degree of the second terminals or the to-be-assessed area. For example, if the quantity of the first terminals is greater than a first preset value, the first network element 20 determines that the to-be-assessed area is associated with the emergency event. In addition, the danger degree is high, and measures such as epidemic prevention and closure need to be taken.

For example, a danger degree in this embodiment of this application may be represented by using A, B, or C. For example, A represents a high danger degree, B represents a moderate danger degree, and C represents a low danger degree. Alternatively, danger degrees in this embodiment of this application may be distinguished by using colors. For example, red indicates a high danger degree, yellow indicates a moderate danger degree, and green indicates a low danger degree. It should be understood that only an example is used herein to describe a representation form of the danger degree.

In a possible embodiment, if the first data analytics network element 10 sends the data analytics information corresponding to the first terminals to the first network element 20 based on triggering of the first network element 20, before step 1103, the method provided in this embodiment of this application may further include: The first network element 20 sends a first request message to the first data analytics network element 10. Correspondingly, the first data analytics network element 10 receives the first request message from the first network element 20. The first request message requests the data analytics information corresponding to the first terminals.

In a possible implementation, the first request message includes one or more of area information corresponding to the target area and time information corresponding to the target period.

The area information corresponding to the target area is used to determine the target area. The time information corresponding to the target period is used to determine the target period.

It should be understood that the first network element 20 provides the first data analytics network element 10 with the area information corresponding to the target area and the time information corresponding to the target period for the first data analytics network element 10 to determine the first terminals.

In another possible implementation, the first request message includes one or more of area information corresponding to the to-be-assessed area and identifiers of the second terminals. If the first request message includes the area information corresponding to the to-be-assessed area, the first request message requests data analytics information corresponding to terminals in the to-be-assessed area. The terminals in the to-be-assessed area include the first terminals, or the first terminals are the terminals in the to-be-assessed area. If the first request message includes the identifiers of the second terminals, the first request message requests data analytics information corresponding to the second terminals. The second terminals include the first terminals, or the second terminals are the first terminals.

In still another possible implementation, the first request message includes area information corresponding to the to-be-assessed area, area information corresponding to the target area, and time information corresponding to the target period. This helps the first data analytics network element 10 determine a terminal that resided in the target area during the target period and that is in the to-be-assessed area as the first terminal.

In yet another possible implementation, the first request message includes area information corresponding to the to-be-assessed area and identifiers of the second terminals. This helps the first data analytics network element 10 obtain an intersection of terminals resided in the to-be-assessed area and the second terminals, to obtain the first terminals.

In a possible implementation, the method provided in this embodiment of this application may further include: The first network element 20 sends emergency indication information to the first data analytics network element 10. Correspondingly, the first data analytics network element 10 receives the emergency indication information from the first network element 20. The emergency indication information indicates, to the first data analytics network element 10, that the data analytics information requested by the first request message is associated with the emergency event. For example, to reduce signaling overheads, the emergency indication information is carried in the first request message.

In a possible implementation, the method provided in this embodiment of this application may further include: The first network element 20 sends emergency event identifier information to the first data analytics network element 10. Correspondingly, the first data analytics network element 10 receives the emergency event identifier information from the first network element 20. The emergency event identifier information uniquely identifies the emergency event. For example, to reduce signaling overheads, the first request message includes the emergency event identifier information.

In a possible implementation, before step 1102, the method provided in this embodiment of this application may further include: The first data analytics network element 10 obtains first input data corresponding to the third terminals in the to-be-assessed area, where the first input data includes one or more of the following information: service behavior information, location information, and moving trajectory information.

The service behavior information corresponding to the third terminals in the to-be-assessed area may be information such as travel information of the third terminals, frequency of entering and exiting an area, or whether, obtained from a medical system, users of the third terminals had a fever or purchased medicine.

In an example, the moving trajectory information corresponding to the third terminals in the to-be-assessed area includes one or more of the following information of the third terminals: location information, a time point of entering a location range corresponding to the location information, and stay duration in the location range.

In a possible implementation, based on the first input data corresponding to the third terminals in the to-be-assessed area, step 1102 in this embodiment of this application may be implemented in the following manner: The first data analytics network element 10 determines, based on the reference data analytics information corresponding to the third terminals and the first input data, the data analytics information corresponding to the first terminals.

For a specific implementation of determining, by the first data analytics network element 10 based on the reference data analytics information corresponding to the third terminals and the first input data, the data analytics information corresponding to the first terminals, refer to the specific implementation of step 705. Details are not described herein again.

In a possible implementation, before step 1102, the method provided in this embodiment of this application may further include: The first data analytics network element 10 obtains second input data corresponding to the target terminal, where the second input data includes one or more of the following information: service behavior information, location information, and moving trajectory information. The moving trajectory information corresponding to the target terminal includes one or more of the following information of the target terminal: the location information, a time point of entering a location range corresponding to the location information, and stay duration in the location range.

In a possible implementation, based on the second input data corresponding to the target terminal, step 1102 in this embodiment of this application may be implemented in the following manner: The first data analytics network element 10 determines, based on reference data analytics information corresponding to the target terminal and the second input data, the data analytics information corresponding to the first terminals.

In a possible implementation, the aggregated activity degree information of the first terminals includes average information of activity degree information of the first terminals and/or variance information of the activity degree information of the first terminals.

For example, the aggregated activity degree information may include average activity degree information of a plurality of first terminals or an activity degree variance analytics result of the plurality of first terminals. When an activity degree of each first terminal is represented as a value, the average activity degree information of the plurality of first terminals may be an average value of activity degree values corresponding to the first terminals, and the activity degree variance analytics result of the plurality of first terminals may be a variance of the activity degree values corresponding to the first terminals. When an activity degree of each first terminal is represented as a level, weighting calculation may be performed, based on a ratio, on levels corresponding to different first terminals, to obtain a weighted value, and cosine classification processing is performed on the weighted value. A level indicated by an obtained cosine classification result is used as an average activity degree analytics result of the plurality of first terminals, and the activity degree variance analytics result of the plurality of first terminals may be a variance corresponding to activity degree levels corresponding to the first terminals.

In a possible implementation, the aggregated moving trajectory information of the first terminal includes a union of locations of moving trajectories of the plurality of first terminals or a union of the moving trajectories.

In a possible implementation, the aggregated risk information of the first terminal includes average information of risk information of the first terminals and/or variance information of the risk information of the first terminals. For example, the risk information of the first terminals includes one or more of the following information of the first terminals: risk classification information, a risk degree, and a risk removal time point. The risk information may also be referred to as a risk analytics result.

For example, the aggregated risk information may include average risk information of the plurality of first terminals or a risk variance analytics result of the plurality of first terminals. An average risk degree analytics result is similar to the average activity degree analytics result. When a risk degree of each first terminal is represented as a value, the average risk degree analytics result of the plurality of first terminals may be an average value of risk degree values corresponding to the first terminals, and a risk degree variance analytics result of the plurality of first terminals may be a variance of the risk degree values corresponding to the first terminals. When a risk degree of each first terminal is represented as a level, weighting calculation may be performed, based on a ratio, on levels corresponding to different first terminals, to obtain a weighted value, and cosine classification processing is performed on the weighted value. A level indicated by an obtained cosine classification result is used as the average risk degree analytics result of the plurality of first terminals, and the risk degree variance analytics result of the plurality of first terminals may be a variance of risk degree levels corresponding to the first terminals.

There are a plurality of first terminals, a plurality of second terminals, and a plurality of third terminals.

In a possible implementation, the method provided in this embodiment of this application includes: The first network element 20 determines, based on the data analytics information corresponding to the first terminals, a danger degree of the to-be-assessed area or the second terminals that is caused by the emergency event. It should be understood that the second terminals may be the terminal group, the terminal group includes m terminals, and m is an integer greater than or equal to 1.

In a possible implementation, when the first network element 20 is the mobility management network element, the method provided in this embodiment of this application further includes: The first network element 20 obtains the emergency indication information. The first network element 20 selects a data analytics network element that supports the emergency event analytics function as the first data analytics network element 10 based on the emergency indication information.

In a possible embodiment, after step 1104, the method provided in this embodiment of this application further includes: The first network element 20 performs, based on the association relationship, an emergency processing operation corresponding to the emergency event.

In a possible implementation, that the first network element 20 performs, based on the association relationship, an emergency processing operation corresponding to the emergency event includes: The first network element 20 sends first notification information to a sixth terminal, where the first notification information notifies the sixth terminal of the association relationship between the to-be-assessed area and the emergency event, where the sixth terminal includes a terminal that is currently located in the to-be-assessed area; and/or the first network element 20 sends second notification information to a second network element, where the second notification information notifies the second network element of the association relationship between the to-be-assessed area and the emergency event. For example, the second network element may be an emergency center platform deployed by an operator, and the platform is responsible for releasing an emergency event-associated fore-warning message and the like to a terminal in a network. The first network element 20 (for example, an AMF network element) notifies the second network element (for example, the emergency center platform) of the association relationship, so that the second network element sends the fore-warning information to a user terminal in the network.

In another possible implementation, that the first network element 20 performs, based on the association relationship, an emergency processing operation corresponding to the emergency event includes: The first network element 20 sends third notification information to a seventh terminal, where the third notification information notifies the seventh terminal of the association relationship between the second terminals and the emergency event, and the seventh terminal belongs to the second terminals; and/or the first network element 20 sends fourth notification information to a second network element, where the fourth notification information notifies the second network element of the association relationship between the second terminals and the emergency event.

That the seventh terminal belongs to the second terminals may be understood as follows: The seventh terminal is the second terminal, or the seventh terminal is a part of the second terminals. This is not limited in this embodiment of this application.

The foregoing describes the solutions in embodiments of this application mainly from a perspective of interaction between network elements. It may be understood that, to implement the foregoing functions, each network element, such as the first data analytics network element, the second data analytics network element, or the first network element, includes a corresponding hardware structure and/or software module for executing each function. A person skilled in the art should be easily aware that, in combination with units and algorithm steps of the examples described in embodiments disclosed in this specification, this application can be implemented by hardware or a combination of hardware and computer software. Whether a function is performed by hardware or hardware driven by computer software depends on particular applications and design constraints of the technical solutions. A person skilled in the art may use different methods to implement the functions of each particular application, but it should not be considered that the implementation goes beyond the scope of this application.

In embodiments of this application, the first data analytics network element, the second data analytics network element, or the first network element may be divided into function units based on the foregoing method examples. For example, function units may be obtained through division based on corresponding functions, or two or more functions may be integrated into one processing unit. The integrated unit may be implemented in a form of hardware, or may be implemented in a form of a software functional unit. It should be noted that, in embodiments of this application, division into the units is an example, and is merely logical function division. During actual implementation, another division manner may be used.

The foregoing describes the method in embodiments of this application with reference to FIG. 5 to FIG. 11. The following describes an information processing apparatus that is provided in embodiments of this application and that performs the foregoing method. A person skilled in the art may understand that the method and the apparatus may be combined with and referenced to each other, and the information processing apparatus provided in embodiments of this application may perform the steps performed by the first data analytics network element, the second data analytics network element, and the first network element in the foregoing analytics method.

Figure 12:
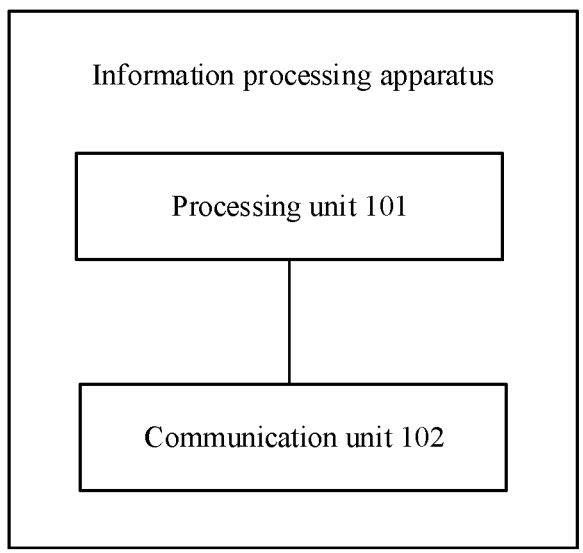
FIG. 12 is a schematic diagram of a structure of an information processing apparatus according to an embodiment of this application.

FIG. 12 shows an information processing apparatus in the foregoing embodiment. The information processing apparatus may include a communication unit 102 and a processing unit 101.

Optionally, the information processing apparatus may further include a storage unit, configured to store information. For example, if the information processing apparatus is a first network element, the storage unit may store an association relationship between a first terminal and an emergency event. For example, if the information processing apparatus is a first data analytics network element, the storage unit may store reference data analytics information, data analytics information, and the like.

In a possible implementation, the communication unit may include a receiving unit and a sending unit. The receiving unit is configured to receive a signal, and the sending unit is configured to send a signal.

In an example, the information processing apparatus is the first data analytics network element or a component (for example, a chip) used in the first data analytics network element. In this case, the communication unit 102 is configured to support the information processing apparatus in communicating with an external network element, for example, performing the signal receiving and sending operation of the first data analytics network element 10 in the foregoing method embodiment. The processing unit 101 is configured to perform the signal processing operation of the first data analytics network element 10 in the foregoing method embodiment. For example, the communication unit 102 is configured to perform the receiving action performed by the first data analytics network element 10 in step 502 in FIG. 5 in the foregoing embodiment. The processing unit 101 is configured to support the information processing apparatus in performing the action performed by the first data analytics network element 10 in step 501 in FIG. 5.

In a possible embodiment, the communication unit 102 is further configured to support the information processing apparatus in performing the receiving actions performed by the first data analytics network element 10 in step 601 and step 703 in the foregoing embodiments, and the communication unit 102 is further configured to support the information processing apparatus in performing the sending action performed by the first data analytics network element 10 in step 702 in the foregoing embodiment. The processing unit 101 is further configured to support the information processing apparatus in performing the actions performed by the first data analytics network element 10 in step 704 and step 705 in the foregoing embodiment.

In another example, the information processing apparatus is the first network element or a chip used in the first network element. In this case, the communication unit 102 is configured to support the information processing apparatus in communicating with an external network element, for example, performing the signal receiving and sending operation of the first network element 20 in the foregoing method embodiment. The processing unit 101 is configured to perform the signal processing operation of the first network element 20 in the foregoing method embodiment. For example, the processing unit 101 is configured to support the information processing apparatus in performing the action performed by the first network element 20 in step 503 in the foregoing embodiment, and the communication unit 102 is configured to support the information processing apparatus in performing the receiving action performed by the first network element 20 in step 502 in the foregoing embodiment.

In a possible embodiment, the communication unit 102 is further configured to support the information processing apparatus in performing the sending action performed by the first network element 20 in step 601 in the foregoing embodiment. The processing unit 101 is further configured to support the information processing apparatus in performing step 605 performed by the first network element 20 in the foregoing embodiment.

In still another example, the information processing apparatus is a second data analytics network element or a chip used in the second data analytics network element. In this case, the communication unit 102 is configured to support the information processing apparatus in communicating with an external network element, for example, performing the signal receiving and sending operation of the second data analytics network element 30 in the foregoing method embodiment. The processing unit 101 is configured to perform the signal processing operation of the second data analytics network element 30 in the foregoing method embodiment. For example, the processing unit 101 is configured to support the information processing apparatus in performing the action performed by the second data analytics network element 30 in step 701 in the foregoing embodiment, and the communication unit 102 is configured to support the information processing apparatus in performing the receiving action performed by the second data analytics network element 30 in step 702 in the foregoing embodiment. The communication unit 102 is further configured to support the information processing apparatus in performing the sending action performed by the second data analytics network element 30 in step 702 in the foregoing embodiment.

It should be noted that, when a first data analytics network element 10 does not perform the sending action in step 702, the receiving action in step 702 performed by the communication unit 101 may be omitted.

In yet another example, the information processing apparatus is a second data analytics network element or a chip used in the second data analytics network element. In this case, the communication unit 102 is configured to support the information processing apparatus in communicating with an external network element, for example, performing the signal receiving and sending operation of the second data analytics network element 30 in the foregoing method embodiment. The processing unit 101 is configured to perform the signal processing operation of the second data analytics network element 30 in the foregoing method embodiment. For example, the communication unit 102 is configured to support the information processing apparatus in performing the sending action performed by the second data analytics network element 30 in step 1101 in the foregoing embodiment.

In yet another example, the information processing apparatus is the first data analytics network element or a chip used in the first data analytics network element. In this case, the communication unit 102 is configured to support the information processing apparatus in communicating with an external network element, for example, performing the signal receiving and sending operation of the first data analytics network element 10 in the foregoing method embodiment. The processing unit 101 is configured to perform the signal processing operation of the first data analytics network element 10 in the foregoing method embodiment. For example, the communication unit 102 is configured to support the information processing apparatus in performing the receiving action performed by the first data analytics network element 10 in step 1101 in the foregoing embodiment. The processing unit 101 is configured to support the information processing apparatus in performing the action performed by the first data analytics network element 10 in step 1102 in the foregoing embodiment. The communication unit 102 is configured to support the information processing apparatus in performing the receiving action performed by the first data analytics network element 10 in step 1103 in the foregoing embodiment.

In yet another example, the information processing apparatus is the first network element or a chip used in the first network element. In this case, the communication unit 102 is configured to support the information processing apparatus in communicating with an external network element, for example, performing the signal receiving and sending operation of the first network element 20 in the foregoing method embodiment. The processing unit 101 is configured to perform the signal processing operation of the first network element 20 in the foregoing method embodiment. For example, the communication unit 102 is configured to support the information processing apparatus in performing the receiving action performed by the first network element 20 in step 1103 in the foregoing embodiment. The processing unit 101 is configured to support the information processing apparatus in performing the action of the first network element 20 in step 1104 in the foregoing embodiment.

When an integrated unit is used, the communication unit shown in FIG. 12 may be alternatively replaced with a communication module, and the processing unit may be alternatively replaced with a processing module. The storage unit may be replaced with a storage module. The processing module is configured to control and manage an action of the information processing apparatus. For example, the processing module is configured to perform a step of performing information/data processing in the information processing apparatus. The communication module is configured to support the information processing apparatus in performing an information/data sending or receiving step. In a possible embodiment, the information processing apparatus may further include the storage module, configured to store program code and data that may be used by the information processing apparatus.

The processing module may be a processor or a controller, for example, may be a central processing unit, a general-purpose processor, a digital signal processor, an application-specific integrated circuit, a field programmable gate array or another programmable logic device, a transistor logic device, a hardware component, or any combination thereof. The processing module may implement or execute various example logical blocks, modules, and circuits described with reference to content disclosed in this application. Alternatively, the processor may be a combination of processors implementing a computing function, for example, a combination of one or more microprocessors or a combination of a digital signal processor and a microprocessor. The communication module may be a transceiver, a transceiver circuit, a communication interface, or the like. The storage module may be a memory.

When the processing module is a processor 41 or a processor 45, the communication module is a communication interface 43, and the storage module is a memory 42, the information processing apparatus in this application may be the communication device shown in FIG. 4.

Figure 13:
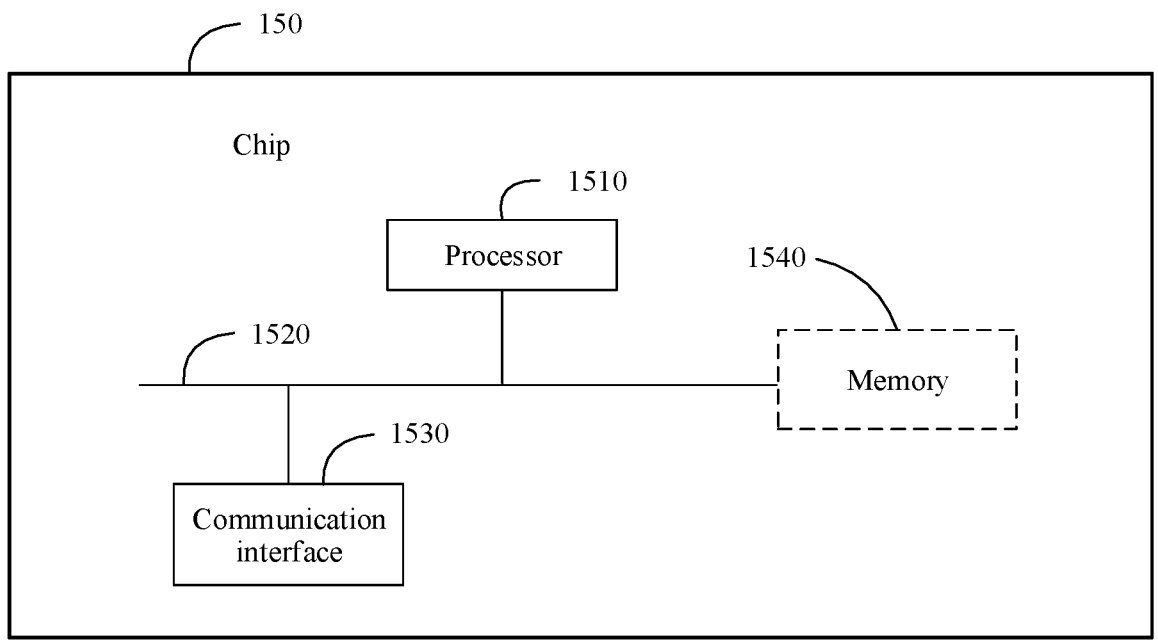
FIG. 13 is a schematic diagram of a structure of a chip according to an embodiment of this application.

FIG. 13 is a schematic diagram of a structure of a chip 150 according to an embodiment of this application. The chip 150 includes at least one or at least two (including two) processors 1510 and a communication interface 1530.

Optionally, the chip 150 further includes a memory 1540. The memory 1540 may include a read-only memory and a random access memory, and provide operation instructions and data for the processor 1510. A part of the memory 1540 may further include a non-volatile random access memory (NVRAM).

In some implementations, the memory 1540 stores the following elements: an executable module or a data structure, a subset thereof, or an extended set thereof.

In this embodiment of this application, the operation instructions stored in the memory 1540 (where the operation instructions may be stored in an operating system) are invoked to perform a corresponding operation.

In a possible implementation, structures of chips used by a first data analytics network element 10, a second data analytics network element 30, and a first network element 20 are similar, and different apparatuses may use different chips to implement respective functions.

The processor 1510 controls a processing operation of any one of the first data analytics network element 10, the second data analytics network element 30, and the first network element 20. The processor 1510 may also be referred to as a central processing unit (CPU).

The memory 1540 may include the read-only memory and the random access memory, and provide the instructions and the data for the processor 1510. The part of the memory 1540 may further include the NVRAM. For example, during application, the processor 1510, the communication interface 1530, and the memory 1540 are coupled together by using a bus system 1520. In addition to a data bus, the bus system 1520 may further include a power bus, a control bus, a status signal bus, and the like. However, for clear descriptions, various buses are marked as the bus system 1520 in FIG. 13.

The methods disclosed in the foregoing embodiments of this application may be applied to the processor 1510, or may be implemented by the processor 1510. The processor 1510 may be an integrated circuit chip, and has a signal processing capability. In an implementation process, the steps in the foregoing methods may be implemented by using a hardware integrated logical circuit in the processor 1510 or instructions in a form of software. The processor 1510 may be a general-purpose processor, a digital signal processor (DSP), an ASIC, a field-programmable gate array (FPGA) or another programmable logic device, a discrete gate or a transistor logic device, or a discrete hardware component. The processor 1510 may implement or perform the methods, steps, and logical block diagrams that are disclosed in embodiments of this application. The general-purpose processor may be a microprocessor, or the processor may be any conventional processor or the like. Steps of the method disclosed with reference to embodiments of this application may be directly performed and completed by using a hardware decoding processor, or may be performed and completed by using a combination of hardware and software modules in the decoding processor. The software module may be located in a mature storage medium in the art, such as a random access memory, a flash memory, a read-only memory, a programmable read-only memory, an electrically erasable programmable memory, or a register. The storage medium is located in the memory 1540, and the processor 1510 reads information in the memory 1540 and completes the steps in the foregoing method in combination with hardware of the processor 1510.

In a possible implementation, the communication interface 1530 is configured to perform the receiving and sending steps of the first data analytics network element 10, the second data analytics network element 30, and the first network element 20 in the embodiments shown in FIG. 5 to FIG. 10. The processor 1510 is configured to perform the processing steps of the first data analytics network element 10, the second data analytics network element 30, and the first network element 20 in the embodiments shown in FIG. 5 to FIG. 10.

In a possible implementation, the communication interface 1530 is configured to perform the receiving and sending steps of the first data analytics network element 10, the second data analytics network element 30, and the first network element 20 in the embodiment shown in FIG. 11. The processor 1510 is configured to perform the processing steps of the first data analytics network element 10, the second data analytics network element 30, and the first network element 20 in the embodiment shown in FIG. 11.

The communication unit may be a communication interface of the apparatus, and is configured to receive a signal from another apparatus. For example, when the apparatus is implemented as a chip, the communication unit is a communication interface used by the chip to receive a signal from or send a signal to another chip or apparatus.

According to an aspect, a computer-readable storage medium is provided. The computer-readable storage medium stores instructions. When the instructions are run, the function of the first data analytics network element in FIG. 5 is implemented.

In a possible embodiment, when the instructions are run, the function of the first data analytics network element in FIG. 6 and FIG. 7 may further be implemented.

According to an aspect, a computer-readable storage medium is provided. The computer-readable storage medium stores instructions. When the instructions are run, the function of the first data analytics network element in FIG. 11 is implemented.

According to an aspect, a computer-readable storage medium is provided. The computer-readable storage medium stores instructions. When the instructions are run, the function of the first network element in FIG. 5 is implemented.

In a possible embodiment, when the instructions are run, the computer-readable storage medium may further implement the function of the first network element in FIG. 6.

According to an aspect, a computer-readable storage medium is provided. The computer-readable storage medium stores instructions. When the instructions are run, the function of the first network element in FIG. 11 is implemented.

According to an aspect, a computer-readable storage medium is provided. The computer-readable storage medium stores instructions. When the instructions are run, the function of the second data analytics network element in FIG. 7 is implemented.

According to an aspect, a computer program product including instructions is provided. The computer program product includes the instructions. When the instructions are run, the function of the first data analytics network element in FIG. 5 is implemented.

In a possible embodiment, when the instructions are run, the computer program product including the instructions may further implement the function of the first data analytics network element in FIG. 6 and FIG. 7.

According to an aspect, a computer-readable storage medium is provided. The computer-readable storage medium stores instructions. When the instructions are run, the function of the second data analytics network element in FIG. 11 is implemented.

According to another aspect, a computer program product including instructions is provided. The computer program product includes the instructions. When the instructions are run, the function of the first network element in FIG. 5 is implemented.

In a possible embodiment, when the instructions are run, the computer program product including the instructions may further implement the function of the first network element in FIG. 6.

According to another aspect, a computer program product including instructions is provided. The computer program product includes the instructions. When the instructions are run, the function of the first network element in FIG. 11 is implemented.

According to another aspect, a computer program product including instructions is provided. The computer program product includes the instructions. When the instructions are run, the function of the second data analytics network element in FIG. 7 is implemented.

According to another aspect, a computer program product including instructions is provided. The computer program product includes the instructions. When the instructions are run, the function of the second data analytics network element in FIG. 11 is implemented.

According to another aspect, a computer program product including instructions is provided. The computer program product includes the instructions. When the instructions are run, the function of the first data analytics network element in FIG. 11 is implemented.

According to an aspect, a chip is provided. The chip is used in a first data analytics network element. The chip includes at least one processor and a communication interface, the communication interface is coupled to the at least one processor, and the processor is configured to execute instructions, to implement the function of the first data analytics network element in FIG. 5 to FIG. 7.

According to another aspect, a chip is provided. The chip is used in a first network element. The chip includes at least one processor and a communication interface, the communication interface is coupled to the at least one processor, and the processor is configured to execute instructions, to implement the function of the first network element in FIG. 5 or FIG. 6.

According to another aspect, a chip is provided. The chip is used in a second data analytics network element. The chip includes at least one processor and a communication interface, the communication interface is coupled to the at least one processor, and the processor is configured to execute instructions, to implement the function of the second data analytics network element in FIG. 7.

According to an aspect, a chip is provided. The chip is used in a first data analytics network element. The chip includes at least one processor and a communication interface, the communication interface is coupled to the at least one processor, and the processor is configured to execute instructions, to implement the function of the first data analytics network element in FIG. 11.

According to another aspect, a chip is provided. The chip is used in a first network element. The chip includes at least one processor and a communication interface, the communication interface is coupled to the at least one processor, and the processor is configured to execute instructions, to implement the function of the first network element in FIG. 11.

According to another aspect, a chip is provided. The chip is used in a second data analytics network element. The chip includes at least one processor and a communication interface, the communication interface is coupled to the at least one processor, and the processor is configured to execute instructions, to implement the function of the second data analytics network element in FIG. 11.

An embodiment of this application provides a communication system. The communication system includes a first data analytics network element and a first network element. The first data analytics network element is configured to perform any function performed by the first data analytics network element in FIG. 5 to FIG. 7, and the first network element is configured to perform a function performed by the first network element in FIG. 5 or FIG. 6.

Optionally, the communication system may further include a second data analytics network element, configured to perform a corresponding function performed by the second data analytics network element in FIG. 7.

All or some of the foregoing embodiments may be implemented by using software, hardware, firmware, or any combination thereof. When software is used to implement embodiments, all or a part of embodiments may be implemented in a form of a computer program product. The computer program product includes one or more computer programs or instructions. When the computer programs or the instructions are loaded and executed on a computer, the procedures or the functions according to embodiments of this application are all or partially implemented. The computer may be a general-purpose computer, a dedicated computer, a computer network, a network device, user equipment, or another programmable apparatus. The computer programs or the instructions may be stored in a computer-readable storage medium, or may be transmitted from a computer-readable storage medium to another computer-readable storage medium. For example, the computer programs or the instructions may be transmitted from a website, computer, server, or data center to another website, computer, server, or data center in a wired or wireless manner. The computer-readable storage medium may be any usable medium accessible by a computer, or a data storage device, such as a server or a data center, integrating one or more usable media. The usable medium may be a magnetic medium, for example, a floppy disk, a hard disk, or a magnetic tape, may be an optical medium, for example, a digital video disc (DVD), or may be a semiconductor medium, for example, a solid-state drive (SSD).

Although this application is described with reference to embodiments herein, in a process of implementing this application that claims protection, a person skilled in the art may understand and implement another variation of the disclosed embodiments by viewing the accompanying drawings, disclosed content, and the appended claims. In the claims, "comprising" does not exclude another component or another step, and "a" or "one" does not exclude a case of plurality. A single processor or another unit may implement several functions enumerated in the claims. Some measures are recorded in dependent claims that are different from each other, but this does not mean that the measures cannot be combined to produce a good effect.

Although this application is described with reference to specific features and embodiments thereof, it is clear that various modifications and combinations may be made to them without departing from the spirit and scope of this application. Correspondingly, the specification and accompanying drawings are merely example description of this application defined by the appended claims, and are considered as any of and all modifications, variations, combinations or equivalents that cover the scope of this application. It is clear that a person skilled in the art can make various modifications and variations to this application without departing from the spirit and scope of this application. This application is intended to cover these modifications and variations of this application provided that they fall within the scope of the claims of this application and their equivalent technologies.

What is claimed is:

1. A method applied for a first data analytics network element, comprising:
    obtaining reference data analytics information corresponding to second terminal from a second data analytics network element, wherein the second terminal comprises at least one terminal residing in a target area during a target period and wherein the reference data analytics information is determined by the second data analytics network element;
    determining data analytics information corresponding to a first terminal based on the reference data analytics information corresponding to the second terminal, wherein the first terminal comprises at least one terminal that belongs to the second terminal and currently resides in a to-be-assessed area; and
    sending the data analytics information corresponding to the first terminal to a first network element.

2. The method of claim 1, further comprising:
    receiving a first request message from the first network element, wherein the first request message requests the data analytics information corresponding to the first terminal.

3. The method of claim 2, wherein the first request message comprises information of the target area and information of the target period.

4. The method of claim 3, wherein the first request message further comprises information of the to-be-assessed area.

5. The method of claim 3, wherein the first request message further comprises an identifier of the first terminal.

6. The method of claim 1, further comprising:
obtaining data corresponding to one of the first terminal in the to-be-assessed area, wherein the data comprises at least one of service behavior information, location information, or moving trajectory information.

7. The method of claim 6, wherein the moving trajectory information comprises at least one of location information, a time point of entering a location range corresponding to the location information, or stay duration in the location range.

8. The method of claim 6, wherein determining the data analytics information corresponding to the first terminal based on the reference data analytics information corresponding to the second terminal comprises:
determining the data analytics information corresponding to the first terminal based on the reference data analytics information from the second data analytics network element and the data corresponding to the first terminal in the to-be-assessed area.

9. The method of claim 1, wherein the reference data analytics information corresponding to the second terminal comprises at least one of identifiers of the second terminal, a quantity of the second terminal, reference activity degree information of the second terminal, reference moving trajectory information of the second terminal, reference risk information of the second terminal, aggregated reference activity degree information of the second terminal, aggregated reference moving trajectory information of the second terminal, or aggregated reference risk information of the second terminal.

10. The method of claim 1, wherein the target area is served by the second data analytics network element, and the to-be-assessed area is served by the first data analytics network element.

11. An apparatus, comprising:
a non-transitory memory comprising instructions, and one or more processors in communication with the memory, wherein the one or more processors execute the instructions to:
obtain reference data analytics information corresponding to second terminal from a second data analytics network element, wherein the second terminal comprises at least one terminal residing in a target area during a target period and wherein the reference data analytics information is determined by the second data analytics network element;
determine data analytics information corresponding to a first terminal based on the reference data analytics information corresponding to the second terminal, wherein the first terminal comprises at least one terminal that belongs to the second terminal and currently resides in a to-be-assessed area; and
send the data analytics information corresponding to the first terminal to a first network element.

12. The apparatus of claim 11, wherein the one or more processors further execute the instructions to:
receive a first request message from the first network element, wherein the first request message requests the data analytics information corresponding to the first terminal.

13. The apparatus of claim 12, wherein the first request message comprises information of the target area and information of the target period.

14. The apparatus of claim 12, wherein the first request message comprises information of the to-be-assessed area.

15. The apparatus of claim 11, wherein the one or more processors further execute the instructions to:
obtain data corresponding to one of the first terminal in the to-be-assessed area, wherein the data comprises at least one of service behavior information, location information, or moving trajectory information.

16. The apparatus of claim 15, wherein the moving trajectory information comprises at least one of location information, a time point of entering a location range corresponding to the location information, or stay duration in the location range.

17. The apparatus of claim 11, wherein determine data analytics information corresponding to a first terminal based on the reference data analytics information of the second terminal comprises:
determine data analytics information corresponding to the first terminal based on the reference data analytics information from the second data analytics network element and the data corresponding to the first terminal in the to-be-assessed area.

18. The apparatus of claim 11, wherein the reference data analytics information corresponding to the second terminal comprises at least one of identifiers of the second terminal, a quantity of the second terminal, reference activity degree information of the second terminal, reference moving trajectory information of the second terminal, reference risk information of the second terminal, aggregated reference activity degree information of the second terminal, aggregated reference moving trajectory information of the second terminal, or aggregated reference risk information of the second terminal.

19. The apparatus of claim 11, wherein the target area is served by the second data analytics network element, the to-be-assessed area is served by the apparatus.

20. A communication system, comprising:
a first data analytics network element, configured to:
obtain reference data analytics information corresponding to a second terminal from a second data analytics network element, wherein the second terminal comprises at least one terminal residing in a target area during a target period;
determine data analytics information corresponding to a first terminal based on the reference data analytics information corresponding to the second terminal, wherein the first terminal comprises at least one terminal that belongs to the second terminal and currently resides in a to-be-assessed area; and
send the data analytics information corresponding to the first terminal to a first network element; and
the second data analytics network element, configured to:
send the reference data analytics information corresponding to the second terminal to the first data analytics network element.

* * * * *